(12) United States Patent
Leary et al.

(10) Patent No.: US 9,878,002 B2
(45) Date of Patent: Jan. 30, 2018

(54) COMPOSITIONS AND METHODS INVOLVING ENDOGENOUS RETROVIRUS PROTEINS

(71) Applicant: REGENTS OF THE UNIVERSITY OF MINNESOTA, Minneapolis, MN (US)

(72) Inventors: Robyn Lynn Leary, La Jolla, CA (US); Anindya Bagchi, Minneapolis, MN (US); Aaron Lyman Sarver, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/762,856

(22) PCT Filed: Jan. 24, 2014

(86) PCT No.: PCT/US2014/012964
§ 371 (c)(1),
(2) Date: Jul. 23, 2015

(87) PCT Pub. No.: WO2014/116958
PCT Pub. Date: Jul. 31, 2014

(65) Prior Publication Data
US 2015/0352179 A1    Dec. 10, 2015

Related U.S. Application Data

(60) Provisional application No. 61/756,937, filed on Jan. 25, 2013.

(51) Int. Cl.
*C12N 15/00* (2006.01)
*A61K 38/16* (2006.01)
(Continued)

(52) U.S. Cl.
CPC ........ *A61K 38/162* (2013.01); *A61K 38/1758* (2013.01); *A61K 39/39558* (2013.01);
(Continued)

(58) Field of Classification Search
None
See application file for complete search history.

(56) References Cited

FOREIGN PATENT DOCUMENTS

| EP | 2402447 A1 | 1/2012 |
|---|---|---|
| FR | 2 928 659 A1 | 9/2009 |

(Continued)

OTHER PUBLICATIONS

Rolland et al., "The Envelope Protein of a Human Endogenous Retrovirus-W Family Activates Innate Immunity through CD14/TLR4 and Promotes Th1-Like Responses," J. Immunol. 176: 7636-7644 (2006).*

(Continued)

*Primary Examiner* — Janet L Andres
*Assistant Examiner* — M. Franco Salvoza
(74) *Attorney, Agent, or Firm* — Mueting, Raasch & Gebhardt, PA

(57) ABSTRACT

This disclosure describes methods and compositions that involve endogenous retrovirus proteins as diagnostic markers and/or therapeutic agents. The detection of endogenous retrovirus envelope proteins on a cell surface can indicate early neoplasticity of the cell. Antibody compositions that specifically bind to cell-surface-expressed endogenous retrovirus proteins may be used in such diagnostic methods. Overexpression of the endogenous retrovirus proteins can slow cell growth and decrease cell viability.

10 Claims, 15 Drawing Sheets

(51) Int. Cl.
| | |
|---|---|
| C07K 14/005 | (2006.01) |
| A61K 39/42 | (2006.01) |
| A61K 39/395 | (2006.01) |
| A61K 38/17 | (2006.01) |
| C12Q 1/68 | (2006.01) |
| C12Q 1/70 | (2006.01) |
| A61K 39/00 | (2006.01) |
| A61K 48/00 | (2006.01) |

(52) U.S. Cl.
CPC .......... *A61K 39/42* (2013.01); *A61K 48/0058* (2013.01); *C07K 14/005* (2013.01); *C12Q 1/68* (2013.01); *C12Q 1/702* (2013.01); *A61K 48/00* (2013.01); *A61K 2039/507* (2013.01); *C12N 2740/10033* (2013.01); *C12Q 2600/118* (2013.01)

(56) References Cited

FOREIGN PATENT DOCUMENTS

| WO | WO 2004/043371 A2 | 5/2004 |
|---|---|---|
| WO | WO 2006/055697 A2 | 5/2006 |
| WO | WO 2008/008155 A2 | 1/2008 |
| WO | WO 2012/118974 A2 | 9/2012 |

OTHER PUBLICATIONS

Horn et al., "Coping with stress: multiple ways to activate p53," Oncogene 26:1306-1316 (2007).*
Lakin et al., "Regulation of p53 in response to DNA damage," Oncogene 18:7644-7655 (1999).*
He et al., "Upregulation of p53 Expression in Patients with Colorectal Cancer by Administration of Curcumin," Cancer Investigation 29:208-213 (2011).*
Chang et al., "The transcriptional activity of HERV-I LTR is negatively regulated by its cis-elements and wild type p53 tumor suppressor protein," Journal of Biomedical Science 14:211-222 (2007).*
Belshaw et al. "Long-term reinfection of the human genome by endogenous retroviruses," PNAS, vol. 10, No. 14: 4894-4899 (2004).*
International Search Report and Written Opinion issued by the European Patent Office for PCT/US2014/012964 dated Jun. 11, 2014; 16 pgs.
International Preliminary Report on Patentability issued by the International Bureau of WIPO for PCT/US2014/012964; dated Aug. 6, 2015; 10 pgs.
Aagaard,"The 30-million-year-old ERVPb1 envelope gene is evolutionarily conserved among hominoids and Old World monkeys," *Genomics*, Dec. 2005;86(6):685-691.
Anthony, The Human Endogenous Retrovirus Envelope Glycoprotein, Syncytin-1, Regulates Neuroinflammation and Its Receptor Expression in Multiple Sclerosis: A Role for Endoplasmic Reticulum Chaperones in Astrocytes, *J Immunol*, Jul. 15, 2007;179(2):1210-1224.
Bieging, "Deconstructing p53 transcriptional networks in tumor suppression" Published online Dec. 9, 2011. doi: 10.1016/j.tcb.2011.10.006.
Castedo,"The cell cycle checkpoint kinase Chk2 is a negative regulator of mitotic catastrophe," *Oncogene*, May 27, 2004;23(25):4353-4361.
De Parseval,"Survey of Human Genes of Retroviral Origin: Identification and Transcriptome of the Genes with Coding Capacity for Complete Envelope Proteins," *J Virol*, Oct. 2003;77(19):10414-10422.
El-Deiry,"Definition of a consensus binding site for p53", *Nat Genet*, Apr. 1992;1(1):45-49.
Funk,"A transcriptionally active DNA-binding site for human p53 protein complexes," *Mol Cell Biol*, Jun. 1992; 12(6):2866-2871.
Haraguchi,"A potent immunosuppressive retroviral peptide: cytokine patterns and signaling pathways," *Immunologic Research*, May 1, 2008;41(1):46-55.
Jordan,"Low-level p53 expression changes transactivation rules and reveals superactiviating sequences," *PNAS USA*, Sep. 4, 2012;109(36):14387-14392.
Jordan,"Noncanonical DNA Motifs as Transactivation targets by Wild Type and Mutant p53," *PLoS Genet*, Jun. 27, 2008;4(6):e1000104.
Jurka,"Repbase Update, a database of eukaryotic repetitive elements," *Cytogentic and Genome Research*, 2005;110:462-467.
Kichina,"Melanoma cells can tolerate high levels of transcriptionally active endogenous p53 but are sensitive to retrovirus-transduced p53," *Oncogene*, Jul. 31, 2003;22(31):4911-4917.
Lin, "Fusogenic membrane glycoproteins induce syncytia formation and death in vitro and in vivo: a potential therapy agent for lung cancer," *Cancer Gene Ther*, Apr. 2010;17(4):256-265.
MacLeod, "p53-dependent and independent expression of p21 during cell growth, differentiation, and DNA damage," *Genes Dev*, Apr. 15, 1995;9(8):935-944.
Ribet, "An infectious progenitor for the murine IAP retrotransposon: Emergence of an intracellular genetic parasite from an ancient retrovirus" Published online in advance: Feb. 6, 2008, doi: 10.1101/gr.073486.107.
Rothmann, "Synthetic peptide homologous to the envelope proteins of retroviruses shares a cross-reacting epitope with the CD4 receptor," *J Clin Microbiol*, Jan. 1, 1990;112-115.
Shono, "Apoptosis induced by adenovirus-mediated p53 gene transfer in human glioma correlates with site-specific phosphorylation," *Cancer Research*, Feb. 1, 2002;62(4):1069-1076.
Spector, "Redistribution of U-snRNPs during Mitosis" 1986 *Exp Cell Res*,163:87-94.
Veprintsev, "Algorithm for prediction of tumour suppressor p53 affinity for binding sites in DNA" Published online Jan. 30, 2008, doi: 10.1093/nar/gkm1040.
Vousden, "Functions of p53 in Metabolism and Invasion," *Biochem Soc Trans*, Jun. 2009;37(part 3):511-517.
Wang, "Species-Specific endogenous retroviruses shape the transcriptional network of the human tumor suppressor protein p53," *PNAS USA*, Nov. 20, 2007;104(47):18613-18618.
Wang-Johanning,"Immunotherapeutic Ptoential of Anti-Human Endogenous Retrovirus-K Envelope Protein Antiodies in Targeting Breast Tumors," *JNCI Journal of the Natl Cancer Inst*, Jan. 12, 2012;104(3):189-210.
Weinberg, "Comparative Binding of p53 to its Promoter and DNA Recognition Elements," *J Mol Biol*, May 6, 2005;384(3):589-596.

* cited by examiner

Fig. 3

5' LTR of HERV-W (SEQ ID NO:2)

TGAGAGACAGGACTAGCT■GATTTCCTAGGCCGACTAAGAATCCCTAAG■TA■C
TGGGAAGGTGACCACGTCCACCTTTAAACACGGGGCTTGC■CTTAGCTCACACC
TGACCAATCAGAGAGCTCACTAAAATGCTAATTAGGCAAAGACAGGAGGTAAAGAA
ATAGCCAATCATCTATTGCCTGAGAGCACAGCAGGAGGGACAACAATCGGGATAT
AAACCCAGGCATTCGAGCTGGCAACAGCAGCCCCCCTTTGGGTCCCTTCCCTTTG
TATGGGAGCTGTTTTCATGCTATTTCACTCTATTAAATCTTGCAACTGCACTCTTCT
GG■CATGTTTCTTACGGCTCGAGCTGAGCTTTTGCTCACCGTCCACCACTGCTGT
TTGCCACCACCGCAGACCTGCCGCGTGACTCCCATCCCTCTGGATCCTGCAGGGTG
TCCGCTGTGCTCCTGATCCAGCGAGGCGCCCATTGCCGCTCCCAATTGGGCTAAA
GGCTTGCC■TTGTTCCTGCACGGCTAAGTGCCTGGGTTTGTTCTAATTGAGCTGAA
■ACTAGTC■CTGGGTTCCATGGTTCTCTTCTGTGACCCACGGCTTCTAATAGAACT
ATAACACTTACCACATGG■CAAG■TTCCATTCCTTGGAATCCGTGAGGCCAAGAA
CTCCAGGTCAGAGAATACGAGGCTTGCC■CCATCTTGGAAGCGGCCTGCTACCAT
CTTGGAAGTGGTTCACCACCATCTTGGGAGCTCTGTGAGCAAG■CCCCCCGGTA
ACA

Fig. 4

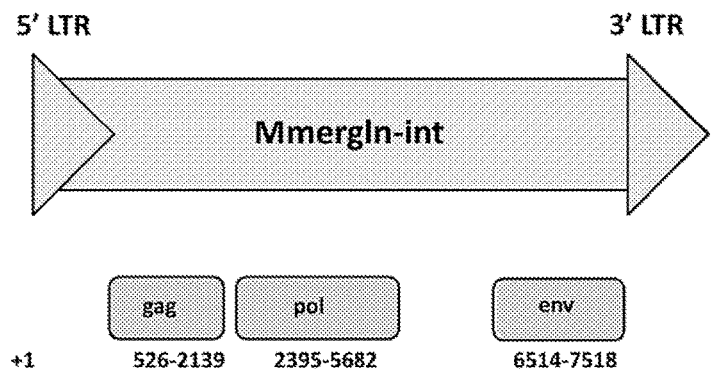

Fig. 12

5' LTR of hERV-FRD LTR (SEQ ID NO:3)

AAGCTGGAAACCACTCTCATGTCCATCAATGAGTAAATGGATAAACAAATTGTGGTATAT
CTATACAATGGAATACTCTTTCAGCAATACAAAAGAATGTATTACTGATATACACAACAC
AAATAGATTTCAAAAGCATTATGCTAGCAGAAAGAAGTCAAACACAAAAAGCATGTTTTG
TGATTTGATTTACATTAGAAAGGTAAATTTATGTTTATGGAAAGCAGTTTGGGCCAGGTG
TGGTGGCTCATGCCTGTAATCCCAGCACTTTGGGAGGCCAAGGACAGCAGATCACTTGAG
GTCAGGAGTTCAAGATCAGCCTGGCCACCATGGTGAAACCTTGTCTCTACTAAAAATACA
AAAATTAGCTGGGCATGTTGTGCACACCTGTTAATTCCAGCTATTCAGGAGTCTGAGGC
ACAAGAATCACTTGAACCCGGGAGGTGGAGGTTGCAGTGAGCCAAGTTGCATCACTGCA
CTCCAGCCTGGGAGACAGAGCGAGGCTGTCTCCAAAAAAAAAAAAGCAAGCTTTCTATC
AGGAGGCCATTAGGTTAAGCTGGTTCTGTTAGAGTAGGTAGTCAGGCAGACATGCCAGG
GCAGGAGAGGGCCCCCAGCTCAGGAATGTCAGGCGACCATCAGGTGATGATCAGGCGGTT
GTTACACTGTTTCTCTAAAATAATAATAATGGGTTGCAGCCAGTACCAGGGAAAGACAGT
CTCCCAAAAGACAGGAAACACCGGAAGCTGGTGATCAGCAACTTCCTGATAAGATCTCCG
AAGCTGGGCAAGTTGCTCAAGCATGCCACTAAGAAGCAAAATGACAGTTTAACCAGTA
TGTGACCTTCCTCTAGGAACACCTGACTGATAAGGGAAAAATGTCTCAAGAAAGCATGC
CACAACTTCAGTAAACAAATGCACATGTGGCTCCTCCCAAGTGCTGACAGGCCACTGCAC
AGCAGACAGCCCACCCCAAGGAAAAAAATCCAAGGAGGAGAAATGGAAACCCCGGAACCA
TGCCGATGTATAAACCCCAAGTCAAGGGCTGAACAGGGCACTTGGATCTCTCAAATGGT
GCAGTGACTCGGATACCTTCCCTAGTGGTAAGACACCTCTAGGCTTGCCTTCTTCGGCT
GGAGGCGTTCAACCCTCGTACGTGGTTTCGTTCTCCTCTTTCACTCTCCTGCTTACTAAC
CTACCCCTGGAACGATTC

SEQUENCE LISTING

<160> NUMBER OF SEQ ID NOS: 125

<210> SEQ ID NO 1
<211> LENGTH: 10
<212> TYPE: DNA
<213> ORGANISM: Mus musculus

<400> SEQUENCE: 1 rrrcwwgyyy                                                                  10

<210> SEQ ID NO 2
<211> LENGTH: 780
<212> TYPE: DNA
<213> ORGANISM: Homo sapiens

<400> SEQUENCE: 2
tgagagacag gactagctgg atttcctagg ccgactaaga atccctaagc ctagctggga      60
aggtgaccac gtccacctttt aaacacgggg cttgcaactt agctcacacc tgaccaatca    120
gagagctcac taaaatgcta attaggcaaa gacaggaggt aaagaaatag ccaatcatct    180
attgcctgag agcacagcag gagggacaac aatcgggata taaacccagg cattcgagct    240
ggcaacagca gccccctttt gggtcccttc cctttgtatg ggagctgttt tcatgctatt    300
tcactctatt aaatcttgca actgcactct tctggtccat gtttcttacg gctcgagctg    360
agcttttgct caccgtccac cactgctgtt tgccaccacc gcagacctgc cgctgactcc    420
catccctctg gatcctgcag ggtgtccgct gtgctcctga tccagcgagg cgcccattgc    480
cgctcccaat tgggctaaag gcttgccatt gttcctgcac ggctaagtgc ctgggtttgt    540
tctaattgag ctgaacacta gtcactgggt tccatggttc tcttctgtga cccacggctt    600
ctaatagaac tataacactt accacatggc ccaagattcc attccttgga atccgtgagg    660
ccaagaactc caggtcagag aatacgaggc ttgccaccat cttggaagcg gcctgctacc    720
atcttggaag tggttcacca ccatcttggg agctctgtga gcaaggaccc cccggtaaca    780

<210> SEQ ID NO 3
<211> LENGTH: 1218
<212> TYPE: DNA
<213> ORGANISM: Homo sapiens

<400> SEQUENCE: 3
aagctggaaa ccactctcat gtccatcaat gagtaaatgg ataaacaaat tgtggtatat       60
ctatacaatg gaatactctt tcagcaatac aaaagaatgt attactgata tacacaacac     120
aaatagattt caaaagcatt atgctagcag aaagaagtca aacacaaaaa gcatgttgtg     180
tgatttgatt tacattagaa aggtaaattt atgtttatgg aaagcagttt gggccaggtg    240

```
tggtggttca tgcctgtaat cccagcactt tgggaggcca aggacagcag atcacttgag    300
gtcaggagtt caagatcagc ctggccacca tggtgaaatc ttgtctctac taaaaataca    360
aaaattagct gggcatggtg gtgcacacct gttaattcca gctattcagg agtctgaggc    420
acaagaatca cttgaacccg ggaggtggag gttgcagtga gccaagattg catcactgca    480
ctccagcctg ggagacagag cgaggctgtc tccaaaaaaa aaaagcaag cagttctatc     540 aggaggccat taggttaagc tggttctgtt agagtaggta gtcaggcaga catgagcagg    600
gcaggagagg gcccccagct caggaatgtc aggcgaccat caggtgatga tcaggcggtt    660
gttacactgt ttctctaaaa taataataat gggttgcagc cagtaccagg aaagacagt     720 ctcccaaaag acaggaaaca ccggaagctg gtgatcagca acttcctgat aagatctccg    780
aagctgggca gtgggctca agcatgcgca ctaagaagca aaatgacagt ttaaccagta     840
tgtgaccttc ctctaggaac acctgactga taagggaaaa atgtctcaag aaagcatgcg    900
cacaacttca gtaaacaaat gcacatgtgg ctcctcccaa gtgctgacag gccactgcac    960
agcagacagc ccaccccaag gaaaaaaatc caaggaggag aaatggaaac cccggaacca    1020
tgccgatgta taaaacccca agtcaagggc tgaacagggc acttggatct ctcaaatggt    1080
gcagtgactc ggataccttc cctagtggta agacacctct acgccttgcc ttcttcggct    1140
ggaggcgttc aaccctcgta cgtggtttcg ttctcctctt tcactctcct gcttactaac    1200 ctaccccctgg aacgattc                                                 1218

<210> SEQ ID NO 4
<211> LENGTH: 20
<212> TYPE: DNA
<213> ORGANISM: Mus musculus

<400> SEQUENCE: 4
ggacatgccc gggcaagccc                                                20

<210> SEQ ID NO 5
<211> LENGTH: 34
<212> TYPE: DNA
<213> ORGANISM: artificial
<220> FEATURE:
<223> OTHER INFORMATION: synthetic oligonucleotide primer

<400> SEQUENCE: 5
ggttccaatg cgcatttgga ggtcccagcg agat                                34

<210> SEQ ID NO 6
<211> LENGTH: 37
<212> TYPE: DNA
<213> ORGANISM: artificial
<220> FEATURE:
<223> OTHER INFORMATION: synthetic oligonucleotide primer

<400> SEQUENCE: 6
ggttccaaac tagtttcccc tcttcttctg tttagac                             37

<210> SEQ ID NO 7
<211> LENGTH: 37
<212> TYPE: DNA
<213> ORGANISM: artificial
<220> FEATURE:
<223> OTHER INFORMATION: synthetic oligonucleotide primer

<400> SEQUENCE: 7
ggttccaaaa gcttatgcct ttattgggga gagactt                             37
```

<210> SEQ ID NO 8
<211> LENGTH: 39
<212> TYPE: DNA
<213> ORGANISM: artificial
<220> FEATURE:
<223> OTHER INFORMATION: synthetic oligonucleotide primer

<400> SEQUENCE: 8
ggttccaagc ggccgctcat tgagtacctc ccacgtttg                   39

<210> SEQ ID NO 9
<211> LENGTH: 36
<212> TYPE: DNA
<213> ORGANISM: artificial
<220> FEATURE:
<223> OTHER INFORMATION: synthetic oligonucleotide primer

<400> SEQUENCE: 9
ggttccaaaa gcttatgatg agtggacttt ggagaa                      36

<210> SEQ ID NO 10
<211> LENGTH: 38
<212> TYPE: DNA
<213> ORGANISM: artificial
<220> FEATURE:
<223> OTHER INFORMATION: synthetic oligonucleotide primer

<400> SEQUENCE: 10
ggttccaagc ggccgcttag aggtcggtgt cccttaac                    38

<210> SEQ ID NO 11
<211> LENGTH: 36
<212> TYPE: DNA
<213> ORGANISM: artificial
<220> FEATURE:
<223> OTHER INFORMATION: synthetic oligonucleotide primer

<400> SEQUENCE: 11
ggttccaaaa gcttatggga cagaccgtgt ctactc                      36

<210> SEQ ID NO 12
<211> LENGTH: 38
<212> TYPE: DNA
<213> ORGANISM: artificial
<220> FEATURE:
<223> OTHER INFORMATION: synthetic oligonucleotide primer

<400> SEQUENCE: 12
ggttccaagc ggccgctagt cttcatcttc tccaagag                    38

<210> SEQ ID NO 13
<211> LENGTH: 22
<212> TYPE: DNA
<213> ORGANISM: artificial
<220> FEATURE:
<223> OTHER INFORMATION: synthetic oligonucleotide primer

<400> SEQUENCE: 13
ggaccaagga gacccagaga ag                                     22

<210> SEQ ID NO 14
<211> LENGTH: 20
<212> TYPE: DNA
<213> ORGANISM: artificial
<220> FEATURE:

<223> OTHER INFORMATION: synthetic oligonucleotide primer

<400> SEQUENCE: 14
cccgtgtcaa ctagaaagtc                                                        20

<210> SEQ ID NO 15
<211> LENGTH: 21
<212> TYPE: DNA
<213> ORGANISM: artificial
<220> FEATURE:
<223> OTHER INFORMATION: synthetic oligonucleotide primer

<400> SEQUENCE: 15
tccgagccaa taacccacag g                                                      21

<210> SEQ ID NO 16
<211> LENGTH: 20
<212> TYPE: DNA
<213> ORGANISM: artificial
<220> FEATURE:
<223> OTHER INFORMATION: synthetic oligonucleotide primer

<400> SEQUENCE: 16
tttagcagag gcccgatacc                                                        20

<210> SEQ ID NO 17
<211> LENGTH: 21
<212> TYPE: DNA
<213> ORGANISM: artificial
<220> FEATURE:
<223> OTHER INFORMATION: synthetic oligonucleotide primer

<400> SEQUENCE: 17
ccacgcatcc cacgttaaga g                                                      21

<210> SEQ ID NO 18
<211> LENGTH: 20
<212> TYPE: DNA
<213> ORGANISM: artificial
<220> FEATURE:
<223> OTHER INFORMATION: synthetic oligonucleotide primer

<400> SEQUENCE: 18
aggccaccaa gtccacagag                                                        20

<210> SEQ ID NO 19
<211> LENGTH: 23
<212> TYPE: DNA
<213> ORGANISM: artificial
<220> FEATURE:
<223> OTHER INFORMATION: synthetic oligonucleotide primer

<400> SEQUENCE: 19
ccaattactt taaccctggc tgc                                                    23

<210> SEQ ID NO 20
<211> LENGTH: 22
<212> TYPE: DNA
<213> ORGANISM: artificial
<220> FEATURE:
<223> OTHER INFORMATION: synthetic oligonucleotide primer

<400> SEQUENCE: 20
gtcgctaggt cttcattgac ag                                                     22

<210> SEQ ID NO 21
<211> LENGTH: 20
<212> TYPE: DNA
<213> ORGANISM: artificial
<220> FEATURE:
<223> OTHER INFORMATION: synthetic oligonucleotide primer

<400> SEQUENCE: 21
tgcaccacca actgcttagc                                               20

<210> SEQ ID NO 22
<211> LENGTH: 21
<212> TYPE: DNA
<213> ORGANISM: artificial
<220> FEATURE:
<223> OTHER INFORMATION: synthetic oligonucleotide primer

<400> SEQUENCE: 22
ggcatggact gtggtcatga g                                             21

<210> SEQ ID NO 23
<211> LENGTH: 23
<212> TYPE: DNA
<213> ORGANISM: artificial
<220> FEATURE:
<223> OTHER INFORMATION: synthetic oligonucleotide primer

<400> SEQUENCE: 23
gtggttttga ttctcctgtg tgc                                           23

<210> SEQ ID NO 24
<211> LENGTH: 19
<212> TYPE: DNA
<213> ORGANISM: artificial
<220> FEATURE:
<223> OTHER INFORMATION: synthetic oligonucleotide primer

<400> SEQUENCE: 24
gccttgtacc catcaggga                                                19

<210> SEQ ID NO 25
<211> LENGTH: 20
<212> TYPE: DNA
<213> ORGANISM: artificial
<220> FEATURE:
<223> OTHER INFORMATION: synthetic oligonucleotide primer

<400> SEQUENCE: 25
ccatgggaag caagggaact                                               20

<210> SEQ ID NO 26
<211> LENGTH: 20
<212> TYPE: DNA
<213> ORGANISM: artificial
<220> FEATURE:
<223> OTHER INFORMATION: synthetic oligonucleotide primer

<400> SEQUENCE: 26
ctttccccag cgagcaatac                                               20

<210> SEQ ID NO 27
<211> LENGTH: 20
<212> TYPE: DNA
<213> ORGANISM: artificial
<220> FEATURE:
<223> OTHER INFORMATION: synthetic oligonucleotide primer

```
<400> SEQUENCE: 27
ccccatcgta taggagtctt                                               20

<210> SEQ ID NO 28
<211> LENGTH: 20
<212> TYPE: DNA
<213> ORGANISM: artificial
<220> FEATURE:
<223> OTHER INFORMATION: synthetic oligonucleotide primer

<400> SEQUENCE: 28
ccccatcaga cataccagtt                                               20

<210> SEQ ID NO 29
<211> LENGTH: 20
<212> TYPE: DNA
<213> ORGANISM: artificial
<220> FEATURE:
<223> OTHER INFORMATION: synthetic oligonucleotide primer

<400> SEQUENCE: 29
tgatggcctc cttggaaacg                                               20

<210> SEQ ID NO 30
<211> LENGTH: 20
<212> TYPE: DNA
<213> ORGANISM: artificial
<220> FEATURE:
<223> OTHER INFORMATION: synthetic oligonucleotide primer

<400> SEQUENCE: 30
caggtgtagc cagtgtagcc                                               20

<210> SEQ ID NO 31
<211> LENGTH: 20
<212> TYPE: DNA
<213> ORGANISM: artificial
<220> FEATURE:
<223> OTHER INFORMATION: synthetic oligonucleotide primer

<400> SEQUENCE: 31
ctctgaggag ggattcccca                                               20

<210> SEQ ID NO 32
<211> LENGTH: 20
<212> TYPE: DNA
<213> ORGANISM: artificial
<220> FEATURE:
<223> OTHER INFORMATION: synthetic oligonucleotide primer

<400> SEQUENCE: 32
agtcaagtta gggtggcagc                                               20

<210> SEQ ID NO 33
<211> LENGTH: 21
<212> TYPE: DNA
<213> ORGANISM: artificial
<220> FEATURE:
<223> OTHER INFORMATION: synthetic oligonucleotide primer

<400> SEQUENCE: 33
gggccactaa gttactaggt c                                             21

<210> SEQ ID NO 34
<211> LENGTH: 21
```

```
<212> TYPE: DNA
<213> ORGANISM: artificial
<220> FEATURE:
<223> OTHER INFORMATION: synthetic oligonucleotide primer

<400> SEQUENCE: 34
agttaggagg gagttactgg g                                             21

<210> SEQ ID NO 35
<211> LENGTH: 20
<212> TYPE: DNA
<213> ORGANISM: artificial
<220> FEATURE:
<223> OTHER INFORMATION: synthetic oligonucleotide primer

<400> SEQUENCE: 35
gcctgcaaat agtcttcttt                                               20

<210> SEQ ID NO 36
<211> LENGTH: 20
<212> TYPE: DNA
<213> ORGANISM: artificial
<220> FEATURE:
<223> OTHER INFORMATION: synthetic oligonucleotide primer

<400> SEQUENCE: 36 atagggcta ttcccattag                                                20

<210> SEQ ID NO 37
<211> LENGTH: 20
<212> TYPE: DNA
<213> ORGANISM: artificial
<220> FEATURE:
<223> OTHER INFORMATION: synthetic oligonucleotide primer

<400> SEQUENCE: 37
ggacagtgcc gacatactat                                               20

<210> SEQ ID NO 38
<211> LENGTH: 20
<212> TYPE: DNA
<213> ORGANISM: artificial
<220> FEATURE:
<223> OTHER INFORMATION: synthetic oligonucleotide primer

<400> SEQUENCE: 38
tagagtgcag catcctaacc                                               20

<210> SEQ ID NO 39
<211> LENGTH: 23
<212> TYPE: DNA
<213> ORGANISM: artificial
<220> FEATURE:
<223> OTHER INFORMATION: synthetic oligonucleotide primer

<400> SEQUENCE: 39
actacacaca tcactgaaac aaa                                           23

<210> SEQ ID NO 40
<211> LENGTH: 21
<212> TYPE: DNA
<213> ORGANISM: artificial
<220> FEATURE:
<223> OTHER INFORMATION: synthetic oligonucleotide primer

<400> SEQUENCE: 40
```

```
ggatggagtg aaatacagga c                                          21

<210> SEQ ID NO 41
<211> LENGTH: 20
<212> TYPE: DNA
<213> ORGANISM: artificial
<220> FEATURE:
<223> OTHER INFORMATION: synthetic oligonucleotide primer

<400> SEQUENCE: 41
ttcactccat ccttggctat                                            20

<210> SEQ ID NO 42
<211> LENGTH: 21
<212> TYPE: DNA
<213> ORGANISM: artificial
<220> FEATURE:
<223> OTHER INFORMATION: synthetic oligonucleotide primer

<400> SEQUENCE: 42
cgtcgagtat ctacgagcaa t                                          21

<210> SEQ ID NO 43
<211> LENGTH: 20
<212> TYPE: DNA
<213> ORGANISM: artificial
<220> FEATURE:
<223> OTHER INFORMATION: synthetic oligonucleotide primer

<400> SEQUENCE: 43
cacaactaaa gaagctgacg                                            20

<210> SEQ ID NO 44
<211> LENGTH: 20
<212> TYPE: DNA
<213> ORGANISM: artificial
<220> FEATURE:
<223> OTHER INFORMATION: synthetic oligonucleotide primer

<400> SEQUENCE: 44
cataggccca gttggtatag                                            20

<210> SEQ ID NO 45
<211> LENGTH: 18
<212> TYPE: DNA
<213> ORGANISM: artificial
<220> FEATURE:
<223> OTHER INFORMATION: synthetic oligonucleotide primer

<400> SEQUENCE: 45
ccaggatttg atgttggg                                              18

<210> SEQ ID NO 46
<211> LENGTH: 21
<212> TYPE: DNA
<213> ORGANISM: artificial
<220> FEATURE:
<223> OTHER INFORMATION: synthetic oligonucleotide primer

<400> SEQUENCE: 46
ggggtgaggt taaggagatg g                                          21

<210> SEQ ID NO 47
<211> LENGTH: 26
<212> TYPE: DNA
<213> ORGANISM: artificial
```

```
<220> FEATURE:
<223> OTHER INFORMATION: synthetic oligonucleotide primer

<400> SEQUENCE: 47
ggttccaact cgagtgaaag gaaata                                            26

<210> SEQ ID NO 48
<211> LENGTH: 26
<212> TYPE: DNA
<213> ORGANISM: artificial
<220> FEATURE:
<223> OTHER INFORMATION: synthetic oligonucleotide primer

<400> SEQUENCE: 48
ggttccaaaa gctttgaaag aactca                                            26

<210> SEQ ID NO 49
<211> LENGTH: 32
<212> TYPE: DNA
<213> ORGANISM: artificial
<220> FEATURE:
<223> OTHER INFORMATION: synthetic oligonucleotide primer

<400> SEQUENCE: 49
atagcagaac agaccaatcg cctccctagc tc                                     32

<210> SEQ ID NO 50
<211> LENGTH: 32
<212> TYPE: DNA
<213> ORGANISM: artificial
<220> FEATURE:
<223> OTHER INFORMATION: synthetic oligonucleotide primer

<400> SEQUENCE: 50
gagctaggga ggcgattggt ctgttctgct at                                     32

<210> SEQ ID NO 51
<211> LENGTH: 29
<212> TYPE: DNA
<213> ORGANISM: artificial
<220> FEATURE:
<223> OTHER INFORMATION: synthetic oligonucleotide primer

<400> SEQUENCE: 51
agaacagacc aggaaatgcc cgggcaagc                                         29

<210> SEQ ID NO 52
<211> LENGTH: 29
<212> TYPE: DNA
<213> ORGANISM: artificial
<220> FEATURE:
<223> OTHER INFORMATION: synthetic oligonucleotide primer

<400> SEQUENCE: 52
gcttgcccgg gcatttcctg gtctgttct                                         29

<210> SEQ ID NO 53
<211> LENGTH: 25
<212> TYPE: DNA
<213> ORGANISM: artificial
<220> FEATURE:
<223> OTHER INFORMATION: synthetic oligonucleotide primer

<400> SEQUENCE: 53
gacatgcccg ggaaagccca tcgcc                                             25
```

```
<210> SEQ ID NO 54
<211> LENGTH: 25
<212> TYPE: DNA
<213> ORGANISM: artificial
<220> FEATURE:
<223> OTHER INFORMATION: synthetic oligonucleotide primer

<400> SEQUENCE: 54
ggcgatgggc tttcccgggc atgtc                                           25

<210> SEQ ID NO 55
<211> LENGTH: 33
<212> TYPE: DNA
<213> ORGANISM: artificial
<220> FEATURE:
<223> OTHER INFORMATION: synthetic oligonucleotide primer

<400> SEQUENCE: 55
acagaccagg aaatgcccgg gaaagcccat cgc                                  33

<210> SEQ ID NO 56
<211> LENGTH: 33
<212> TYPE: DNA
<213> ORGANISM: artificial
<220> FEATURE:
<223> OTHER INFORMATION: synthetic oligonucleotide primer

<400> SEQUENCE: 56
gcgatgggct ttcccgggca tttcctggtc tgt                                  33

<210> SEQ ID NO 57
<211> LENGTH: 24
<212> TYPE: DNA
<213> ORGANISM: artificial
<220> FEATURE:
<223> OTHER INFORMATION: synthetic oligonucleotide primer

<400> SEQUENCE: 57
gctgagaaca tagcagaaca gacc                                            24

<210> SEQ ID NO 58
<211> LENGTH: 24
<212> TYPE: DNA
<213> ORGANISM: artificial
<220> FEATURE:
<223> OTHER INFORMATION: synthetic oligonucleotide primer

<400> SEQUENCE: 58
gcacccaaga atcacgaata gaac                                            24

<210> SEQ ID NO 59
<211> LENGTH: 23
<212> TYPE: DNA
<213> ORGANISM: artificial
<220> FEATURE:
<223> OTHER INFORMATION: synthetic oligonucleotide primer

<400> SEQUENCE: 59
aacaggagac agtggattcg acc                                             23

<210> SEQ ID NO 60
<211> LENGTH: 25
<212> TYPE: DNA
<213> ORGANISM: artificial
<220> FEATURE:
<223> OTHER INFORMATION: synthetic oligonucleotide primer
```

-continued

```
<400> SEQUENCE: 60
ggtgcctggt cccggactcg ccggg                                                25

<210> SEQ ID NO 61
<211> LENGTH: 25
<212> TYPE: DNA
<213> ORGANISM: artificial
<220> FEATURE:
<223> OTHER INFORMATION: synthetic oligonucleotide primer

<400> SEQUENCE: 61
ccgagagggt cccccagggg tgtcc                                                25

<210> SEQ ID NO 62
<211> LENGTH: 26
<212> TYPE: DNA
<213> ORGANISM: artificial
<220> FEATURE:
<223> OTHER INFORMATION: synthetic oligonucleotide primer

<400> SEQUENCE: 62
cctttctatc agccccagag gatacc                                               26

<210> SEQ ID NO 63
<211> LENGTH: 25
<212> TYPE: DNA
<213> ORGANISM: artificial
<220> FEATURE:
<223> OTHER INFORMATION: synthetic oligonucleotide primer

<400> SEQUENCE: 63
gggacgtcct taattatctg gggtc                                                25

<210> SEQ ID NO 64
<211> LENGTH: 25
<212> TYPE: DNA
<213> ORGANISM: artificial
<220> FEATURE:
<223> OTHER INFORMATION: synthetic oligonucleotide primer

<400> SEQUENCE: 64
gatgttgtag ccaccgcgta cagcc                                                25

<210> SEQ ID NO 65
<211> LENGTH: 25
<212> TYPE: DNA
<213> ORGANISM: artificial
<220> FEATURE:
<223> OTHER INFORMATION: synthetic oligonucleotide primer

<400> SEQUENCE: 65
ttcatggtag agagcactaa ggagg                                                25

<210> SEQ ID NO 66
<211> LENGTH: 650
<212> TYPE: PRT
<213> ORGANISM: Mus musculus

<400> SEQUENCE: 66

Met Met Ser Gly Leu Trp Arg Arg Leu Leu Ile Leu Leu Ser Cys Ala
1               5                   10                  15

Cys Phe Val Gly Ala Ile Pro Lys Asp Phe Asn Pro His Ser Pro Val
            20                  25                  30
```

-continued

```
Gln Gln Thr Trp Glu Val Leu Asn Glu Glu Gly Arg Ala Val Trp Thr
         35                  40                  45

Ile Ala Glu Val His Pro Leu Trp Thr Trp Pro Asp Leu Phe Pro
 50                  55                  60

Asp Ile Cys Lys Leu Ala Ile Gly Ala Pro Pro Gly Trp Asp Leu Glu
 65                  70                  75                  80

Gly Tyr Ser Asp Ile Gln Arg Ala Pro Leu Thr Pro Pro Tyr Val
                 85                  90                  95

Glu Lys His Leu Arg Asp Pro Trp Gly Gly Cys Ser Asn Gln Arg Asp
             100                 105                 110

Arg Ser Met Leu Arg Thr His Pro Phe Tyr Val Cys Pro Gly Pro His
         115                 120                 125

Gln Ser Gln Ser Leu Asn Pro Thr Cys Gly Gly Lys Ala Asp Phe Phe
 130                 135                 140

Cys Lys Ser Trp Gly Cys Glu Thr Ser Gly Thr Ala Arg Trp Lys Pro
145                 150                 155                 160

Ser Ser Ser Trp Asp Tyr Ile Arg Val Thr Ala Asn Tyr Ser Leu Ala
                 165                 170                 175

Ser Tyr Val Pro Gly Gly Phe Asp Leu Asp Glu Cys Thr Asp Trp Cys
             180                 185                 190

His Pro Leu Arg Val Thr Phe Thr Glu Pro Gly Lys Arg Ala Leu Gly
         195                 200                 205

Trp Thr Arg Gly Tyr Thr Trp Gly Leu Arg Ile Tyr Lys Glu Arg Tyr
210                 215                 220

Asp Glu Gly Leu Leu Phe Thr Ile Arg Leu Lys Ile Glu Thr Pro Tyr
225                 230                 235                 240

Asn Pro Leu Gly Pro Pro Thr Lys Phe Thr Pro Leu Thr His Thr Ile
                 245                 250                 255

Thr Gln Pro Thr Pro Val Ile Ala Asp Pro Leu Asn Met Ala Ala Ile
             260                 265                 270

Thr Gln Pro Pro Thr Pro Gln Val Pro Leu Thr Ile Thr Pro Thr Ile
         275                 280                 285

Pro Ser Arg Gln Arg Met Phe Asn Leu Val Arg Gly Ala Phe Tyr Ala
290                 295                 300

Leu Asn Arg Thr Asp Pro Ser Ala Thr Glu Asp Cys Trp Leu Cys Leu
305                 310                 315                 320

Ser Ser Gly Pro Pro Tyr Tyr Glu Gly Ile Ala Phe Asn Gly Asp Phe
                 325                 330                 335

Asn Arg Ile Ser Ser His Thr Ser Cys Ser Trp Gly Thr Gly Gln Lys
             340                 345                 350

Leu Thr Leu Thr Glu Val Ser Val Arg Asn Pro Gly Leu Cys Ile Gly
         355                 360                 365

Thr Pro Pro Ser Thr His Lys His Leu Cys Gly Gln Ile Gln Ser Met
370                 375                 380

Ser Arg Thr Glu Ala Asn Tyr Tyr Leu Val Pro Ser Pro Val Gly Trp
385                 390                 395                 400

Trp Ala Cys Asn Thr Gly Leu Thr Pro Cys Val Ser Thr Lys Val Phe
                 405                 410                 415

Asn Ser Ser His Asp Phe Cys Val Met Ile Gln Leu Leu Pro His Val
             420                 425                 430

Tyr Tyr His Pro Ala Ser Ser Leu Glu Glu Ser Tyr Ala Gly Arg Arg
         435                 440                 445

Ser Lys Arg Glu Pro Thr Thr Leu Thr Leu Ala Ala Phe Met Gly Ile
```

```
                450                 455                 460
Gly Met Ala Val Gly Val Gly Thr Gly Val Ser Ala Leu Ile Glu Gly
465                 470                 475                 480

Arg Gln Gly Ile Gln Ser Leu Arg Asp Ala Val Asn Glu Asp Leu Ala
                485                 490                 495

Ala Ile Glu Lys Ser Ile Asp Ala Leu Lys Lys Ser Leu Thr Ser Leu
                500                 505                 510

Ser Glu Val Val Leu Gln Asn Arg Arg Gly Leu Asp Leu Leu Phe Leu
                515                 520                 525

Lys Glu Gly Gly Leu Cys Ala Ala Leu Lys Glu Glu Cys Cys Phe Tyr
530                 535                 540

Ala Asp His Thr Gly Ile Val Arg Asp Ser Met Gln Lys Leu Arg Glu
545                 550                 555                 560

Lys Leu Glu Arg Arg Lys Pro Glu Arg Asp Ala Gln Arg Gly Trp Phe
                565                 570                 575

Glu Ser Trp Phe Glu Ser Arg Pro Ser Trp Ile Thr Ser Leu Ile Ser
                580                 585                 590

Ala Val Ala Gly Pro Ile Leu Met Ile Cys Leu Ala Leu Val Phe Ser
                595                 600                 605

Pro Cys Ile Ile Asn Arg Gly Met Ala Phe Ile Gln Ser Lys Ile Asp
                610                 615                 620

Thr Val Lys Leu Met Val Leu Gln Arg Gln Tyr Gln Pro Ile Val Gln
625                 630                 635                 640

Val Asp Glu Glu Leu Gly Asp Thr Asn Leu
                645                 650

<210> SEQ ID NO 67
<211> LENGTH: 538
<212> TYPE: PRT
<213> ORGANISM: Homo sapiens

<400> SEQUENCE: 67

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
                20                  25                  30

Pro Tyr Gln Glu Phe Leu Trp Arg Met Gln Arg Pro Gly Asn Ile Asp
                35                  40                  45

Ala Pro Ser Tyr Arg Ser Leu Ser Lys Gly Thr Pro Thr Phe Thr Ala
                50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
                100                 105                 110

Gly Met Ser Asp Gly Gly Val Gln Asp Gln Ala Arg Glu Lys His
                115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175
```

```
Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
        210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
        290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Val Leu Gln Asn Arg Arg
370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
        450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
530                 535

<210> SEQ ID NO 68
<211> LENGTH: 538
<212> TYPE: PRT
<213> ORGANISM: Homo sapiens

<400> SEQUENCE: 68

Met Gly Leu Leu Leu Leu Val Leu Ile Leu Thr Pro Ser Leu Ala Ala
1               5                   10                  15
```

```
Tyr Arg His Pro Asp Phe Pro Leu Leu Glu Lys Ala Gln Gln Leu Leu
            20                  25                  30

Gln Ser Thr Gly Ser Pro Tyr Ser Thr Asn Cys Trp Leu Cys Thr Ser
        35                  40                  45

Ser Ser Thr Glu Thr Pro Gly Thr Ala Tyr Pro Ala Ser Pro Arg Glu
50                  55                  60

Trp Thr Ser Ile Glu Ala Glu Leu His Ile Ser Tyr Arg Trp Asp Pro
65                  70                  75                  80

Asn Leu Lys Gly Leu Met Arg Pro Ala Asn Ser Leu Leu Ser Thr Val
                85                  90                  95

Lys Gln Asp Phe Pro Asp Ile Arg Gln Lys Pro Pro Ile Phe Gly Pro
                100                 105                 110

Ile Phe Thr Asn Ile Asn Leu Met Gly Ile Ala Pro Ile Cys Val Met
            115                 120                 125

Ala Lys Arg Lys Asn Gly Thr Asn Val Gly Thr Leu Pro Ser Thr Val
130                 135                 140

Cys Asn Val Thr Phe Thr Val Asp Ser Asn Gln Gln Thr Tyr Gln Thr
145                 150                 155                 160

Tyr Thr His Asn Gln Phe Arg His Gln Pro Arg Phe Pro Lys Pro Pro
                165                 170                 175

Asn Ile Thr Phe Pro Gln Gly Thr Leu Leu Asp Lys Ser Ser Arg Phe
            180                 185                 190

Cys Gln Gly Arg Pro Ser Ser Cys Ser Thr Arg Asn Phe Trp Phe Arg
            195                 200                 205

Pro Ala Asp Tyr Asn Gln Cys Leu Gln Ile Ser Asn Leu Ser Ser Thr
            210                 215                 220

Ala Glu Trp Val Leu Leu Asp Gln Thr Arg Asn Ser Leu Phe Trp Glu
225                 230                 235                 240

Asn Lys Thr Lys Gly Ala Asn Gln Ser Gln Thr Pro Cys Val Gln Val
                245                 250                 255

Leu Ala Gly Met Thr Ile Ala Thr Ser Tyr Leu Gly Ile Ser Ala Val
                260                 265                 270

Ser Glu Phe Phe Gly Thr Ser Leu Thr Pro Leu Phe His Phe His Ile
            275                 280                 285

Ser Thr Cys Leu Lys Thr Gln Gly Ala Phe Tyr Ile Cys Gly Gln Ser
            290                 295                 300

Ile His Gln Cys Leu Pro Ser Asn Trp Thr Gly Thr Cys Thr Ile Gly
305                 310                 315                 320

Tyr Val Thr Pro Asp Ile Phe Ile Ala Pro Gly Asn Leu Ser Leu Pro
                325                 330                 335

Ile Pro Ile Tyr Gly Asn Ser Pro Leu Pro Arg Val Arg Arg Ala Ile
            340                 345                 350

His Phe Ile Pro Leu Leu Ala Gly Leu Gly Ile Leu Ala Gly Thr Gly
            355                 360                 365

Thr Gly Ile Ala Gly Ile Thr Lys Ala Ser Leu Thr Tyr Ser Gln Leu
            370                 375                 380

Ser Lys Glu Ile Ala Asn Asn Ile Asp Thr Met Ala Lys Ala Leu Thr
385                 390                 395                 400

Thr Met Gln Glu Gln Ile Asp Ser Leu Ala Ala Val Val Leu Gln Asn
                405                 410                 415

Arg Arg Gly Leu Asp Met Leu Thr Ala Ala Gln Gly Gly Ile Cys Leu
                420                 425                 430
```

```
Ala Leu Asp Glu Lys Cys Cys Phe Trp Val Asn Gln Ser Gly Lys Val
            435                 440                 445

Gln Asp Asn Ile Arg Gln Leu Leu Asn Gln Ala Ser Ser Leu Arg Glu
    450                 455                 460

Arg Ala Thr Gln Gly Trp Leu Asn Trp Glu Gly Thr Trp Lys Trp Phe
465                 470                 475                 480

Ser Trp Val Leu Pro Leu Thr Gly Pro Leu Val Ser Leu Leu Leu Leu
            485                 490                 495

Leu Leu Phe Gly Pro Cys Leu Leu Asn Leu Ile Thr Gln Phe Val Ser
            500                 505                 510

Ser Arg Leu Gln Ala Ile Lys Leu Gln Thr Asn Leu Ser Ala Gly Arg
            515                 520                 525

His Pro Arg Asn Ile Gln Glu Ser Pro Phe
    530                 535

<210> SEQ ID NO 69
<211> LENGTH: 584
<212> TYPE: PRT
<213> ORGANISM: Homo sapiens

<400> SEQUENCE: 69

Met Ala Arg Pro Ser Pro Leu Cys Leu Leu Leu Leu Thr Leu Thr Leu
1               5                   10                  15

Thr Pro Ile Val Pro Ser Asn Ser Leu Leu Thr Glu Pro Pro Phe Arg
            20                  25                  30

Trp Arg Phe Tyr Leu His Glu Thr Trp Thr Gln Gly Asn Arg Leu Ser
        35                  40                  45

Thr Val Thr Leu Ala Thr Val Asp Cys Gln Pro His Gly Cys Gln Ala
    50                  55                  60

Gln Val Thr Phe Asn Phe Thr Ser Phe Lys Ser Val Leu Arg Gly Trp
65                  70                  75                  80

Ser Asn Pro Thr Ile Cys Phe Val Tyr Asp Gln Thr His Ser Asn Cys
                85                  90                  95

Arg Asp Tyr Trp Val Asp Thr Asn Gly Gly Cys Pro Tyr Ala Tyr Cys
            100                 105                 110

Arg Met His Val Thr Gln Leu His Thr Ala Lys Lys Leu Gln His Thr
        115                 120                 125

Tyr Arg Leu Thr Ser Asp Gly Arg Thr Thr Tyr Phe Leu Thr Ile Pro
    130                 135                 140

Asp Pro Trp Asp Ser Arg Trp Val Ser Gly Val Thr Gly Arg Leu Tyr
145                 150                 155                 160

Arg Trp Pro Thr Asp Ser Tyr Pro Val Gly Lys Leu Arg Ile Phe Leu
                165                 170                 175

Thr Tyr Ile Arg Val Ile Pro Gln Val Leu Ser Asn Leu Lys Asp Gln
            180                 185                 190

Ala Asp Asn Ile Lys His Gln Glu Glu Val Ile Asn Thr Leu Val Gln
        195                 200                 205

Ser His Pro Lys Ala Asp Met Val Thr Tyr Asp Lys Ala Glu Ala
    210                 215                 220

Gly Pro Phe Ser Trp Ile Thr Leu Val Arg His Gly Ala Arg Leu Val
225                 230                 235                 240

Asn Met Ala Gly Leu Val Asn Leu Ser His Cys Phe Leu Cys Thr Ala
                245                 250                 255

Leu Ser Gln Pro Pro Leu Val Ala Val Pro Leu Pro Gln Ala Phe Asn
            260                 265                 270
```

Thr Ser Gly Asn His Thr Ala His Pro Ser Gly Val Phe Ser Glu Gln
            275                 280                 285

Val Pro Leu Phe Arg Asp Pro Leu Gln Pro Gln Phe Pro Phe Cys Tyr
290                 295                 300

Thr Thr Pro Asn Ser Ser Trp Cys Asn Gln Thr Tyr Ser Gly Ser Leu
305                 310                 315                 320

Ser Asn Leu Ser Ala Pro Ala Gly Gly Tyr Phe Trp Cys Asn Phe Thr
            325                 330                 335

Leu Thr Lys His Leu Asn Ile Ser Ser Asn Asn Thr Leu Ser Arg Asn
            340                 345                 350

Leu Cys Leu Pro Ile Ser Leu Val Pro Arg Leu Thr Leu Tyr Ser Glu
            355                 360                 365

Ala Glu Leu Ser Ser Leu Val Asn Pro Pro Met Arg Gln Lys Arg Ala
370                 375                 380

Val Phe Pro Pro Leu Val Ile Gly Val Ser Leu Thr Ser Ser Leu Val
385                 390                 395                 400

Ala Ser Gly Leu Gly Thr Gly Ala Ile Val His Phe Ile Ser Ser Ser
            405                 410                 415

Gln Asp Leu Ser Ile Lys Leu Gln Met Ala Ile Glu Ala Ser Ala Glu
            420                 425                 430

Ser Leu Ala Ser Leu Gln Arg Gln Ile Thr Ser Val Ala Lys Val Ala
            435                 440                 445

Met Gln Asn Arg Arg Ala Leu Asp Leu Leu Thr Ala Asp Lys Gly Gly
450                 455                 460

Thr Cys Met Phe Leu Gly Glu Glu Cys Cys Tyr Tyr Ile Asn Glu Ser
465                 470                 475                 480

Gly Leu Val Glu Thr Ser Leu Leu Thr Leu Asp Lys Ile Arg Asp Gly
            485                 490                 495

Leu His Arg Pro Ser Ser Thr Pro Asn Tyr Gly Gly Gly Trp Trp Gln
            500                 505                 510

Ser Pro Leu Thr Thr Trp Ile Ile Pro Phe Ile Ser Pro Ile Leu Ile
            515                 520                 525

Ile Cys Leu Leu Leu Leu Ile Ala Pro Cys Val Leu Lys Phe Ile Lys
            530                 535                 540

Asn Arg Ile Ser Glu Val Ser Arg Val Thr Val Asn Gln Met Leu Leu
545                 550                 555                 560

His Pro Tyr Ser Arg Leu Pro Thr Ser Glu Asp His Tyr Asp Asp Ala
            565                 570                 575

Leu Thr Gln Gln Glu Ala Ala Arg
            580

<210> SEQ ID NO 70
<211> LENGTH: 526
<212> TYPE: PRT
<213> ORGANISM: Homo sapiens

<400> SEQUENCE: 70

Met Asn Ser Pro Cys Asp Arg Leu Gln Gln Phe Ile Gln Val Leu Leu
1               5                   10                  15

Glu Glu Ser Trp Ser Phe Pro Ser Phe Ala Asn Thr Leu His Trp Pro
            20                  25                  30

Glu Asn Leu Leu Ser Tyr Ile Asp Glu Leu Val Trp Gln Gly Ser Leu
            35                  40                  45

Gln Asn Phe His Gln His Glu Val Arg Phe Asp Lys Pro Pro Leu Leu

```
            50                  55                  60
Pro Leu Thr Gly Phe Ser Ser Leu Thr Glu Asn Trp Ser Ser Arg Gln
65                  70                  75                  80

Ala Val Ser Ser Arg Leu Val Ala Thr Ala Ala Ser Pro Pro Ala Gly
                85                  90                  95

Cys Gln Ala Pro Ile Ala Phe Leu Gly Leu Lys Phe Ser Ser Leu Gly
            100                 105                 110

Pro Ala Arg Lys Asn Pro Ala Leu Cys Phe Leu Tyr Asp Gln Ser Asn
        115                 120                 125

Ser Lys Cys Asn Thr Ser Trp Val Lys Glu Asn Val Gly Cys Pro Trp
130                 135                 140

His Trp Cys Asn Ile His Glu Ala Leu Ile Arg Thr Glu Lys Gly Ser
145                 150                 155                 160

Asp Pro Met Phe Tyr Val Asn Thr Ser Thr Gly Gly Arg Asp Gly Phe
                165                 170                 175

Asn Gly Phe Asn Leu Gln Ile Ser Asp Pro Trp Asp Pro Arg Trp Ala
            180                 185                 190

Ser Gly Val Asp Gly Gly Leu Tyr Glu His Lys Thr Phe Met Tyr Pro
        195                 200                 205

Val Ala Lys Ile Arg Ile Ala Arg Thr Leu Lys Thr Thr Val Thr Gly
210                 215                 220

Leu Ser Asp Leu Ala Ser Ser Ile Gln Ser Ala Glu Lys Glu Leu Thr
225                 230                 235                 240

Ser Gln Leu Gln Pro Ala Ala Asp Gln Ala Lys Ser Ser Arg Phe Ser
                245                 250                 255

Trp Leu Thr Leu Ile Ser Glu Gly Ala Gln Leu Leu Gln Ser Thr Gly
            260                 265                 270

Val Gln Asn Leu Ser His Cys Phe Leu Cys Ala Ala Leu Arg Arg Pro
        275                 280                 285

Pro Leu Val Ala Val Pro Leu Pro Thr Pro Phe Asn Tyr Thr Ile Asn
290                 295                 300

Ser Ser Thr Pro Ile Pro Pro Val Pro Lys Gly Gln Val Pro Leu Phe
305                 310                 315                 320

Ser Asp Pro Ile Arg His Lys Phe Pro Phe Cys Tyr Ser Thr Pro Asn
                325                 330                 335

Ala Ser Trp Cys Asn Gln Thr Arg Met Leu Thr Ser Thr Pro Ala Pro
            340                 345                 350

Pro Arg Gly Tyr Phe Trp Cys Asn Ser Thr Leu Thr Lys Val Leu Asn
        355                 360                 365

Ser Thr Gly Asn His Thr Leu Cys Leu Pro Ile Ser Leu Ile Pro Gly
370                 375                 380

Leu Thr Leu Tyr Ser Gln Asp Glu Leu Ser His Leu Leu Ala Trp Thr
385                 390                 395                 400

Glu Pro Arg Pro Gln Asn Lys Ser Lys Trp Ala Ile Phe Leu Pro Leu
                405                 410                 415

Val Leu Gly Ile Ser Leu Ala Ser Ser Leu Val Ala Ser Gly Leu Gly
            420                 425                 430

Lys Gly Ala Leu Thr His Ser Ile Gln Thr Ser Gln Asp Leu Ser Thr
        435                 440                 445

His Leu Gln Leu Ala Ile Glu Ala Ser Ala Glu Ser Leu Asp Ser Leu
450                 455                 460

Gln Arg Gln Ile Thr Thr Val Ala Gln Val Ala Ala Gln Asn Arg Gln
465                 470                 475                 480
```

Ala Leu Asp Leu Leu Met Ala Glu Lys Gly Arg Thr Cys Leu Phe Leu
                485                 490                 495

Gln Glu Glu Cys Cys Tyr Tyr Leu Asn Glu Ser Gly Val Val Glu Asn
            500                 505                 510

Ser Leu Gln Thr Leu Lys Lys Lys Ser Ser Lys Arg Ser
        515                 520                 525

<210> SEQ ID NO 71
<211> LENGTH: 626
<212> TYPE: PRT
<213> ORGANISM: Homo sapiens

<400> SEQUENCE: 71

Met Gly Pro Glu Ala Trp Val Arg Pro Leu Lys Thr Ala Pro Lys Pro
1               5                   10                  15

Gly Glu Ala Ile Arg Leu Ile Leu Phe Ile Tyr Leu Ser Cys Phe Phe
            20                  25                  30

Leu Pro Val Met Ser Ser Glu Pro Ser Tyr Ser Phe Leu Leu Thr Ser
        35                  40                  45

Phe Thr Thr Gly Arg Val Phe Ala Asn Thr Thr Trp Arg Ala Gly Thr
50                  55                  60

Ser Lys Glu Val Ser Phe Ala Val Asp Leu Cys Val Leu Phe Pro Glu
65                  70                  75                  80

Pro Ala Arg Thr His Glu Glu Gln His Asn Leu Pro Val Ile Gly Ala
                85                  90                  95

Gly Ser Val Asp Leu Ala Ala Gly Phe Gly His Ser Gly Ser Gln Thr
            100                 105                 110

Gly Cys Gly Ser Ser Lys Gly Ala Glu Lys Gly Leu Gln Asn Val Asp
        115                 120                 125

Phe Tyr Leu Cys Pro Gly Asn His Pro Asp Ala Ser Cys Arg Asp Thr
130                 135                 140

Tyr Gln Phe Phe Cys Pro Asp Trp Thr Cys Val Thr Leu Ala Thr Tyr
145                 150                 155                 160

Ser Gly Gly Ser Thr Arg Ser Ser Thr Leu Ser Ile Ser Arg Val Pro
                165                 170                 175

His Pro Lys Leu Cys Thr Arg Lys Asn Cys Asn Pro Leu Thr Ile Thr
            180                 185                 190

Val His Asp Pro Asn Ala Ala Gln Trp Tyr Tyr Gly Met Ser Trp Gly
        195                 200                 205

Leu Arg Leu Tyr Ile Pro Gly Phe Asp Val Gly Thr Met Phe Thr Ile
210                 215                 220

Gln Lys Lys Ile Leu Val Ser Trp Ser Ser Pro Lys Pro Ile Gly Pro
225                 230                 235                 240

Leu Thr Asp Leu Gly Asp Pro Ile Phe Gln Lys His Pro Asp Lys Val
                245                 250                 255

Asp Leu Thr Val Pro Leu Pro Phe Leu Val Pro Arg Pro Gln Leu Gln
            260                 265                 270

Gln Gln His Leu Gln Pro Ser Leu Met Ser Ile Leu Gly Gly Val His
        275                 280                 285

His Leu Leu Asn Leu Thr Gln Pro Lys Leu Ala Gln Asp Cys Trp Leu
290                 295                 300

Cys Leu Lys Ala Lys Pro Pro Tyr Tyr Val Gly Leu Gly Val Glu Ala
305                 310                 315                 320

Thr Leu Lys Arg Gly Pro Leu Ser Cys His Thr Arg Pro Arg Ala Leu

```
                325                 330                 335
Thr Ile Gly Asp Val Ser Gly Asn Ala Ser Cys Leu Ile Ser Thr Gly
            340                 345                 350
Tyr Asn Leu Ser Ala Ser Pro Phe Gln Ala Thr Cys Asn Gln Ser Leu
        355                 360                 365
Leu Thr Ser Ile Ser Thr Ser Val Ser Tyr Gln Ala Pro Asn Asn Thr
    370                 375                 380
Trp Leu Ala Cys Thr Ser Gly Leu Thr Arg Cys Ile Asn Gly Thr Glu
385                 390                 395                 400
Pro Gly Pro Leu Leu Cys Val Leu Val His Val Leu Pro Gln Val Tyr
                405                 410                 415
Val Tyr Ser Gly Pro Glu Gly Arg Gln Leu Ile Ala Pro Pro Glu Leu
            420                 425                 430
His Pro Arg Leu His Gln Ala Val Pro Leu Leu Val Pro Leu Leu Ala
        435                 440                 445
Gly Leu Ser Ile Ala Gly Ser Ala Ala Ile Gly Thr Ala Ala Leu Val
    450                 455                 460
Gln Gly Glu Thr Gly Leu Ile Ser Leu Ser Gln Gln Val Asp Ala Asp
465                 470                 475                 480
Phe Ser Asn Leu Gln Ser Ala Ile Asp Ile Leu His Ser Gln Val Glu
                485                 490                 495
Ser Leu Ala Glu Val Val Leu Gln Asn Cys Arg Cys Leu Asp Leu Leu
            500                 505                 510
Phe Leu Ser Gln Gly Gly Leu Cys Ala Ala Leu Gly Glu Ser Cys Cys
        515                 520                 525
Phe Tyr Ala Asn Gln Ser Gly Val Ile Lys Gly Thr Val Lys Lys Val
    530                 535                 540
Arg Glu Asn Leu Asp Arg His Gln Gln Glu Arg Glu Asn Asn Ile Pro
545                 550                 555                 560
Trp Tyr Gln Ser Met Phe Asn Trp Asn Pro Trp Leu Thr Thr Leu Ile
                565                 570                 575
Thr Gly Leu Ala Gly Pro Leu Leu Ile Leu Leu Leu Ser Leu Ile Phe
            580                 585                 590
Gly Pro Cys Ile Leu Asn Ser Phe Leu Asn Phe Ile Lys Gln Arg Ile
        595                 600                 605
Ala Ser Val Lys Leu Thr Tyr Leu Lys Thr Gln Tyr Asp Thr Leu Val
    610                 615                 620
Asn Asn
625

<210> SEQ ID NO 72
<211> LENGTH: 584
<212> TYPE: PRT
<213> ORGANISM: Homo sapiens

<400> SEQUENCE: 72

Met Ile Phe Ala Gly Lys Ala Pro Ser Asn Thr Ser Thr Leu Met Lys
1               5                   10                  15
Phe Tyr Ser Leu Leu Leu Tyr Ser Leu Leu Phe Ser Phe Pro Phe Leu
            20                  25                  30
Cys His Pro Leu Pro Leu Pro Ser Tyr Leu His His Thr Ile Asn Leu
        35                  40                  45
Thr His Ser Leu Leu Ala Ala Ser Asn Pro Ser Leu Val Asn Asn Cys
    50                  55                  60
```

```
Trp Leu Cys Ile Ser Leu Ser Ser Ala Tyr Thr Ala Val Pro Ala
 65                  70                  75                  80

Val Gln Thr Asp Trp Ala Thr Ser Pro Ile Ser Leu His Leu Arg Thr
                 85                  90                  95

Ser Phe Asn Ser Pro His Leu Tyr Pro Pro Glu Glu Leu Ile Tyr Phe
                100                 105                 110

Leu Asp Arg Ser Ser Lys Thr Ser Pro Asp Ile Ser His Gln Gln Ala
                115                 120                 125

Ala Ala Leu Leu Arg Thr Tyr Leu Lys Asn Leu Ser Pro Tyr Ile Asn
130                 135                 140

Ser Thr Pro Pro Ile Phe Gly Pro Leu Thr Thr Gln Thr Thr Ile Pro
145                 150                 155                 160

Val Ala Ala Pro Leu Cys Ile Ser Trp Gln Arg Pro Thr Gly Ile Pro
                165                 170                 175

Leu Gly Asn Leu Ser Pro Ser Arg Cys Ser Phe Thr Leu His Leu Arg
                180                 185                 190

Ser Pro Thr Thr Asn Ile Asn Glu Thr Ile Gly Ala Phe Gln Leu His
                195                 200                 205

Ile Thr Asp Lys Pro Ser Ile Asn Thr Asp Lys Leu Lys Asn Ile Ser
210                 215                 220

Ser Asn Tyr Cys Leu Gly Arg His Leu Pro Cys Ile Ser Leu His Pro
225                 230                 235                 240

Trp Leu Ser Ser Pro Cys Ser Ser Asp Ser Pro Pro Arg Pro Ser Ser
                245                 250                 255

Cys Leu Leu Ile Pro Ser Pro Glu Asn Asn Ser Glu Arg Leu Leu Val
                260                 265                 270

Asp Thr Arg Arg Phe Leu Ile His His Glu Asn Arg Thr Phe Pro Ser
                275                 280                 285

Thr Gln Leu Pro His Gln Ser Pro Leu Gln Pro Leu Thr Ala Ala Ala
                290                 295                 300

Leu Ala Gly Ser Leu Gly Val Trp Val Gln Asp Thr Pro Phe Ser Thr
305                 310                 315                 320

Pro Ser His Leu Phe Thr Leu His Leu Gln Phe Cys Leu Ala Gln Gly
                325                 330                 335

Leu Phe Phe Leu Cys Gly Ser Ser Thr Tyr Met Cys Leu Pro Ala Asn
                340                 345                 350

Trp Thr Gly Thr Cys Thr Leu Val Phe Leu Thr Pro Lys Ile Gln Phe
                355                 360                 365

Ala Asn Gly Thr Glu Glu Leu Pro Val Pro Leu Met Thr Pro Thr Gln
                370                 375                 380

Gln Lys Arg Val Ile Pro Leu Ile Pro Leu Met Val Gly Leu Gly Leu
385                 390                 395                 400

Ser Ala Ser Thr Val Ala Leu Gly Thr Gly Ile Ala Gly Ile Ser Thr
                405                 410                 415

Ser Val Met Thr Phe Arg Ser Leu Ser Asn Asp Phe Ser Ala Ser Ile
                420                 425                 430

Thr Asp Ile Ser Gln Thr Leu Ser Val Leu Gln Ala Gln Val Asp Ser
                435                 440                 445

Leu Ala Ala Val Val Leu Gln Asn Arg Arg Gly Leu Asp Leu Leu Thr
                450                 455                 460

Ala Glu Lys Gly Gly Leu Cys Ile Phe Leu Asn Glu Glu Cys Cys Phe
465                 470                 475                 480

Tyr Leu Asn Gln Ser Gly Leu Val Tyr Asp Asn Ile Lys Lys Leu Lys
```

-continued

```
                485                 490                 495
Asp Arg Ala Gln Lys Leu Ala Asn Gln Ala Ser Asn Tyr Ala Glu Pro
            500                 505                 510

Pro Trp Ala Leu Ser Asn Trp Met Ser Trp Val Leu Pro Ile Val Ser
        515                 520                 525

Pro Leu Ile Pro Ile Phe Leu Leu Leu Phe Gly Pro Cys Ile Phe
    530                 535                 540

Arg Leu Val Ser Gln Phe Ile Gln Asn Arg Ile Gln Ala Ile Thr Asn
545                 550                 555                 560

His Ser Ile Arg Gln Met Phe Leu Leu Thr Ser Pro Gln Tyr His Pro
                565                 570                 575

Leu Pro Gln Asp Leu Pro Ser Ala
            580

<210> SEQ ID NO 73
<211> LENGTH: 563
<212> TYPE: PRT
<213> ORGANISM: Homo sapiens

<400> SEQUENCE: 73

Met Ile Phe Ala Gly Arg Ala Ser Ser Asn Thr Ser Thr Leu Met Lys
1               5                   10                  15

Phe Tyr Ser Leu Leu Leu Tyr Ser Leu Leu Phe Ser Phe Pro Ile Leu
            20                  25                  30

Cys His Pro Leu Pro Leu Pro Ser Tyr Leu His His Thr Ile Asn Leu
        35                  40                  45

Thr His Ser Leu Leu Ala Val Ser Asn Pro Ser Leu Ala Lys Asn Cys
    50                  55                  60

Trp Leu Cys Ile Ser Leu Pro Ser Ser Ala Tyr Pro Ala Val Pro Ala
65                  70                  75                  80

Leu Gln Thr Asp Trp Gly Thr Ser Pro Val Ser Pro His Leu Arg Thr
                85                  90                  95

Ser Phe Asn Ser Pro His Leu Tyr Pro Pro Glu Lys Leu Ile Tyr Phe
            100                 105                 110

Leu Asp Arg Ser Ser Lys Thr Ser Pro Asp Ile Ser His Gln Gln Ala
        115                 120                 125

Ala Ala Leu Leu Cys Thr Tyr Leu Lys Asn Leu Ser Pro Tyr Ile Asn
    130                 135                 140

Ser Thr Pro Pro Thr Phe Gly Pro Leu Thr Thr Gln Thr Thr Ile Pro
145                 150                 155                 160

Val Ala Ala Pro Leu Cys Ile Ser Arg Gln Arg Pro Thr Gly Ile Pro
                165                 170                 175

Leu Gly Asn Leu Ser Pro Ser Arg Cys Ser Phe Thr Leu His Leu Arg
            180                 185                 190

Ser Pro Thr Thr His Ile Thr Glu Thr Asn Gly Ala Phe Gln Leu His
        195                 200                 205

Ile Thr Asp Lys Pro Ser Ile Asn Thr Asp Lys Leu Lys Asn Val Ser
    210                 215                 220

Ser Asn Tyr Cys Leu Gly Arg His Leu Ser Cys Ile Ser Leu His Pro
225                 230                 235                 240

Trp Leu Phe Ser Pro Cys Ser Ser Asp Ser Pro Pro Arg Pro Ser Ser
                245                 250                 255

Cys Leu Leu Ile Pro Ser Pro Lys Asn Asn Ser Glu Ser Leu Leu Val
            260                 265                 270
```

```
Asp Ala Gln Arg Phe Leu Ile Tyr His Glu Asn Arg Thr Ser Pro Ser
            275                 280                 285

Thr Gln Leu Pro His Gln Ser Pro Leu Gln Pro Leu Thr Ala Ala Pro
290                 295                 300

Leu Gly Gly Ser Leu Arg Val Trp Val Gln Asp Thr Pro Phe Ser Thr
305                 310                 315                 320

Pro Ser His Leu Phe Thr Leu His Leu Gln Phe Cys Leu Val Gln Ser
                325                 330                 335

Leu Phe Phe Leu Cys Gly Ser Ser Thr Tyr Met Cys Leu Pro Ala Asn
            340                 345                 350

Trp Thr Gly Thr Cys Thr Leu Val Phe Leu Thr Ser Lys Ile Gln Phe
        355                 360                 365

Ala Asn Gly Thr Glu Glu Leu Pro Val Pro Leu Met Thr Pro Thr Arg
370                 375                 380

Gln Lys Arg Val Ile Pro Leu Ile Pro Leu Met Val Gly Leu Gly Leu
385                 390                 395                 400

Ser Ala Ser Thr Val Ala Leu Gly Thr Gly Ile Ala Gly Ile Ser Thr
                405                 410                 415

Ser Val Thr Thr Phe Arg Ile Leu Ser Asn Asp Phe Ser Ala Ser Ile
            420                 425                 430

Thr Asp Ile Ser Gln Thr Leu Ser Gly Leu Gln Ala Gln Val Asp Ser
        435                 440                 445

Ser Ala Ala Val Val Leu Gln Asn Arg Gln Gly Leu Asp Leu Leu Thr
450                 455                 460

Ala Glu Lys Gly Gly Leu Cys Ile Phe Leu Asn Glu Glu Ser Tyr Phe
465                 470                 475                 480

Tyr Leu Asn Gln Ser Gly Leu Val Tyr Asp Asn Ile Lys Lys Leu Lys
                485                 490                 495

Asp Lys Ala Gln Asn Leu Ala Asn Gln Ala Ser Asn Tyr Ala Glu Pro
            500                 505                 510

Pro Trp Pro Leu Ser Asn Trp Met Ser Trp Val Leu Pro Ile Leu Ser
        515                 520                 525

Pro Leu Ile Pro Ile Phe Leu Leu Leu Phe Phe Arg Pro Cys Ile Phe
530                 535                 540

His Leu Val Ser Gln Phe Ile Gln Asn His Ile Gln Ala Ile Thr Asp
545                 550                 555                 560

His Ser Ile

<210> SEQ ID NO 74
<211> LENGTH: 555
<212> TYPE: PRT
<213> ORGANISM: Homo sapiens

<400> SEQUENCE: 74

Met Ile Leu Ala Gly Arg Ala Pro Ser Asn Thr Ser Thr Leu Met Lys
1               5                   10                  15

Phe Tyr Ser Leu Leu Leu Tyr Ser Leu Phe Ser Phe Pro Phe Leu
                20                  25                  30

Tyr His Pro Leu Pro Leu Pro Ser Tyr Leu His His Thr Ile Asn Leu
            35                  40                  45

Thr His Ser Leu Pro Ala Ala Ser Asn Pro Ser Leu Ala Asn Asn Cys
        50                  55                  60

Trp Leu Cys Ile Ser Leu Ser Ser Ser Ala Tyr Ile Ala Val Pro Thr
65                  70                  75                  80
```

```
Leu Gln Thr Asp Arg Ala Thr Ser Pro Val Ser Leu His Leu Arg Thr
             85                  90                  95

Ser Phe Asn Ser Pro His Leu Tyr Pro Pro Glu Glu Leu Ile Tyr Phe
            100                 105                 110

Leu Asp Arg Ser Ser Lys Thr Ser Pro Asp Ile Ser His Gln Pro Ala
        115                 120                 125

Ala Ala Leu Leu His Ile Tyr Leu Lys Asn Leu Ser Pro Tyr Ile Asn
    130                 135                 140

Ser Thr Pro Pro Ile Phe Gly Pro Leu Thr Thr Gln Thr Thr Ile Pro
145                 150                 155                 160

Val Ala Ala Pro Leu Cys Ile Ser Arg Gln Arg Pro Thr Gly Ile Pro
                165                 170                 175

Leu Gly Asn Ile Ser Pro Ser Arg Cys Ser Phe Thr Leu His Leu Gln
            180                 185                 190

Ser Pro Thr Thr His Val Thr Glu Thr Ile Gly Val Phe Gln Leu His
        195                 200                 205

Ile Ile Asp Lys Pro Ser Ile Asn Thr Asp Lys Leu Lys Asn Val Ser
    210                 215                 220

Ser Asn Tyr Cys Leu Gly Arg His Leu Pro Tyr Ile Ser Leu His Pro
225                 230                 235                 240

Trp Leu Pro Ser Pro Cys Ser Ser Asp Ser Pro Arg Pro Ser Ser
                245                 250                 255

Cys Leu Leu Thr Pro Ser Pro Gln Asn Asn Ser Glu Arg Leu Leu Val
            260                 265                 270

Asp Thr Gln Arg Phe Leu Ile His His Glu Asn Arg Thr Ser Ser Ser
        275                 280                 285

Met Gln Leu Ala His Gln Ser Pro Leu Gln Pro Leu Thr Ala Ala Ala
    290                 295                 300

Leu Ala Gly Ser Leu Gly Val Trp Val Gln Asp Thr Pro Phe Ser Thr
305                 310                 315                 320

Pro Ser His Pro Phe Ser Leu His Leu Gln Phe Cys Leu Thr Gln Gly
                325                 330                 335

Leu Phe Phe Leu Cys Gly Ser Ser Thr Tyr Met Cys Leu Pro Ala Asn
            340                 345                 350

Trp Thr Gly Thr Cys Thr Leu Val Phe Leu Thr Pro Lys Ile Gln Phe
        355                 360                 365

Ala Asn Gly Thr Lys Glu Leu Pro Val Pro Leu Met Thr Leu Thr Pro
    370                 375                 380

Gln Lys Arg Val Ile Pro Leu Ile Pro Leu Met Val Gly Leu Gly Leu
385                 390                 395                 400

Ser Ala Ser Thr Ile Ala Leu Ser Thr Gly Ile Ala Gly Ile Ser Thr
                405                 410                 415

Ser Val Thr Thr Phe Arg Ser Pro Ser Asn Asp Phe Ser Ala Ser Ile
            420                 425                 430

Thr Asp Ile Ser Gln Thr Leu Ser Val Leu Gln Ala Gln Val Asp Ser
        435                 440                 445

Leu Ala Ala Val Val Leu Gln Asn Arg Arg Gly Leu Gly Leu Ser Ile
    450                 455                 460

Leu Leu Asn Glu Glu Cys Cys Phe Tyr Leu Asn Gln Ser Gly Leu Val
465                 470                 475                 480

Tyr Glu Asn Ile Lys Lys Leu Lys Asp Arg Ala Gln Lys Leu Ala Asn
                485                 490                 495

Gln Ala Ser Asn Tyr Ala Glu Ser Pro Trp Ala Leu Ser Asn Trp Met
```

```
                500             505             510
Ser Trp Val Leu Pro Ile Leu Ser Pro Leu Ile Pro Ile Phe Leu Leu
            515             520             525

Leu Leu Phe Gly Pro Cys Ile Phe His Leu Val Ser Gln Phe Ile Gln
        530             535             540

Asn Arg Ile Gln Ala Ile Thr Asn His Ser Ile
545             550             555

<210> SEQ ID NO 75
<211> LENGTH: 604
<212> TYPE: PRT
<213> ORGANISM: Homo sapiens

<400> SEQUENCE: 75

Met Leu Gly Met Asn Met Leu Leu Ile Thr Leu Phe Leu Leu Leu Pro
1               5                   10                  15

Leu Ser Met Leu Lys Gly Glu Pro Trp Glu Gly Cys Leu His Cys Thr
            20                  25                  30

His Thr Thr Trp Ser Gly Asn Ile Met Thr Lys Thr Leu Leu Tyr His
        35                  40                  45

Thr Tyr Tyr Glu Cys Ala Gly Thr Cys Leu Gly Thr Cys Thr His Asn
    50                  55                  60

Gln Thr Thr Tyr Ser Val Cys Asp Pro Gly Arg Gly Gln Pro Tyr Val
65                  70                  75                  80

Cys Tyr Asp Pro Lys Ser Ser Pro Gly Thr Trp Phe Glu Ile His Val
                85                  90                  95

Gly Ser Lys Glu Gly Asp Leu Leu Asn Gln Thr Lys Val Phe Pro Ser
            100                 105                 110

Gly Lys Asp Val Val Ser Leu Tyr Phe Asp Val Cys Gln Ile Val Ser
        115                 120                 125

Met Gly Ser Leu Phe Pro Val Ile Phe Ser Ser Met Glu Tyr Tyr Ser
    130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205

Gln Pro Ile Trp Thr Thr Gly Leu Lys Ala Pro Leu Gly Ala Arg Val
    210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
                245                 250                 255

Phe Tyr Glu His Val Asn Gln Lys Leu Pro Glu Pro Pro Leu Ala
            260                 265                 270

Ser Asn Leu Phe Ala Gln Leu Ala Glu Asn Ile Ala Ser Ser Leu His
        275                 280                 285

Val Ala Ser Cys Tyr Val Cys Gly Gly Met Asn Met Gly Asp Gln Trp
    290                 295                 300

Pro Trp Glu Ala Arg Glu Leu Met Pro Gln Asp Asn Phe Thr Leu Thr
305                 310                 315                 320
```

Ala Ser Ser Leu Glu Pro Ala Pro Ser Ser Gln Ser Ile Trp Phe Leu
                325                 330                 335

Lys Thr Ser Ile Ile Gly Lys Phe Cys Ile Ala Arg Trp Gly Lys Ala
            340                 345                 350

Phe Thr Asp Pro Val Gly Glu Leu Thr Cys Leu Gly Gln Gln Tyr Tyr
        355                 360                 365

Asn Glu Thr Leu Gly Lys Thr Leu Trp Arg Gly Lys Ser Asn Asn Ser
    370                 375                 380

Glu Ser Pro His Pro Ser Pro Phe Ser Arg Phe Pro Ser Leu Asn His
385                 390                 395                 400

Ser Trp Tyr Gln Leu Glu Ala Pro Asn Thr Trp Gln Ala Pro Ser Gly
                405                 410                 415

Leu Tyr Trp Ile Cys Gly Pro Gln Ala Tyr Arg Gln Leu Pro Ala Lys
            420                 425                 430

Trp Ser Gly Ala Cys Val Leu Gly Thr Ile Arg Pro Ser Phe Phe Leu
        435                 440                 445

Met Pro Leu Lys Gln Gly Glu Ala Leu Gly Tyr Pro Ile Tyr Asp Glu
    450                 455                 460

Thr Lys Arg Lys Ser Lys Arg Gly Ile Thr Ile Gly Asp Trp Lys Asp
465                 470                 475                 480

Asn Glu Trp Pro Pro Glu Arg Ile Ile Gln Tyr Tyr Gly Pro Ala Thr
                485                 490                 495

Trp Ala Glu Asp Gly Met Trp Gly Tyr Arg Thr Pro Val Tyr Met Leu
            500                 505                 510

Asn Arg Ile Ile Arg Leu Gln Ala Val Leu Glu Ile Ile Thr Asn Glu
        515                 520                 525

Thr Ala Gly Ala Leu Asn Leu Leu Ala Gln Gln Ala Thr Lys Met Arg
    530                 535                 540

Asn Val Ile Tyr Gln Asn Arg Leu Ala Leu Asp Tyr Leu Leu Ala Gln
545                 550                 555                 560

Glu Glu Gly Val Cys Gly Lys Phe Asn Leu Thr Asn Cys Cys Leu Glu
                565                 570                 575

Leu Asp Asp Glu Gly Lys Val Ile Lys Glu Ile Thr Ala Lys Ile Gln
            580                 585                 590

Lys Leu Ala His Ile Pro Val Gln Thr Trp Lys Gly
        595                 600

<210> SEQ ID NO 76
<211> LENGTH: 514
<212> TYPE: PRT
<213> ORGANISM: Homo sapiens

<400> SEQUENCE: 76

Met Asp Pro Leu His Thr Ile Glu Lys Val Pro Ala Arg Arg Asn Ile
1               5                   10                  15

His Asp Arg Gly His Gln Gly His Arg Met Gly Asp Gly Thr Pro Gly
                20                  25                  30

Arg Pro Lys Ile Ser Val Gln Gln Met Thr Arg Phe Ser Leu Ile Ile
            35                  40                  45

Phe Phe Leu Ser Ala Pro Phe Val Val Asn Ala Ser Thr Ser Asn Val
        50                  55                  60

Phe Leu Gln Trp Ala His Ser Tyr Ala Asp Gly Leu Gln Gln Gly Asp
65                  70                  75                  80

Pro Cys Trp Val Cys Gly Ser Leu Pro Val Thr Asn Thr Met Glu Leu
                85                  90                  95

-continued

```
Pro Trp Trp Val Ser Pro Leu Gln Gly Lys Asp Trp Val Phe Phe Gln
            100                 105                 110

Ser Phe Ile Gly Asp Leu Lys Gln Trp Thr Gly Ala Gln Met Thr Gly
            115                 120                 125

Val Thr Arg Lys Asn Ile Ser Glu Trp Pro Ile Asn Lys Thr Leu Asn
        130                 135                 140

Glu Pro Gly His Asp Lys Pro Phe Ser Val Asn Glu Thr Arg Asp Lys
145                 150                 155                 160

Val Ile Ala Phe Ala Ile Pro Leu Leu Asp Thr Lys Val Phe Val Gln
                165                 170                 175

Thr Ser Arg Pro Gln Asn Thr Gln Tyr Arg Asn Gly Phe Leu Gln Ile
            180                 185                 190

Trp Asp Gly Phe Ile Trp Leu Thr Ala Thr Lys Gly His Leu Ser Gln
            195                 200                 205

Ile Ala Pro Leu Cys Trp Glu Gln Arg Asn His Ser Leu Asp Asn Trp
        210                 215                 220

Pro Asn Thr Thr Arg Val Met Gly Trp Ile Pro Pro Gly Gln Cys Arg
225                 230                 235                 240

His Thr Ile Leu Leu Gln Gln Arg Asp Leu Phe Ala Thr Asp Trp Ser
                245                 250                 255

Gln Gln Pro Gly Leu Asn Trp Tyr Ala Pro Asn Gly Thr Gln Trp Leu
            260                 265                 270

Cys Ser Pro Asn Leu Trp Pro Trp Leu Pro Ser Gly Trp Leu Gly Cys
            275                 280                 285

Cys Thr Leu Gly Ile Pro Trp Ala Gln Gly Arg Trp Val Lys Thr Met
        290                 295                 300

Glu Val Tyr Pro Tyr Leu Pro His Val Val Asn Gln Gly Thr Arg Ala
305                 310                 315                 320

Ile Val His Arg Asn Asp His Leu Pro Thr Ile Phe Met Pro Ser Val
                325                 330                 335

Gly Leu Gly Thr Val Ile Gln His Ile Glu Ala Leu Ala Asn Phe Thr
            340                 345                 350

Gln Arg Ala Leu Asn Asp Ser Leu Gln Ser Ile Ser Leu Met Asn Ala
            355                 360                 365

Glu Val Tyr Tyr Met His Glu Asp Ile Leu Gln Asn Arg Met Ala Leu
        370                 375                 380

Asp Ile Leu Thr Ala Ala Glu Gly Gly Thr Cys Ala Leu Ile Lys Thr
385                 390                 395                 400

Glu Cys Cys Val Tyr Ile Pro Asn Asn Ser Arg Asn Ile Ser Leu Ala
                405                 410                 415

Leu Glu Asp Thr Cys Arg Gln Ile Gln Val Ile Ser Ser Ser Ala Leu
            420                 425                 430

Ser Leu His Asp Trp Ile Ala Ser Gln Phe Ser Gly Arg Pro Ser Trp
            435                 440                 445

Trp Gln Lys Ile Leu Ile Val Leu Ala Thr Leu Trp Ser Val Gly Ile
        450                 455                 460

Ala Leu Cys Cys Gly Leu Tyr Phe Cys Arg Met Phe Ser Gln His Ile
465                 470                 475                 480

Pro Gln Thr His Ser Ile Ile Phe Gln Gln Glu Leu Pro Leu Ser Pro
                485                 490                 495

Pro Ser Gln Glu His Tyr Gln Ser Gln Arg Asp Ile Phe His Ser Asn
            500                 505                 510
```

Ala Pro

<210> SEQ ID NO 77
<211> LENGTH: 698
<212> TYPE: PRT
<213> ORGANISM: Homo sapiens

<400> SEQUENCE: 77

```
Met His Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
            20                  25                  30

Ser Glu Gln Met Lys Leu Pro Ser Thr Lys Lys Ala Glu Pro Pro Thr
            35                  40                  45

Trp Ala Gln Leu Lys Lys Leu Thr Gln Leu Ala Thr Lys Tyr Leu Glu
        50                  55                  60

Asn Thr Lys Val Thr Gln Thr Pro Glu Ser Met Leu Leu Ala Ala Leu
65                  70                  75                  80

Met Ile Val Ser Met Val Val Ser Leu Pro Met Pro Ala Gly Ala Ala
                85                  90                  95

Ala Ala Asn Tyr Thr Asn Trp Ala Tyr Val Pro Phe Pro Pro Leu Ile
            100                 105                 110

Arg Ala Val Thr Trp Met Asp Asn Pro Ile Glu Val Tyr Val Asn Asp
            115                 120                 125

Ser Val Trp Val His Gly Pro Ile Asp Asp Arg Cys Pro Ala Lys Pro
130                 135                 140

Glu Glu Glu Gly Met Met Ile Asn Ile Ser Ile Gly Tyr His Tyr Pro
145                 150                 155                 160

Pro Ile Cys Leu Gly Arg Ala Pro Gly Cys Leu Met Pro Ala Val Gln
                165                 170                 175

Asn Trp Leu Val Glu Val Pro Thr Val Ser Pro Ile Ser Arg Phe Thr
            180                 185                 190

Tyr Asn Met Val Ser Gly Met Ser Leu Arg Pro Arg Val Asn Tyr Leu
            195                 200                 205

Gln Asp Phe Ser Tyr Gln Arg Ser Leu Lys Phe Arg Pro Lys Gly Lys
        210                 215                 220

Pro Cys Pro Lys Glu Ile Pro Lys Glu Ser Lys Asn Thr Glu Val Leu
225                 230                 235                 240

Val Trp Glu Glu Cys Val Ala Asn Ser Val Val Ile Leu Gln Asn Asn
                245                 250                 255

Glu Phe Gly Thr Ile Ile Asp Trp Ala Pro Arg Gly Gln Phe Tyr His
            260                 265                 270

Asn Cys Ser Gly Gln Thr Gln Ser Cys Pro Ser Ala Gln Val Ser Pro
            275                 280                 285

Ala Val Asp Ser Asp Leu Thr Glu Ser Leu Asp Lys His Lys His Lys
        290                 295                 300

Lys Leu Gln Ser Phe Tyr Pro Trp Glu Trp Gly Lys Gly Ile Ser
305                 310                 315                 320

Thr Pro Arg Pro Lys Ile Ile Ser Pro Val Ser Gly Pro Glu His Pro
                325                 330                 335

Glu Leu Trp Arg Leu Thr Val Ala Ser His His Ile Arg Ile Trp Ser
            340                 345                 350

Gly Asn Gln Thr Leu Glu Thr Arg Asp Arg Lys Pro Phe Tyr Thr Val
            355                 360                 365
```

Asp Leu Asn Ser Ser Leu Thr Val Pro Leu Gln Ser Cys Val Lys Pro
    370                 375                 380

Pro Tyr Met Leu Val Val Gly Asn Ile Val Ile Lys Pro Asp Ser Gln
385                 390                 395                 400

Thr Ile Thr Cys Glu Asn Cys Arg Leu Leu Thr Cys Ile Asp Ser Thr
                405                 410                 415

Phe Asn Trp Gln His Arg Ile Leu Leu Val Arg Ala Arg Glu Gly Val
            420                 425                 430

Trp Ile Pro Val Ser Met Asp Arg Pro Trp Glu Ala Ser Pro Ser Ile
        435                 440                 445

His Ile Leu Thr Glu Val Leu Lys Gly Val Leu Asn Arg Ser Lys Arg
    450                 455                 460

Phe Ile Phe Thr Leu Ile Ala Val Ile Met Gly Leu Ile Ala Val Thr
465                 470                 475                 480

Ala Met Ala Ala Val Ala Gly Val Ala Leu His Ser Phe Val Gln Ser
                485                 490                 495

Val Asn Phe Val Asn Asp Trp Gln Lys Asn Ser Thr Arg Leu Trp Asn
                500                 505                 510

Ser Gln Ser Ser Ile Asp Gln Lys Leu Ala Asn Gln Ile Asn Asp Leu
    515                 520                 525

Arg Gln Thr Val Ile Trp Met Gly Asp Arg Leu Met Ser Leu Glu His
    530                 535                 540

Arg Phe Gln Leu Gln Cys Asp Trp Asn Thr Ser Asp Phe Cys Ile Thr
545                 550                 555                 560

Pro Gln Ile Tyr Asn Glu Ser Glu His His Trp Asp Met Val Arg Arg
                565                 570                 575

His Leu Gln Gly Arg Glu Asp Asn Leu Thr Leu Asp Ile Ser Lys Leu
            580                 585                 590

Lys Glu Gln Ile Phe Glu Ala Ser Lys Ala His Leu Asn Leu Val Pro
        595                 600                 605

Gly Thr Glu Ala Ile Ala Gly Val Ala Asp Gly Leu Ala Asn Leu Asn
    610                 615                 620

Pro Val Thr Trp Val Lys Thr Ile Gly Ser Thr Thr Ile Ile Asn Leu
625                 630                 635                 640

Ile Leu Ile Leu Val Cys Leu Phe Cys Leu Leu Leu Val Cys Arg Phe
                645                 650                 655

Thr Gln Gln Leu Arg Arg Asp Ser Tyr His Arg Glu Arg Ala Met Met
            660                 665                 670

Thr Met Val Val Leu Ser Lys Arg Lys Gly Gly Asn Val Gly Lys Ser
        675                 680                 685

Lys Arg Asp Gln Ile Val Thr Val Ser Val
    690                 695

<210> SEQ ID NO 78
<211> LENGTH: 699
<212> TYPE: PRT
<213> ORGANISM: Homo sapiens

<400> SEQUENCE: 78

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

-continued

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                      70                  75                  80

Leu Met Ile Val Ser Met Val Val Ser Leu Pro Met Pro Ala Gly Ala
                    85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Thr Glu Val Tyr Val Asn
            115                 120                 125

Asp Ser Val Trp Val Pro Gly Pro Ile Asp Asp Arg Cys Pro Ala Lys
    130                 135                 140

Pro Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Cys Arg Phe
                180                 185                 190

Thr Tyr His Met Val Ser Gly Met Ser Leu Arg Pro Arg Val Asn Tyr
            195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Val Ser Pro Val Ser Gly Pro Glu His
                325                 330                 335

Pro Glu Leu Trp Arg Leu Thr Val Ala Ser His His Ile Arg Ile Trp
                340                 345                 350

Ser Gly Asn Gln Thr Leu Glu Thr Arg Asp Arg Lys Pro Phe Tyr Thr
            355                 360                 365

Ile Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Arg Ser Lys
    450                 455                 460

```
Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
            485                 490                 495

Ser Val Asn Phe Val Asn Asp Trp Gln Lys Asn Ser Thr Arg Leu Trp
        500                 505                 510

Asn Ser Gln Ser Ser Ile Asp Gln Lys Leu Ala Asn Gln Ile Asn Asp
    515                 520                 525

Leu Arg Gln Thr Val Ile Trp Met Gly Asp Arg Leu Met Ser Leu Glu
530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Arg His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
        595                 600                 605

Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Val Cys Arg
                645                 650                 655

Cys Thr Gln Gln Leu Arg Arg Asp Ser Asp His Arg Glu Arg Ala Met
                660                 665                 670

Met Thr Met Ala Val Leu Ser Lys Arg Lys Gly Gly Asn Val Gly Lys
            675                 680                 685

Ser Lys Arg Asp Gln Ile Val Thr Val Ser Val
            690                 695

<210> SEQ ID NO 79
<211> LENGTH: 699
<212> TYPE: PRT
<213> ORGANISM: Homo sapiens

<400> SEQUENCE: 79

Met Asn Pro Ser Glu Met Gln Arg Lys Ala Pro Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Ile Glu Val Tyr Val Asn
        115                 120                 125

Asp Ser Val Trp Val Pro Gly Pro Thr Asp Asp His Cys Pro Ala Lys
    130                 135                 140
```

```
Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
            165                 170                 175

Gln Asn Trp Leu Val Glu Val Pro Thr Val Ser Pro Ile Ser Arg Phe
        180                 185                 190

Thr Tyr His Met Val Ser Gly Met Ser Leu Arg Pro Arg Val Asn Tyr
            195                 200                 205

Leu Gln Asp Phe Ser Tyr Gln Arg Ser Phe Lys Phe Arg Pro Lys Gly
        210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
        290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Val Asp Leu Asn Ser Ser Val Thr Val Pro Leu Gln Ser Cys Ile Lys
        370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Thr Ser Pro Ser
        435                 440                 445

Ile His Thr Leu Thr Glu Val Leu Lys Gly Val Leu Asn Arg Ser Lys
        450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Leu Ala Asn Gln Ile Asn Asp
        515                 520                 525

Leu Arg Gln Thr Val Ile Trp Met Gly Asp Arg Leu Met Ser Leu Glu
        530                 535                 540

His Arg Phe Gln Leu Gln Cys Asp Trp Asn Thr Ser Asp Phe Ser Ile
545                 550                 555                 560
```

Thr Pro Gln Ile Tyr Asn Glu Ser Glu His Trp Asp Met Val Arg
            565                 570                 575

Arg His Leu Gln Gly Arg Glu Asp Asn Leu Thr Leu Asp Ile Ser Lys
        580                 585                 590

Leu Lys Glu Gln Ile Phe Glu Ala Ser Lys Ala His Leu Asn Leu Val
    595                 600                 605

Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
                645                 650                 655

Cys Thr Gln Gln Leu Arg Arg Asp Ser Asp His Arg Glu Arg Ala Met
            660                 665                 670

Met Thr Met Ala Val Leu Ser Lys Arg Lys Gly Gly Asn Val Gly Lys
        675                 680                 685

Ser Lys Arg Asp Gln Ile Val Thr Val Ser Val
    690                 695

<210> SEQ ID NO 80
<211> LENGTH: 698
<212> TYPE: PRT
<213> ORGANISM: Homo sapiens

<400> SEQUENCE: 80

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Asn Trp Ala Tyr Val Pro Phe Pro Pro Leu
            100                 105                 110

Ile Arg Ala Val Thr Trp Met Asp Asn Pro Ile Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr Arg Tyr
145                 150                 155                 160

Pro Ile Cys Leu Gly Arg Ala Pro Gly Cys Leu Met Pro Ala Val Gln
                165                 170                 175

Asn Trp Leu Val Glu Val Pro Ile Val Ser Pro Ile Cys Arg Phe Thr
            180                 185                 190

Tyr His Met Val Ser Gly Met Ser Leu Arg Pro Arg Val Asn Tyr Leu
        195                 200                 205

Gln Asp Phe Ser Tyr Gln Arg Ser Leu Lys Phe Arg Pro Lys Gly Lys
    210                 215                 220

Pro Cys Pro Lys Glu Ile Pro Lys Glu Ser Lys Asn Thr Glu Val Leu
225                 230                 235                 240

-continued

```
Val Trp Glu Glu Cys Val Ala Asn Ser Ala Val Ile Leu Gln Asn Asn
                245                 250                 255
Glu Phe Gly Thr Ile Ile Asp Trp Thr Pro Gln Gly Gln Phe Tyr His
            260                 265                 270
Asn Cys Ser Gly Gln Thr Gln Ser Cys Pro Ser Ala Gln Val Ser Pro
        275                 280                 285
Ala Val Asp Ser Asp Leu Thr Glu Ser Leu Asp Lys His Lys His Lys
    290                 295                 300
Lys Leu Gln Ser Phe Tyr Pro Trp Glu Trp Gly Glu Lys Gly Ile Ser
305                 310                 315                 320
Thr Pro Arg Pro Lys Ile Ile Ser Pro Val Ser Gly Pro Glu His Pro
                325                 330                 335
Glu Leu Trp Arg Leu Thr Val Ala Ser His His Ile Arg Ile Trp Ser
            340                 345                 350
Gly Asn Gln Thr Leu Glu Thr Arg Asp Arg Lys Pro Phe Tyr Thr Val
        355                 360                 365
Asp Leu Asn Ser Ser Leu Thr Leu Pro Leu Gln Ser Cys Val Lys Pro
    370                 375                 380
Pro Tyr Met Leu Val Val Gly Asn Ile Val Ile Lys Pro Asp Ser Gln
385                 390                 395                 400
Thr Ile Thr Cys Glu Asn Cys Arg Leu Leu Thr Cys Ile Asp Ser Thr
                405                 410                 415
Phe Asn Trp Gln His Arg Ile Leu Leu Val Arg Ala Arg Glu Gly Val
            420                 425                 430
Trp Ile Pro Val Ser Met Asp Arg Pro Trp Glu Ala Ser Pro Ser Ile
        435                 440                 445
His Ile Leu Thr Glu Val Leu Lys Gly Val Leu Asn Arg Ser Lys Arg
    450                 455                 460
Phe Ile Phe Thr Leu Ile Ala Val Ile Met Gly Leu Ile Ala Val Thr
465                 470                 475                 480
Ala Thr Ala Ala Val Ala Gly Val Ala Leu His Ser Ser Val Gln Ser
                485                 490                 495
Val Asn Phe Val Asn Asp Gly Gln Lys Asn Ser Thr Arg Leu Trp Asn
            500                 505                 510
Ser Gln Ser Ser Ile Asp Gln Lys Leu Ala Asn Gln Ile Asn Asp Leu
        515                 520                 525
Arg Gln Thr Val Ile Trp Met Gly Asp Arg Leu Met Ser Leu Glu His
    530                 535                 540
Arg Phe Gln Leu Gln Cys Asp Trp Asn Thr Ser Asp Phe Cys Ile Thr
545                 550                 555                 560
Pro Gln Ile Tyr Asn Glu Ser Glu His His Trp Asp Met Val Arg Arg
                565                 570                 575
His Leu Gln Gly Arg Glu Asp Asn Leu Thr Leu Asp Ile Ser Lys Leu
            580                 585                 590
Lys Glu Gln Ile Phe Glu Ala Ser Lys Ala His Leu Asn Leu Val Pro
        595                 600                 605
Gly Thr Glu Ala Ile Ala Gly Val Ala Asp Gly Leu Ala Asn Leu Asn
    610                 615                 620
Pro Val Thr Trp Val Lys Thr Ile Gly Ser Thr Thr Ile Ile Asn Leu
625                 630                 635                 640
Ile Leu Ile Leu Val Cys Leu Phe Cys Leu Leu Leu Val Cys Arg Cys
                645                 650                 655
```

```
Thr Gln Gln Leu Arg Arg Asp Ser Asp His Arg Glu Arg Ala Met Met
            660                 665                 670

Thr Met Ala Val Leu Ser Lys Arg Lys Gly Gly Asn Val Gly Lys Ser
            675                 680                 685

Lys Arg Asp Gln Ile Val Thr Val Ser Val
            690                 695

<210> SEQ ID NO 81
<211> LENGTH: 699
<212> TYPE: PRT
<213> ORGANISM: Homo sapiens

<400> SEQUENCE: 81

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Ile Glu Ile Tyr Val Asn
            115                 120                 125

Asp Ser Val Trp Val Pro Gly Pro Thr Asp Asp Cys Cys Pro Ala Lys
    130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Leu Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Ala Arg Pro Lys Ile Ile Ser Pro Val Ser Gly Pro Glu His
                325                 330                 335
```

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
            355                 360                 365

Ile Asp Leu Asn Ser Ser Leu Thr Val Pro Leu Gln Ser Cys Val Lys
        370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
            405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
            435                 440                 445

Val His Ile Leu Thr Glu Val Leu Lys Gly Val Leu Asn Arg Ser Lys
            450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
            485                 490                 495

Ser Val Asn Phe Val Asn Asp Trp Gln Asn Asn Ser Thr Arg Leu Trp
            500                 505                 510

Asn Ser Gln Ser Ser Ile Asp Gln Lys Leu Ala Asn Gln Ile Asn Asp
            515                 520                 525

Leu Arg Gln Thr Val Ile Trp Met Gly Asp Arg Leu Met Ser Leu Glu
            530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
            565                 570                 575

Cys His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
            595                 600                 605

Pro Gly Thr Glu Ala Ile Ala Gly Val Ala Asp Gly Leu Ala Asn Leu
            610                 615                 620

Asn Thr Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Tyr Arg
            645                 650                 655

Cys Thr Gln Gln Leu Arg Arg Asp Ser Asp His Arg Glu Arg Ala Met
            660                 665                 670

Met Thr Met Val Val Leu Ser Lys Arg Lys Gly Gly Asn Val Gly Lys
            675                 680                 685

Ser Lys Arg Asp Gln Ile Val Thr Val Ser Val
            690                 695

<210> SEQ ID NO 82
<211> LENGTH: 699
<212> TYPE: PRT
<213> ORGANISM: Homo sapiens

<400> SEQUENCE: 82

Met Asn Pro Ser Glu Met Gln Arg Lys Ala Pro Pro Arg Arg Arg Arg

-continued

```
1               5                   10                  15
His Arg Asn Arg Ala Pro Leu Thr His Lys Met Asn Lys Met Val Thr
                20                  25                  30
Ser Glu Glu Gln Met Lys Leu Pro Ser Thr Lys Lys Ala Glu Pro Pro
                35                  40                  45
Thr Trp Ala Gln Leu Lys Lys Leu Thr Gln Leu Ala Thr Lys Tyr Leu
    50                  55                  60
Glu Asn Thr Lys Val Thr Gln Thr Pro Glu Ser Met Leu Leu Ala Ala
65                  70                  75                  80
Leu Met Ile Val Ser Met Val Val Ser Leu Pro Met Pro Ala Gly Ala
                85                  90                  95
Ala Val Ala Asn Tyr Thr Asn Trp Ala Tyr Val Pro Phe Pro Pro Leu
                100                 105                 110
Ile Arg Ala Val Thr Trp Met Asp Asn Pro Ile Glu Val Tyr Val Asn
                115                 120                 125
Asp Ser Val Trp Val Pro Gly Pro Ile Asp Asp Arg Cys Pro Ala Lys
    130                 135                 140
Pro Glu Glu Glu Gly Met Met Ile Asn Ile Ser Ile Gly Tyr Arg Tyr
145                 150                 155                 160
Pro Pro Ile Cys Leu Gly Arg Ala Pro Gly Cys Leu Met Pro Ala Val
                165                 170                 175
Gln Asn Trp Leu Val Glu Val Pro Thr Val Ser Pro Ile Ser Arg Phe
                180                 185                 190
Thr Tyr His Met Val Ser Gly Met Ser Leu Arg Pro Arg Val Asn Tyr
                195                 200                 205
Leu Gln Asp Phe Ser Tyr Gln Arg Ser Leu Lys Phe Arg Pro Lys Gly
    210                 215                 220
Lys Pro Cys Pro Lys Glu Ile Pro Lys Glu Ser Lys Asn Thr Glu Val
225                 230                 235                 240
Leu Val Trp Glu Glu Cys Val Ala Asn Ser Ala Val Ile Leu Gln Asn
                245                 250                 255
Asn Glu Phe Gly Thr Ile Ile Asp Trp Ala Pro Arg Gly Gln Phe Tyr
                260                 265                 270
His Asn Cys Ser Gly Gln Thr Gln Ser Cys Pro Ser Ala Gln Val Ser
    275                 280                 285
Pro Ala Val Asp Ser Asp Leu Thr Glu Ser Leu Asp Lys His Lys His
    290                 295                 300
Lys Lys Leu Gln Ser Phe Tyr Pro Trp Glu Trp Gly Glu Lys Arg Ile
305                 310                 315                 320
Ser Thr Pro Arg Pro Lys Ile Val Ser Pro Val Ser Gly Pro Glu His
                325                 330                 335
Pro Glu Leu Trp Arg Leu Thr Val Ala Ser His His Ile Arg Ile Trp
                340                 345                 350
Ser Gly Asn Gln Thr Leu Glu Thr Arg Asp Arg Lys Pro Phe Tyr Thr
                355                 360                 365
Val Asp Leu Asn Ser Ser Leu Thr Leu Pro Leu Gln Ser Cys Val Lys
    370                 375                 380
Pro Pro Tyr Met Leu Val Val Gly Asn Ile Val Ile Lys Pro Asp Ser
385                 390                 395                 400
Gln Thr Ile Thr Cys Glu Asn Cys Arg Leu Leu Thr Cys Ile Asp Ser
                405                 410                 415
Thr Phe Asn Trp Gln His Arg Ile Leu Leu Val Arg Ala Arg Glu Gly
                420                 425                 430
```

```
Val Trp Ile Pro Val Ser Met Asp Arg Pro Trp Glu Ala Ser Pro Ser
            435                 440                 445

Val His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Gly Gln Lys Asn Ser Thr Arg Leu Trp
                500                 505                 510

Asn Ser Gln Ser Ser Ile Asp Gln Lys Leu Ala Asn Gln Ile Asn Asp
                515                 520                 525

Leu Arg Gln Thr Val Ile Trp Met Gly Asp Arg Leu Met Ser Leu Glu
    530                 535                 540

His Arg Phe Gln Leu Gln Cys Asp Trp Asn Thr Ser Asp Phe Cys Ile
545                 550                 555                 560

Thr Pro Gln Ile Tyr Asn Asp Ser Glu His His Trp Asp Met Val Arg
                565                 570                 575

Arg His Leu Gln Gly Arg Glu Asp Asn Leu Thr Leu Asp Ile Ser Lys
                580                 585                 590

Leu Lys Glu Gln Ile Phe Glu Ala Ser Lys Ala His Leu Asn Leu Val
    595                 600                 605

Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
                645                 650                 655

Cys Thr Gln Gln Leu Arg Arg Asp Ser Asp His Arg Glu Arg Ala Met
                660                 665                 670

Met Thr Met Ala Val Leu Ser Lys Arg Lys Gly Gly Asn Val Gly Lys
            675                 680                 685

Ser Lys Arg Asp Gln Ile Val Thr Val Ser Val
            690                 695

<210> SEQ ID NO 83
<211> LENGTH: 78
<212> TYPE: PRT
<213> ORGANISM: Gorilla gorilla gorilla

<400> SEQUENCE: 83

Gln Phe Tyr Tyr Lys Leu Ser Gln Glu Leu Asn Gly Asp Met Glu Arg
1               5                   10                  15

Val Ala Asp Ser Leu Val Thr Leu Gln Asp Gln Leu Asn Ser Leu Ala
                20                  25                  30

Ala Val Val Leu Gln Asn Arg Arg Ala Leu Asp Leu Leu Thr Ala Glu
            35                  40                  45

Arg Gly Gly Thr Cys Leu Phe Leu Gly Glu Glu Cys Cys Tyr Tyr Val
    50                  55                  60

Asn Gln Ser Gly Ile Val Thr Glu Lys Val Lys Glu Ile Arg
65                  70                  75

<210> SEQ ID NO 84
<211> LENGTH: 78
<212> TYPE: PRT
```

<213> ORGANISM: Homo sapiens

<400> SEQUENCE: 84

Gln Phe Tyr Tyr Lys Leu Ser Gln Glu Leu Asn Gly Asp Met Glu Arg
1               5                   10                  15

Val Ala Asp Ser Leu Val Thr Leu Gln Asp Gln Leu Asn Ser Leu Ala
            20                  25                  30

Ala Val Val Leu Gln Asn Arg Arg Ala Leu Asp Leu Leu Thr Ala Glu
        35                  40                  45

Arg Gly Gly Thr Cys Leu Phe Leu Gly Glu Glu Cys Cys Tyr Tyr Val
    50                  55                  60

Asn Gln Ser Gly Ile Val Thr Glu Lys Val Lys Glu Ile Arg
65                  70                  75

<210> SEQ ID NO 85
<211> LENGTH: 78
<212> TYPE: PRT
<213> ORGANISM: Ailuropoda melanoleuca

<400> SEQUENCE: 85

Asn Phe Tyr Tyr Lys Leu Ser Gln Ala Leu Asn Asp Asp Met Glu Arg
1               5                   10                  15

Ile Ala Asp Ser Leu Thr Ala Leu Gln Thr Gln Val Thr Ser Leu Ala
            20                  25                  30

Ala Ile Ala Leu Gln Asn Arg Arg Ala Leu Asp Leu Leu Thr Ala Glu
        35                  40                  45

Lys Gly Gly Thr Cys Leu Tyr Leu Asn Glu Glu Cys Cys Tyr Phe Ile
    50                  55                  60

Asn Gln Ser Gly Ile Val Thr Ser Lys Ile Gln Glu Leu Lys
65                  70                  75

<210> SEQ ID NO 86
<211> LENGTH: 78
<212> TYPE: PRT
<213> ORGANISM: Callithrix jacchus

<400> SEQUENCE: 86

Gln Ala Leu Ala His Leu Ser Ser Gln Leu Gln Thr Ala Ile Asp Asp
1               5                   10                  15

Ser Ala Ala Ser Leu Ala Ser Leu Gln Gln Gln Val Thr Ser Val Ala
            20                  25                  30

Gln Val Ala Leu Gln Asn Arg Arg Ala Leu Asp Leu Leu Thr Ala Glu
        35                  40                  45

Arg Gly Gly Thr Cys Ile Phe Leu Gln Glu Glu Cys Cys Tyr Tyr Ile
    50                  55                  60

Asn Glu Ser Gly Ile Val Glu Thr Arg Ile Glu Asn Leu Gln
65                  70                  75

<210> SEQ ID NO 87
<211> LENGTH: 76
<212> TYPE: PRT
<213> ORGANISM: Homo sapiens

<400> SEQUENCE: 87

Ser Ser Gln Asp Leu Ser Ile Lys Leu Gln Met Ala Ile Glu Ala Ser
1               5                   10                  15

Ala Glu Ser Leu Ala Ser Leu Gln Arg Gln Ile Thr Ser Val Ala Lys
            20                  25                  30

Val Ala Met Gln Asn Arg Arg Ala Leu Asp Leu Leu Thr Ala Asp Lys
            35                  40                  45

Gly Gly Thr Cys Met Phe Leu Gly Glu Glu Cys Cys Tyr Tyr Ile Asn
 50                  55                  60

Glu Ser Gly Leu Val Glu Thr Ser Leu Leu Thr Leu
 65                  70                  75

<210> SEQ ID NO 88
<211> LENGTH: 77
<212> TYPE: PRT
<213> ORGANISM: Pan troglodytes

<400> SEQUENCE: 88

Glu Ser Asn Lys Leu Tyr Gln Gln Phe Ala Val Ala Met Glu Glu Ser
 1               5                  10                  15

Ala Glu Ser Leu Ala Ser Leu Gln Arg Gln Leu Thr Ser Leu Ala Gln
            20                  25                  30

Val Thr Leu Gln Asn Arg Arg Ala Leu Asp Leu Leu Thr Ala Glu Lys
            35                  40                  45

Gly Gly Thr Cys Met Phe Leu Lys Glu Asp Cys Cys Phe Tyr Ile Asn
 50                  55                  60

Glu Ser Gly Leu Val Glu Asp Arg Val Gln Gln Leu Arg
 65                  70                  75

<210> SEQ ID NO 89
<211> LENGTH: 77
<212> TYPE: PRT
<213> ORGANISM: Mus musculus

<400> SEQUENCE: 89

Tyr Phe Gln Gln Leu Ser Lys Val Leu Ser Glu Thr Leu Glu Glu Ile
 1               5                  10                  15

Ala Ala Ser Ile Thr Thr Leu Gln Asn Gln Ile Asp Ser Leu Ala Gly
            20                  25                  30

Val Val Leu Gln Asn Arg Arg Ala Leu Asp Leu Ile Thr Ala Glu Lys
            35                  40                  45

Gly Gly Thr Cys Leu Phe Leu Gly Glu Glu Cys Cys Phe Tyr Val Asn
 50                  55                  60

Gln Ser Gly Ile Val Arg Asp Ala Ala Arg Lys Leu Gln
 65                  70                  75

<210> SEQ ID NO 90
<211> LENGTH: 78
<212> TYPE: PRT
<213> ORGANISM: Homo sapiens

<400> SEQUENCE: 90

Thr Thr Phe Arg Ile Leu Ser Asn Asp Phe Ser Ala Ser Ile Thr Asp
 1               5                  10                  15

Ile Ser Gln Thr Leu Ser Gly Leu Gln Ala Gln Val Asp Ser Ser Ala
            20                  25                  30

Ala Val Val Leu Gln Asn Arg Gln Gly Leu Asp Leu Leu Thr Ala Glu
            35                  40                  45

Lys Gly Gly Leu Cys Ile Phe Leu Asn Glu Glu Ser Tyr Phe Tyr Leu
            50                  55                  60

Asn Gln Ser Gly Leu Val Tyr Asp Asn Ile Lys Lys Leu Lys
 65                  70                  75

```
<210> SEQ ID NO 91
<211> LENGTH: 78
<212> TYPE: PRT
<213> ORGANISM: Homo sapiens

<400> SEQUENCE: 91

Met Thr Phe Arg Ser Leu Ser Asn Asp Phe Ser Ala Ser Ile Thr Asp
1               5                   10                  15

Ile Ser Gln Thr Leu Ser Val Leu Gln Ala Gln Val Asp Ser Leu Ala
                20                  25                  30

Ala Val Val Leu Gln Asn Arg Arg Gly Leu Asp Leu Leu Thr Ala Glu
            35                  40                  45

Lys Gly Gly Leu Cys Ile Phe Leu Asn Glu Glu Cys Cys Phe Tyr Leu
50                  55                  60

Asn Gln Ser Gly Leu Val Tyr Asp Asn Ile Lys Lys Leu Lys
65                  70                  75

<210> SEQ ID NO 92
<211> LENGTH: 77
<212> TYPE: PRT
<213> ORGANISM: Gorilla gorilla gorilla

<400> SEQUENCE: 92

Thr Tyr Ser Gln Leu Ser Lys Glu Ile Ala Asn Asn Ile Asp Thr Met
1               5                   10                  15

Ala Lys Ala Leu Thr Thr Met Gln Glu Gln Ile Asp Ser Leu Ala Ala
                20                  25                  30

Val Val Leu Gln Asn Arg Arg Gly Leu Asp Met Leu Thr Ala Ala Gln
            35                  40                  45

Gly Gly Ile Cys Leu Ala Leu Asp Glu Lys Cys Cys Phe Trp Val Asn
50                  55                  60

Gln Ser Gly Lys Val Gln Asp Asn Ile Arg Gln Leu Leu
65                  70                  75

<210> SEQ ID NO 93
<211> LENGTH: 77
<212> TYPE: PRT
<213> ORGANISM: Homo sapiens

<400> SEQUENCE: 93

Thr Tyr Ser Gln Leu Ser Lys Glu Ile Ala Asn Asn Ile Asp Thr Met
1               5                   10                  15

Ala Lys Ala Leu Thr Thr Met Gln Glu Gln Ile Asp Ser Leu Ala Ala
                20                  25                  30

Val Val Leu Gln Asn Arg Arg Gly Leu Asp Met Leu Thr Ala Ala Gln
            35                  40                  45

Gly Gly Ile Cys Leu Ala Leu Asp Glu Lys Cys Cys Phe Trp Val Asn
50                  55                  60

Gln Ser Gly Lys Val Gln Asp Asn Ile Arg Gln Leu Leu
65                  70                  75

<210> SEQ ID NO 94
<211> LENGTH: 78
<212> TYPE: PRT
<213> ORGANISM: Trichosurus vulpecula

<400> SEQUENCE: 94

His Ser Tyr Ala Lys Leu Ser Asn Gln Leu Ile Asn Asp Val Gln Thr
1               5                   10                  15
```

```
Leu Ser Gly Thr Ile His Asp Leu Gln Asp Gln Ile Asp Ser Leu Ala
            20                  25                  30

Glu Val Val Leu Gln Asn Arg Arg Gly Leu Asp Leu Leu Thr Ala Glu
                35                  40                  45

Gln Gly Gly Ile Cys Leu Ala Leu Gln Glu Lys Cys Cys Phe Tyr Ala
        50                  55                  60

Asn Lys Ser Gly Met Val Arg Asp Lys Ile Lys Lys Leu Gln
65                  70                  75
```

<210> SEQ ID NO 95
<211> LENGTH: 78
<212> TYPE: PRT
<213> ORGANISM: Mus musculus

<400> SEQUENCE: 95

```
Thr Gln Tyr Asn Ile Phe Ser Ser Gln Phe Lys Ser Asn Leu Gln Glu
1               5                   10                  15

Met Thr Glu Thr Val Leu Thr Ile Gln Lys Gln Ile Asp Ser Leu Ala
            20                  25                  30

Ala Val Val Leu Gln Asn Arg Gln Gly Leu Asp Val Leu Ser Ala Lys
                35                  40                  45

Glu Gly Gly Leu Cys Leu Phe Leu Gln Glu Glu Cys Cys Phe Tyr Ile
        50                  55                  60

Asn Gln Ser Gly Arg Ile Val Arg Asn Lys Ile Gln Glu Leu
65                  70                  75
```

<210> SEQ ID NO 96
<211> LENGTH: 78
<212> TYPE: PRT
<213> ORGANISM: Callithrix jacchus

<400> SEQUENCE: 96

```
Gln Asn Phe Lys Ala Leu Ser His Gln Ile Asp Ala Asp Ile Thr His
1               5                   10                  15

Leu Gln Asn Ser Ile Thr Lys Leu Ala Glu Gln Val Asp Ser Leu Ala
            20                  25                  30

Glu Met Val Leu Gln Asn Arg Arg Gly Leu Asp Leu Leu Phe Leu Lys
                35                  40                  45

Glu Gly Gly Leu Cys Ala Ala Leu Gly Glu Gln Cys Cys Phe Tyr Ala
        50                  55                  60

Asn Asn Ser Gly Val Ile Arg Asp Ser Leu Ala Met Val Arg
65                  70                  75
```

<210> SEQ ID NO 97
<211> LENGTH: 77
<212> TYPE: PRT
<213> ORGANISM: Monodelphis domestica

<400> SEQUENCE: 97

```
Ser His Asn His Leu Arg Ala Ala Val Asp Glu Asp Ile Ala Arg Leu
1               5                   10                  15

Glu Ser Thr Ile Asn Phe Leu Glu Lys Ser His Ala Ser Leu Ala Glu
            20                  25                  30

Val Ala Leu Gln Asn Arg Arg Gly Leu Asp Leu Leu Phe Leu Arg Glu
                35                  40                  45

Gly Gly Leu Cys Ala Ala Leu Gly Glu Glu Cys Cys Phe Tyr Ala Asn
        50                  55                  60

His Ser Gly Val Ile Arg Asp Ser Leu Ala Gln Leu Arg
65                  70                  75
```

<210> SEQ ID NO 98
<211> LENGTH: 78
<212> TYPE: PRT
<213> ORGANISM: Homo sapiens

<400> SEQUENCE: 98

Thr Gly Leu Ile Ser Leu Ser Gln Gln Val Asp Ala Asp Phe Ser Asn
1               5                   10                  15

Leu Gln Ser Ala Ile Asp Ile Leu His Ser Gln Val Glu Ser Leu Ala
            20                  25                  30

Glu Val Val Glu Gln Asn Cys Arg Cys Leu Asp Leu Leu Phe Leu Ser
        35                  40                  45

Gln Gly Gly Leu Cys Ala Ala Leu Gly Glu Ser Cys Cys Phe Tyr Ala
    50                  55                  60

Asn Gln Ser Gly Val Ile Lys Gly Thr Val Lys Lys Val Arg
65                  70                  75

<210> SEQ ID NO 99
<211> LENGTH: 67
<212> TYPE: PRT
<213> ORGANISM: Pan troglodytes

<400> SEQUENCE: 99

Val Asp Lys Asp Ile Ser Gln Leu Thr Gln Ala Ile Val Lys Asn His
1               5                   10                  15

Lys Asn Leu Leu Lys Ile Ala Gln Tyr Ala Ala Gln Asn Arg Arg Gly
            20                  25                  30

Leu Asp Leu Leu Phe Trp Glu Gln Gly Gly Leu Cys Lys Ala Leu Gln
        35                  40                  45

Glu Gln Cys Cys Phe Leu Asn Ile Thr Asn Ser His Val Ser Ile Leu
    50                  55                  60

Gln Glu Arg
65

<210> SEQ ID NO 100
<211> LENGTH: 78
<212> TYPE: PRT
<213> ORGANISM: Mus musculus

<400> SEQUENCE: 100

Gln Gln Phe Gln Gln Leu Gln Ala Ala Met His Asn Asp Leu Lys Ala
1               5                   10                  15

Val Glu Glu Ser Ile Thr Asn Leu Glu Arg Ser Leu Thr Ser Leu Ser
            20                  25                  30

Glu Val Val Leu Gln Asn Arg Arg Gly Leu Asp Leu Leu Phe Leu Lys
        35                  40                  45

Glu Gly Gly Leu Cys Ala Ala Leu Lys Glu Glu Cys Cys Phe Tyr Ala
    50                  55                  60

Asp His Thr Gly Leu Val Arg Asp Ser Met Ala Lys Leu Arg
65                  70                  75

<210> SEQ ID NO 101
<211> LENGTH: 77
<212> TYPE: PRT
<213> ORGANISM: Mus musculus

<400> SEQUENCE: 101

Gln Phe Glu Gln Leu Gln Ala Ala Ile His Thr Asp Leu Gly Ala Leu
1               5                   10                  15

Glu Lys Ser Val Ser Ala Leu Gly Lys Ser Leu Thr Ser Leu Ser Glu
            20                  25                  30

Val Val Leu Gln Asn Arg Arg Gly Leu Asp Leu Leu Phe Leu Lys Glu
        35                  40                  45

Gly Gly Leu Cys Ala Ala Leu Lys Glu Glu Cys Cys Phe Tyr Ala Asp
    50                  55                  60

His Ile Gly Val Val Arg Asp Ser Met Thr Lys Leu Arg
65                  70                  75

<210> SEQ ID NO 102
<211> LENGTH: 78
<212> TYPE: PRT
<213> ORGANISM: Monodelphis domestica

<400> SEQUENCE: 102

Asn His Leu Gln Thr Leu His Met Ala Val Asn Glu Asp Leu Gln Arg
1               5                   10                  15

Ile Glu Lys Ser Leu Asp Ala Leu Glu Lys Ser Leu Ser Ser Phe Ser
            20                  25                  30

Glu Val Val Leu Gln Asn His Ser Gly Leu Asn Leu Leu Phe Leu Gln
        35                  40                  45

Glu Gly Gly Leu Cys Val Ala Leu Lys Glu Glu Cys Cys Phe Tyr Ile
    50                  55                  60

Asp His Met Gly Val Val Arg Glu Ser Leu Ala Gln Leu Arg
65                  70                  75

<210> SEQ ID NO 103
<211> LENGTH: 78
<212> TYPE: PRT
<213> ORGANISM: Taeniopygia guttata

<400> SEQUENCE: 103

Gln Glu Leu Gln Ser Leu Gln Thr Ala Val Asp Glu Asp Leu Ala Lys
1               5                   10                  15

Ile Glu Gln Ser Ile Gln Asn Leu Ala Thr Ser Val Lys Ser Leu Ser
            20                  25                  30

Glu Val Val Leu Gln Asn Arg Arg Gly Leu Asp Leu Leu Phe Leu Lys
        35                  40                  45

Glu Gly Gly Leu Cys Val Ala Leu Asn Glu Glu Cys Cys Ser Phe Ala
    50                  55                  60

Asp Asp Thr Gly Val Val Gln Asp Thr Met Ser Glu Leu Trp
65                  70                  75

<210> SEQ ID NO 104
<211> LENGTH: 78
<212> TYPE: PRT
<213> ORGANISM: Mus musculus

<400> SEQUENCE: 104

Gln Gln Tyr Thr Gln Leu His Leu Ala Val Asp Arg Asp Ile Gln Glu
1               5                   10                  15

Leu Gln Arg Gly Leu Lys Asn Leu Lys Asp Ser Leu Val Ser Leu Ser
            20                  25                  30

Glu Val Val Leu Gln Asn Arg Arg Gly Leu Asp Leu Val Phe Leu Lys
        35                  40                  45

Glu Gly Gly Leu Cys Ala Ala Leu Lys Glu Glu Cys Cys Phe Tyr Ser

```
                    50                  55                  60

Asp Lys Ile Gly Leu Val Gln Asp Ser Ile Asp Lys Val Arg
 65                  70                  75

<210> SEQ ID NO 105
<211> LENGTH: 77
<212> TYPE: PRT
<213> ORGANISM: Monodelphis domestica

<400> SEQUENCE: 105

Gly Leu Ser Ala Leu Gly Ala Ala Ala Asp Glu Asp Leu Ala Arg Met
  1               5                  10                  15

Glu Thr Ser Ile Pro Arg Ile Lys Arg Ser Phe Thr Ser Leu Ser Glu
                 20                  25                  30

Val Val Ile Gln Asn Arg Arg Ser Leu Asp Leu Leu Thr Leu His Gln
             35                  40                  45

Arg Gly Leu Cys Ala Met His Gly Met Glu Cys Cys Phe Tyr Ser Asp
         50                  55                  60

His Leu Gly Ala Val Arg Glu Ser Met Ala Lys Leu Arg
 65                  70                  75

<210> SEQ ID NO 106
<211> LENGTH: 78
<212> TYPE: PRT
<213> ORGANISM: Mus musculus

<400> SEQUENCE: 106

Glu Asn Tyr Lys Val Leu Ser Ser Ala Ile Asp Ala Asp Leu Met Glu
  1               5                  10                  15

Leu Gly Lys Ser Leu Ser Lys Ser Lys Thr Ser Leu Thr Ser Leu Arg
                 20                  25                  30

Glu Ala Thr Leu Arg Asn Gln Arg Glu Gln Asp Phe Gln Ser Leu Gln
             35                  40                  45

Gln Asp Gly Leu Cys Lys Pro Leu Glu Lys Arg Cys Cys Thr Phe Val
         50                  55                  60

Asp Asn Leu Lys His Ala Arg Glu Leu Leu Ala Lys Val Arg
 65                  70                  75

<210> SEQ ID NO 107
<211> LENGTH: 72
<212> TYPE: PRT
<213> ORGANISM: Homo sapiens

<400> SEQUENCE: 107

Gln Ile Asp Asn Ile Ala Lys Ser Thr Arg Asp Ser Ile Ser Lys Leu
  1               5                  10                  15

Lys Ala Ser Ile Asp Ser Leu Ala Asn Val Val Met Asn Asn Arg Leu
                 20                  25                  30

Ala Leu Asp Tyr Leu Leu Ala Glu Gln Gly Gly Val Cys Ala Val Ile
             35                  40                  45

Ser Lys Ser Cys Cys Ile Tyr Val Asn Asn Ser Gly Ala Ile Glu Glu
         50                  55                  60

Asp Ile Lys Lys Ile Tyr Asp Glu
 65                  70

<210> SEQ ID NO 108
<211> LENGTH: 72
<212> TYPE: PRT
<213> ORGANISM: Homo sapiens
```

-continued

<400> SEQUENCE: 108

Gln Ile Asp Asn Ile Ala Lys Ser Thr Arg Asp Ser Ile Ser Lys Leu
1               5                   10                  15

Lys Ala Ser Ile Asp Ser Leu Ala Asn Val Val Met Asp Asn Arg Leu
            20                  25                  30

Ala Leu Asp Tyr Leu Leu Ala Glu Gln Gly Gly Val Cys Ala Val Ile
        35                  40                  45

Asn Lys Ser Cys Cys Val Tyr Val Asn Asn Ser Gly Ala Ile Glu Glu
    50                  55                  60

Asp Ile Lys Lys Ile Tyr Asp Glu
65                  70

<210> SEQ ID NO 109
<211> LENGTH: 77
<212> TYPE: PRT
<213> ORGANISM: Danio rerio

<400> SEQUENCE: 109

Tyr Ile His Tyr Asn Val Gln Arg Leu Ser Asn Leu Thr Arg Asp Ala
1               5                   10                  15

Val Ser Gly Leu Lys Glu Gln Leu Ala Ala Thr Ser Leu Met Thr Ile
            20                  25                  30

Gln Asn Arg Leu Ala Leu Asp Met Leu Leu Ser Glu Arg Gly Gly Val
        35                  40                  45

Cys Ser Met Phe Lys Asp Thr Cys Cys Thr Val Ile Pro Asn Asn Thr
    50                  55                  60

Ala Pro Asp Gly Ser Val Ser Arg Ala Leu Glu Gly Leu
65                  70                  75

<210> SEQ ID NO 110
<211> LENGTH: 77
<212> TYPE: PRT
<213> ORGANISM: Homo sapiens

<400> SEQUENCE: 110

Tyr Ile Tyr Tyr Asn Gln Gln Arg Phe Ile Asn Tyr Thr Arg Asp Ala
1               5                   10                  15

Ile Gln Gly Ile Ala Glu Gln Leu Gly Pro Thr Ser Gln Met Ala Trp
            20                  25                  30

Glu Asn Arg Met Ala Leu Asp Met Ile Leu Ala Glu Lys Gly Gly Val
        35                  40                  45

Cys Val Met Ile Gly Thr Asp Cys Cys Thr Tyr Ile Pro Asn Asn Thr
    50                  55                  60

Ala Pro Asp Gly Thr Ile Thr Lys Ala Leu Gln Gly Leu
65                  70                  75

<210> SEQ ID NO 111
<211> LENGTH: 74
<212> TYPE: PRT
<213> ORGANISM: Homo sapiens

<400> SEQUENCE: 111

Ala Leu Ala Asn Phe Thr Gln Arg Ala Leu Asn Asp Ser Leu Gln Ser
1               5                   10                  15

Ile Ser Leu Met Asn Ala Glu Val Tyr Tyr Met His Glu Asp Ile Leu
            20                  25                  30

Gln Asn Arg Met Ala Leu Asp Ile Leu Thr Ala Ala Glu Gly Gly Thr

-continued

```
                35                  40                  45
Cys Ala Leu Ile Lys Thr Glu Cys Cys Val Tyr Ile Pro Asn Asn Ser
        50                  55                  60
Arg Asn Ile Ser Leu Ala Leu Glu Asp Thr
65                  70

<210> SEQ ID NO 112
<211> LENGTH: 72
<212> TYPE: PRT
<213> ORGANISM: Gallus gallus

<400> SEQUENCE: 112

Trp Ser Val Lys Gln Ala Asn Leu Thr Ser Leu Ile Leu Asn Ala Met
1               5                   10                  15

Leu Glu Asp Thr Ser Ser Ile Arg His Ala Val Leu Gln Asn Arg Ala
            20                  25                  30

Ala Ile Asp Phe Leu Leu Leu Ala Gln Gly His Gly Cys Gln Asp Val
        35                  40                  45

Glu Gly Met Cys Cys Phe Asn Leu Ser Asp His Ser Glu Ser Ile His
    50                  55                  60

Lys Ala Leu Gln Ala Met Lys Glu
65                  70

<210> SEQ ID NO 113
<211> LENGTH: 73
<212> TYPE: PRT
<213> ORGANISM: Taeniopygia guttata

<400> SEQUENCE: 113

Trp Val Asn Lys Asn Ala Asn Ala Thr Ser Ala Ala Leu Ser Asp Leu
1               5                   10                  15

Leu Ala Asp Glu Gln Thr Thr Arg His Ala Thr Leu Gln Asn Arg Ala
            20                  25                  30

Ala Ile Asp Phe Leu Leu Leu Ala His Gly His Ser Cys Glu Asp Phe
        35                  40                  45

Asp Gly Leu Cys Cys Phe Asn Leu Ser Ser Arg Ser Lys Ser Ile Gln
    50                  55                  60

Ala His Ile Gln Gln Ile Arg Glu Gln
65                  70

<210> SEQ ID NO 114
<211> LENGTH: 50
<212> TYPE: PRT
<213> ORGANISM: Xenopus tropicalis

<400> SEQUENCE: 114

Ile Ile Val Lys Ser Ile Asn Ala Ala Ser Ile Ala Ile Ala Asn Leu
1               5                   10                  15

Leu Pro Asp Ile Gly Asp Ala Arg Lys Ala Val Leu Gln Asn Arg Ala
            20                  25                  30

Ala Ile Asn Tyr Leu Phe Phe Lys His Asn His Gly Cys Glu Tyr Phe
        35                  40                  45

Glu Gly
    50

<210> SEQ ID NO 115
<211> LENGTH: 74
<212> TYPE: PRT
<213> ORGANISM: Homo sapiens
```

-continued

```
<400> SEQUENCE: 115

Ile Leu Glu Ile Ile Ser Asn Glu Thr Gly Arg Ala Leu Thr Val Leu
1               5                   10                  15

Ala Trp Gln Glu Thr Gln Met Arg Asn Ala Ile Tyr Gln Asn Arg Leu
                20                  25                  30

Ala Leu Asp Tyr Leu Leu Val Ala Glu Gly Gly Val Cys Arg Lys Phe
            35                  40                  45

Asn Leu Thr Asn Cys Cys Leu Gln Ile Asn Asp Gln Gly Gln Val Val
        50                  55                  60

Lys Asn Ile Val Arg Asp Met Thr Lys Val
65                  70

<210> SEQ ID NO 116
<211> LENGTH: 74
<212> TYPE: PRT
<213> ORGANISM: Homo sapiens

<400> SEQUENCE: 116

Val Leu Glu Ile Ile Thr Asn Glu Thr Ala Gly Ala Leu Asn Leu Leu
1               5                   10                  15

Ala Gln Gln Ala Thr Lys Met Arg Asn Val Ile Tyr Gln Asn Arg Leu
                20                  25                  30

Ala Leu Asp Tyr Leu Leu Ala Gln Glu Glu Gly Val Cys Gly Lys Phe
            35                  40                  45

Asn Leu Thr Asn Cys Cys Leu Glu Leu Asp Asp Glu Gly Lys Val Ile
        50                  55                  60

Lys Glu Ile Thr Ala Lys Ile Gln Lys Leu
65                  70

<210> SEQ ID NO 117
<211> LENGTH: 74
<212> TYPE: PRT
<213> ORGANISM: Taeniopygia guttata

<400> SEQUENCE: 117

Val Val Glu Ile Val Ser Asn His Thr Ser Asp Ala Leu Glu Leu Leu
1               5                   10                  15

Ser Gln Gln His Ser Gln Met Arg Ala Phe Val Tyr Gln Asn Arg Ile
                20                  25                  30

Ala Leu Asp Tyr Leu Leu Ala Gly Glu Gly Gly Val Cys Gly Lys Phe
            35                  40                  45

Asn Glu Ser Gln Cys Cys Val Glu Ile Asp Asp Tyr Gly Glu Thr Ile
        50                  55                  60

Arg Asp Leu Ala Thr Glu Ile Lys Arg Val
65                  70

<210> SEQ ID NO 118
<211> LENGTH: 72
<212> TYPE: PRT
<213> ORGANISM: Gallus gallus

<400> SEQUENCE: 118

Thr Leu Glu Ile Val Glu Asn Ala Thr Thr Asp Ala Leu Arg Ala Ile
1               5                   10                  15

Gln Glu Glu Val Ser Ser Leu Ser Lys Val Val Leu Gln Asn Arg Met
                20                  25                  30

Ala Leu Asp Leu Leu Thr Ala Lys Glu Gly Gly Val Cys Thr Ile Ile
```

-continued

```
                35                  40                  45
Asn Gln Ser Cys Cys Ala Tyr Ile Asn Lys Asp Leu Arg Ile Glu Thr
        50                  55                  60
Asp Leu Arg Lys Ile Trp Glu Gln
65                  70

<210> SEQ ID NO 119
<211> LENGTH: 82
<212> TYPE: PRT
<213> ORGANISM: Homo sapiens

<400> SEQUENCE: 119

Val Asn Tyr Trp Gln Lys Asn Ser Thr Arg Leu Trp Asn Ser Gln Ser
1               5                   10                  15

Ser Ile Asp Gln Lys Leu Ala Ser Gln Ile Asn Asp Leu Arg Gln Thr
                20                  25                  30

Val Ile Trp Met Gly Asp Arg Leu Met Thr Leu Glu His His Phe Gln
            35                  40                  45

Leu Gln Cys Asp Trp Asn Thr Ser Asp Phe Cys Ile Thr Pro Gln Ile
        50                  55                  60

Tyr Asn Glu Ser Glu His His Trp Asp Met Val Arg Arg His Leu Gln
65                  70                  75                  80

Gly Arg

<210> SEQ ID NO 120
<211> LENGTH: 82
<212> TYPE: PRT
<213> ORGANISM: Homo sapiens

<400> SEQUENCE: 120

Val Asn Asp Trp Gln Lys Asn Ser Thr Arg Leu Trp Asn Ser Gln Ser
1               5                   10                  15

Ser Ile Asp Gln Lys Leu Ala Asn Gln Ile Asn Asp Leu Arg Gln Thr
                20                  25                  30

Val Ile Trp Met Gly Asp Arg Leu Met Ser Leu Glu His Arg Phe Gln
            35                  40                  45

Leu Gln Cys Asp Trp Asn Thr Ser Asp Phe Cys Ile Thr Pro Gln Ile
        50                  55                  60

Tyr Asn Glu Ser Glu His His Trp Asp Met Val Arg Arg His Leu Gln
65                  70                  75                  80

Gly Arg

<210> SEQ ID NO 121
<211> LENGTH: 82
<212> TYPE: PRT
<213> ORGANISM: Bos taurus

<400> SEQUENCE: 121

Ile Thr Ala Trp His Lys Asp Ser His Asn Leu Trp Thr Gln Gln Ala
1               5                   10                  15

Gln Ile Asp Gln Gln Leu Gln Thr Arg Ile Asn Glu Leu Gln Thr Val
                20                  25                  30

Val Ile Asn Ile Gly Asp Gln Val Gln Gln Leu Thr Phe Leu Thr His
            35                  40                  45

Ile Cys Cys His Trp Asn Phe Thr Ser Phe Cys Leu Thr Asn Met Pro
        50                  55                  60

Tyr Asn Gly Thr Glu Tyr Pro Trp Asp Lys Val Lys Val His Phe Gln
```

65 70 75 80

Asp Leu

<210> SEQ ID NO 122
<211> LENGTH: 81
<212> TYPE: PRT
<213> ORGANISM: Homo sapiens

<400> SEQUENCE: 122

Val Asn Asn Leu His Arg Asn Val Thr Leu Ala Leu Ser Glu Gln Arg
1 5 10 15

Ile Ile Asp Leu Lys Leu Glu Ala Arg Leu Asn Ala Leu Glu Glu Val
20 25 30

Val Leu Glu Leu Gly Gln Asp Val Ala Asn Leu Lys Thr Arg Met Ser
35 40 45

Thr Arg Cys His Ala Asn Tyr Asp Phe Ile Cys Val Thr Pro Leu Pro
50 55 60

Tyr Asn Ala Ser Glu Ser Trp Glu Arg Thr Lys Ala His Leu Leu Gly
65 70 75 80

Ile

<210> SEQ ID NO 123
<211> LENGTH: 82
<212> TYPE: PRT
<213> ORGANISM: Ovis aries

<400> SEQUENCE: 123

Val Asp Ser Leu Ser Tyr Asn Val Thr Lys Val Met Gly Thr Gln Glu
1 5 10 15

Asp Ile Asp Lys Lys Ile Glu Asp Arg Leu Ser Ala Leu Tyr Asp Val
20 25 30

Val Arg Val Leu Gly Glu Gln Val Gln Ser Ile Asn Phe Arg Met Lys
35 40 45

Ile Gln Cys His Ala Asn Tyr Lys Trp Ile Cys Val Thr Lys Lys Pro
50 55 60

Tyr Asn Thr Ser Asp Phe Pro Trp Asp Lys Val Lys Lys His Leu Gln
65 70 75 80

Gly Ile

<210> SEQ ID NO 124
<211> LENGTH: 80
<212> TYPE: PRT
<213> ORGANISM: artificial
<220> FEATURE:
<223> OTHER INFORMATION: consensus HTLV-1-like HR1-HR2 domain sequence

<400> SEQUENCE: 124

Gln Tyr Asn Gln Leu Ser Lys Ala Val Asp Asn Asp Ile Asn Glu Thr
1 5 10 15

Ala Asp Ser Leu Ser Lys Leu Gln Gln Leu Ser Leu Ala Glu Val Val
20 25 30

Leu Gln Asn Arg Arg Ala Leu Asp Leu Leu Thr Ala Glu Glu Gly Gly
35 40 45

Leu Cys Ala Ala Leu Asn Glu Glu Cys Cys Phe Tyr Ile Pro Tyr Asn
50 55 60

Gln Ser Gly Arg Val Val Arg Asp Ser Ile Lys Lys Leu Arg Gly Leu
65 70 75 80

```
<210> SEQ ID NO 125
<211> LENGTH: 16
<212> TYPE: PRT
<213> ORGANISM: artificial
<220> FEATURE:
<223> OTHER INFORMATION: consensus CKS-17 and CX(6)C domain sequence

<400> SEQUENCE: 125

Leu Gln Asn Arg Arg Leu Asp Leu Leu Thr Ala Glu Lys Gly Gly Leu
1               5                   10                  15
```

COMPOSITIONS AND METHODS INVOLVING ENDOGENOUS RETROVIRUS PROTEINS

CROSS-REFERENCE TO RELATED APPLICATION

This application is the § 371 U.S. National Stage of International Application No. PCT/US2014/012964, filed 24 Jan. 2014, which claims priority to U.S. Provisional Patent Application Ser. No. 61/756,937, filed Jan. 25, 2013, each of which is incorporated herein by reference.

This application contains a Sequence Listing electronically submitted to the United States Patent and Trademark Office via EFS-Web as an ASCII text file entitled "2015-07-22_USNatlStage-SeqList_ST25_PTO.txt" having a size of 134 KB and created on Jul. 22, 2015. Due to the electronic filing of the Sequence Listing, the electronically submitted Sequence Listing serves as both the paper copy required by 37 CFR § 1.821(c) and the CRF required by §1.821(e). The information contained in the Sequence Listing is incorporated by reference herein and does not go beyond the disclosure in the Application as filed.

SUMMARY

This disclosure describes, in one aspect, a method of slowing cellular growth. Generally, the method includes increasing expression of an endogenous retrovirus envelope protein in at least one cell, wherein the cell expresses p53 and expression of the retrovirus envelope protein is controlled by p53; and exposing the cell to conditions that upregulate expression of p53.

This disclosure also describes a method of decreasing cell viability. Generally, this method includes increasing expression of an endogenous retrovirus envelope protein in at least one cell, wherein the cell expresses p53 and expression of the retrovirus envelope protein is controlled by p53; and exposing the cell to conditions that upregulate expression of p53.

In either case, in certain embodiments, the conditions that upregulate expression of p53 can include cellular stress. In some embodiments, increasing expression of an endogenous envelope protein can include overexpressing the endogenous envelope protein. In some of these embodiments, overexpressing the endogenous envelope protein can include introducing into the cell a polynucleotide that includes a coding region that encodes a functional portion of the endogenous envelope protein operably linked to a p53 response element. In some of these embodiments, the p53 response element can include the polynucleotide sequence reflected in SEQ ID NO:1. In other embodiments, the p53 response element can include at least 10 contiguous nucleotides of any one of: nucleotides 10-19 of SEQ ID NO:2, nucleotides 47-56 of SEQ ID NO:2, nucleotides 88-100 of SEQ ID NO:2, nucleotides 334-344 of SEQ ID NO:2, nucleotides 419-430 of SEQ ID NO:2, nucleotides 473-486 of SEQ ID NO:2, nucleotides 548-560 of SEQ ID NO:2, nucleotides 607-618 of SEQ ID NO:2, or nucleotides 679-690 of SEQ ID NO:2. In still other embodiments, the p53 response element can include nucleotides 169-179 of SEQ ID NO:3, nucleotides 246-255 of SEQ ID NO:3, nucleotides 337-346 of SEQ ID NO:3, nucleotides 371-380 of SEQ ID NO:3, nucleotides 460-469 of SEQ ID NO:3, nucleotides 524-533 of SEQ ID NO:3, nucleotides 588-597 of SEQ ID NO:3, nucleotides 786-795 of SEQ ID NO:3, nucleotides 800-809 of SEQ ID NO:3, nucleotides 892-901 of SEQ ID NO:3, or nucleotides 1122-1131 of SEQ ID NO:3.

In another aspect, this disclosure describes a composition that includes a polynucleotide that includes a coding region that encodes a functional portion of the endogenous envelope protein operably linked to a p53 response element. In some embodiments, the p53 response element can include the polynucleotide sequence reflected in SEQ ID NO:1. In other embodiments, the p53 response element can include at least 10 contiguous nucleotides of any one of: nucleotides 10-19 of SEQ ID NO:2, nucleotides 47-56 of SEQ ID NO:2, nucleotides 88-100 of SEQ ID NO:2, nucleotides 334-344 of SEQ ID NO:2, nucleotides 419-430 of SEQ ID NO:2, nucleotides 473-486 of SEQ ID NO:2, nucleotides 548-560 of SEQ ID NO:2, nucleotides 607-618 of SEQ ID NO:2, or nucleotides 679-690 of SEQ ID NO:2. In still other embodiments, the p53 response element can include nucleotides 169-179 of SEQ ID NO:3, nucleotides 246-255 of SEQ ID NO:3, nucleotides 337-346 of SEQ ID NO:3, nucleotides 371-380 of SEQ ID NO:3, nucleotides 460-469 of SEQ ID NO:3, nucleotides 524-533 of SEQ ID NO:3, nucleotides 588-597 of SEQ ID NO:3, nucleotides 786-795 of SEQ ID NO:3, nucleotides 800-809 of SEQ ID NO:3, nucleotides 892-901 of SEQ ID NO:3, or nucleotides 1122-1131 of SEQ ID NO:3. In any of these embodiments, the composition can further include a delivery vehicle.

In another aspect, this disclosure describes a composition that includes antibody that specifically binds to an endogenous retrovirus envelope protein. In some embodiments, the endogenous envelope protein can include HENV-R, HENV-W, HENV-V1, HENV-V2, HENV-F(c)1, HENV-F(c)2, HENV-FRD, HENV-R(b), HENV-H2, HENV-H1, HENV-H3 HENV-K (1q23.3), HENV-K1 (12q14.1), HENV-T, ABB52637, hCG2039029, or Q4KWC9. In some embodiments, the antibody can include a monoclonal antibody. In some embodiments, the antibody can include polyclonal antibodies.

In yet another aspect, this disclosure describes a method of identifying a subject as at risk of having cancer. Generally, the method includes obtaining a biological sample from a subject comprising cells from at least one tissue, analyzing the cells for expression of an endogenous retrovirus envelope protein, and identifying the subject as having or at risk of having cancer if the cells express the endogenous retrovirus envelope protein. In some embodiments, the tissue can include tissue of the ovary, colorectum, esophagus, head and neck, larynx, lung, skin, pancreas, stomach, liver, brain, bladder, breast, uterus, soft tissues, lymph nodes, prostate, bones endocrine glands, the hematopoietic system, or cervix. In particular embodiments, the tissue can include tissue of the human breast or tissue of the human prostate. In some embodiments, the endogenous retrovirus envelope protein can include HENV-R, HENV-W, HENV-V1, HENV-V2, HENV-F(c)1, HENV-FRD, HENV-R(b), HENV-H (3q26), HENV-H (2q24.3), HENV-K (1q23.3), HENV-K (12q14.1), HENV-T, ABB52637, hCG2039029, or Q4KWC9. In some embodiments, the method can further include providing the subject a treatment effective for treating cancer.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 3. The 5' LTR of HERV-W contains putative p53 response elements. Nucleotides in light shading reflect nucleotide matches with the consensus p53 response element sequence; nucleotides in dark shading indicate variation from the consensus p53 response element sequence.

FIG. 4. Mmergln-int is an endogenous retrovirus with intact gag, pol, and env coding regions.

FIG. 12. The 5' LTR of hERV-FRD contains putative p53 response elements. Nucleotides in light shading reflect nucleotide matches with the consensus p53 response element sequence; nucleotides in dark shading indicate variation from the consensus p53 response element sequence.

FIG. 16. Conserved HTLV-1-like HR1-HR2 domain in 16 coding competent human retroelements.

FIG. 18. Highly conserved CKS-17 and CX(6)C domains in HERV and Mmergln-int ENV sequences with potential therapeutic consequences. Sequences shown include CKS-17 and CX(6)C domains from ENV-R (residues 524-593 of SEQ ID NO:75), ENV-R(b) (residues 354-427 of SEQ ID NO:76), ENV-T (residues 479-550 of SEQ ID NO:71), Mmergln-int envelope (residues 493-564 of SEQ ID NO:66), ENVF(c)-1 (residues 425-496 of SEQ ID NO:69), ENVF(c)-2 (residues 452-524 of SEQ ID NO:70), ENVW-1 (residues 356-427 of SEQ ID NO:67), ENVFRD-1 (residues 390-461 of SEQ ID NO:68), ENV-H2 (residues 430-501 of SEQ ID NO:73), ENV-H1 (residues 430-501 of SEQ ID NO:72), and ENV-H3 (residues 430-493 of SEQ ID NO:74). A consensus sequence is also shown (SEQ ID NO:125).

DETAILED DESCRIPTION OF ILLUSTRATIVE EMBODIMENTS

Figure 1:
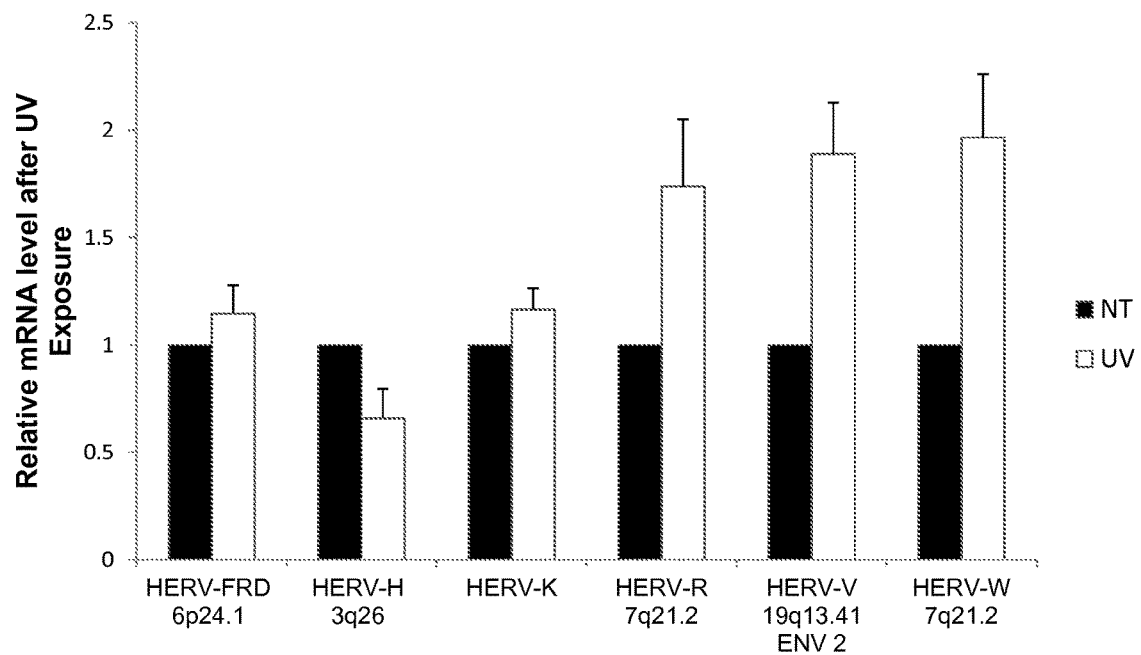
FIG. 1. Identification of hERVs transcriptionally upregulated after UV exposure in Mcf7 cells.

This disclosure describes compositions and methods that reflect the observation that expression of endogenous retroviruses (ERVs) can decrease cell viability and/or limit cell growth. Thus, exploiting this feature of endogenous retroviruses can provide a basis for therapeutic compositions and methods for use in treating conditions of uncontrolled cell growth including, for example, neoplastic conditions such as various forms of cancer.

Endogenous retroviruses (ERVs) are polynucleotide sequences that are derived from retroviruses that have integrated into the genome of a vertebrate organism. The standard replication cycle of a retrovirus includes insertion of the retroviral DNA into the genome of the infected host cell. If the retrovirus integrates into germline cells, the integrated retrovirus may be passed on to subsequent generations, thus becoming an endogenous retrovirus.

If an endogenous retrovirus is active, it can relocate within the genome. In some cases, cancer may be caused by an endogenous retrovirus inserting into and disrupting a coding region that controls cell growth and inhibits cancer if not affected by the endogenous retrovirus. Global epigenetic changes that occur during cancer can reactivate an endogenous retrovirus so that elevated expression of the endogenous retrovirus is detectable.

The tumor suppressor p53 activates portions of the genome involved in apoptosis, senescence, and cell cycle arrest in response to cellular stress. One function of p53 is its role as a transcription factor, and the characterization of genes activated by p53 provides insight into mechanisms of tumor suppression. Although the identification of p53 target genes is common in cancer research, discerning the role of p53 in regulating non-genic regions of the genome is not.

We began by studying the role of p53 in regulating non-genic regions of the genome and discovered that p53, in addition to regulating expression of certain cancer genes, also regulates expression of non-genic regions such as, for example, endogenous retroviruses. We then discovered that endogenous retrovirus expression directly affects cell viability and can serve as a marker for elevated p53 expression.

This disclosure describes expression of endogenous retroviruses being induced by cellular stress. When induced in this manner, endogenous retrovirus expression can decrease cell viability and/or limit cell growth and, consequently, can serve as a suppressor of tumor growth.

Thus, in one aspect, this disclosure describes methods and compositions that exploit endogenous retrovirus expression in either early cellular stages (as opposed to clinical stages) of cancer or in later cellular stages of cancer (which encompass all clinical stages of cancer). In early cellular stages of cancer, in which a subject typically does not experience any symptoms or exhibit any clinical signs of cancer, endogenous retrovirus expression can be used to limit pre-cancerous cell growth. That is, during this cellular stage, expression of endogenous retroviruses is involved in natural pathways of cell death. One cause of cancer is disruption of these pathways so that cells ignore programmed cell death signals and persist. Increasing endogenous retrovirus expression at this stage can help reinforce natural programmed cell death pathways and decrease the likelihood that cells persist to become neoplastic.

In later cellular stages, endogenous retrovirus expression can serve as a tumor antigen and may, therefore, serve as a diagnostic marker of cancer or as a therapeutic target for, for example, therapeutic immunotherapy. Endogenous retrovirus expression is typically regulated by p53 so that elevated p53 expression may be reflected by elevated expression of the ERV. Moreover, endogenous retrovirus envelope polypeptides typically may be expressed on the surface of a cell expressing the ERV. Thus, the endogenous retrovirus envelope polypeptide can be a cell surface marker of elevated p53 expression inside the cell.

As used herein, the following terms shall have the indicated meanings:

"Antigen" and variations thereof refer to any material capable of raising an immune response in a subject challenged with the material. In various embodiments, an antigen may raise a cell-mediated immune response, a humoral immune response, or both. Suitable antigens may be synthetic or occur naturally and, when they occur naturally, may be endogenous (e.g., a self-antigen) or exogenous.

"At risk" refers to a subject that may or may not actually possess the described risk. Thus, for example, a subject "at risk" for developing a specified condition is a subject that possesses one or more indicia of increased risk of having or developing the specified condition compared to individuals who lack the one or more indicia, regardless of the whether the subject manifests any symptom or clinical sign of having or developing the condition. "Sign" or "clinical sign" refers to an objective physical finding relating to a particular condition capable of being found by one other than the patient. "Symptom" refers to any subjective evidence of disease or of a patient's condition.

"Coding region" refers to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Regulatory sequences include, for example, promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

"Express" and variations thereof refer to the conversion of genetic information in a nucleotide sequence to a gene product. Expression of a polynucleotide sequence (e.g., a gene) may be measured and/or described with reference to (a) transcription of DNA to mRNA, (b) translation of mRNA to protein, (c) post-translational steps (e.g., modification of the primary amino acid sequence; addition of a carbohydrate, a lipid, a nucleotide, or other moiety to the protein; assembly of subunits; insertion of a membrane-associated protein into a biological membrane; and the like), or any combination of the foregoing.

"Polypeptide" and "protein refer to a sequence of amino acid residues without regard to the length of the sequence. Therefore, the terms "polypeptide" and "protein" may be used interchangeably to refer to any amino acid sequence having at least two amino acids and may refer to a full-length protein, a fragment thereof, and/or, as the case may be, a polyprotein.

"Specific" and variations thereof refer to having a differential or a non-general (i.e., non-specific) affinity, to any degree, for a particular target.

"Treat" or variations thereof refer to reducing, limiting progression, ameliorating, or resolving, to any extent, the symptoms or signs related to a condition. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the a condition manifests in a subject, while "prophylactic" treatment is initiated before a condition manifests in a subject.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Mmergln-int is a murine LTR retrotransposon that is expressed in multiple tissues. Initially, in studies described in more detail below, we discovered that Mmergln-int (a)

contains open reading frames for common retroviral genes gag, pol, and env, (b) p53 activates Mmergln-int expression, and (c) upregulated expression of Mmergln-int env decreases cell viability in the presence of p53.

Using the Conserved Domain Database, we observed that the envelope of Mmergln-int belongs of the Ebola HIV-1-like heptad repeat 1-heptad repeat 2 superfamily (HR1-HR2 superfamily), a domain superfamily characterized by its HR1-HR2 domain. The HR1-HR2 domain is present in numerous exogenous and endogenous retroviruses. Thus, our observations using the murine Mmergln-int may be extrapolated to endogenous retrovirus envelope proteins in the HR1-HR2 superfamily. We collated the GI numbers from each subfamily of the HR1-HR2 superfamily and found a total of 70 proteins that were classified as members of the HR1-HR2 superfamily, 42 of which are found in non-viral species (Table 1). Of the 42 HR1-HR2 Domain-containing proteins found in non-viral species, 15 are found in *Homo sapiens*. (Table 2). Interestingly, while the H1-H2 superfamily Env proteins in humans are highly conserved, the corresponding Gag and Pol proteins are highly mutated and no longer have open reading frames. This suggests selective pressure to preserve the Env protein because it is the functional component of the endogenous retrovirus.

TABLE 1

| Reference No. | Organism | Reference No. | Organism |
|---|---|---|---|
| GI: 281351230 (Seq ID No. 85) | *Ailuropoda melanoleuca* (giant panda) | GI: 44887882 | *Homo sapiens* |
| GI: 83722646 | *Atlantic salmon swim bladder sarcoma virus* ‡ | GI: 44887889 | *Homo sapiens* |
| GI: 120561155 | *Avian leukosis virus* ‡ | GI: 47716681 | *Homo sapiens* |
| GI: 123217679 (Seq ID No. 121) | *Bos taurus* (cattle) | GI: 119476 | HoMuLV *murine leukemia virus* ‡ |
| GI: 119400 | *Bovine immunodeficiency virus* R29 ‡ | GI: 119464 | *Human T-cell lymphotrophic virus* type 1 ‡ |
| GI: 296215288 (Seq ID No. 86) | *Callithrix jacchus* (white-tufted-ear marmoset) | GI: 4930066 | *Human T-lymphotropic virus 1* ‡ |
| GI: 296220571 (Seq ID No. 96) | *Callithrix jacchus* (white-tufted-ear marmoset) | GI: 119467 | *Human T-lymphotropic virus 2* ‡ |
| GI: 148726013 (Seq ID No. 109) | *Danio rerio* (zebrafish) | GI: 82300752 | *Jaagsiekte sheep retrovirus* ‡ |
| GI: 193885318 | Ebola virus ‡ | GI: 82294412 | *Jembrana disease virus* ‡ |
| GI: 5107713 | Ebola virus ‡ | GI: 465412 | Marburg virus ‡ |
| GI: 82278767 | *Equine infectious anemia virus* ‡ | GI: 119482 | Mason-Pfizer monkey virus ‡ |
| GI: 82302297 | *Equine infectious anemia virus* ‡ | GI: 126294061 (Seq ID No. 102) | *Monodelphis domestica* (gray short-tailed opossum) |
| GI: 399433 | *Feline endogenous virus* ECE1 ‡ | GI: 126331679 (Seq ID No. 97) | *Monodelphis domestica* (gray short-tailed opossum) |
| GI: 82317606 | *Feline immunodeficiency virus* ‡ | GI: 126340267 (Seq ID No. 105) | *Monodelphis domestica* (gray short-tailed opossum) |
| GI: 82281565 | *Feline immunodeficiency virus* ‡ | GI: 111145928 | *Mouse mammary tumor virus* (MMTV) ‡ |
| GI: 119417 | *Feline leukemia* provirus ‡ | GI: 27735176 | *Mus musculus* (house mouse) |
| GI: 30313561 (Seq ID No. 112) | *Gallus gallus* (chicken) | GI: 33667796 | *Mus musculus* (house mouse) |
| GI: 45383091 (Seq ID No. 118) | *Gallus gallus* (chicken) | GI: 74180532 | *Mus musculus* (house mouse) |
| GI: 47605605 (Seq ID No. 92) | *Gorilla gorilla gorilla* (western lowland gorilla) | GI: 12854150 | *Mus musculus* (house mouse) |
| GI: 47605612 (Seq ID No. 83) | *Gorilla gorilla gorilla* (western lowland gorilla) | GI: 148703999 | *Mus musculus* (house mouse) |
| GI: 119432 | HIV-1 ‡ | GI: 26332246 | *Mus musculus* (house mouse) |
| GI: 119439 | HIV-1 ‡ | GI: 149412708 | *Ornithorhynchus anatinus* (platypus) |
| GI: 119595081 | *Homo sapiens* | GI: 157779048 (Seq ID No. 123) | *Ovis aries* (sheep) |
| GI: 121944325 | *Homo sapiens* | GI: 114645334 (Seq ID No. 88) | *Pan troglodytes* (chimpanzee) |
| GI: 145651814 | *Homo sapiens* | GI: 24474949 (Seq ID No. 99) | *Pan troglodytes* verus |
| GI: 44887864 | *Homo sapiens* | GI: 223627 | *Rous sarcoma virus* ‡ |
| GI: 44887888 | *Homo sapiens* | 999443 | *Simian immunodeficiency virus* (SW) ‡ |
| GI: 47605576 | *Homo sapiens* | 2EZS A | *Simian immunodeficiency virus* (SW) ‡ |
| GI: 47605616 | *Homo sapiens* | GI: 119494 | *Simian immunodeficiency virus* (SW) ‡ |
| GI: 47716681 | *Homo sapiens* | GI: 3891827 | *Simian immunodeficiency virus* (SW) ‡ |
| GI: 80550508 | *Homo sapiens* | GI: 224132894 (Seq ID No. 103) | *Taeniopygia guttata* (zebra finch) |
| GI: 195963433 | *Homo sapiens* | GI: 224147561 (Seq ID No. 117) | *Taeniopygia guttata* (zebra finch) |
| GI: 300796687 | *Homo sapiens* | GI: 224167236 (Seq ID No. 113) | *Taeniopygia guttata* (zebra finch) |
| GI: 300796709 | *Homo sapiens* | GI: 11055586 (Seq ID No. 94) | *Trichosurus vulpecula* (common brushtail) |

TABLE 1-continued

| Reference No. | Organism | Reference No. | Organism |
|---|---|---|---|
| GI: 44887863 | *Homo sapiens* | GI: 325053859 | Unknown |
| | | GI: 301605491 | *Xenopus* (*Silurana*) *tropicalis* |
| | | (Seq ID No. 114) | (western clawed frog) |

‡ virus species

TABLE 2

| Envelope | Chromosomal Location | GI No. |
|---|---|---|
| envR | 7q21.2 | GI: 145651814 |
| envW | 7q21.2 | GI: 195963433 |
| envV 1 | 19q13.41 | GI: 300796687 |
| envV 2 | 19q13.41 | GI: 300796709 |
| envF(c)1 | Xq21.33 | GI: 44887863 |
| envF(c)2 | 7q36.2 | GI: 7770445 |
| envFRD | 6p24.1 | GI: 44887864 |
| envR(b) | 3p24.3 | GI: 44887882 |
| envH2 | 3q26 | GI: 44887888 |
| envH1 | 2q24.3 | GI: 44887889 |
| envH3 | 2q24.1 | GI: 8439399 |
| envK | 1q23.3 | GI: 47605576 |
| envK1 | 12q14.1 | GI: 47605616 |
| envT | 19q13.11 | GI: 47716681 |
| ABB52637 | unknown | GI: 80550508 |
| hCG2039039 | unknown | GI: 119595081 |
| Q4KWC9 | unknown | GI: 121944325 |

Figure 2:
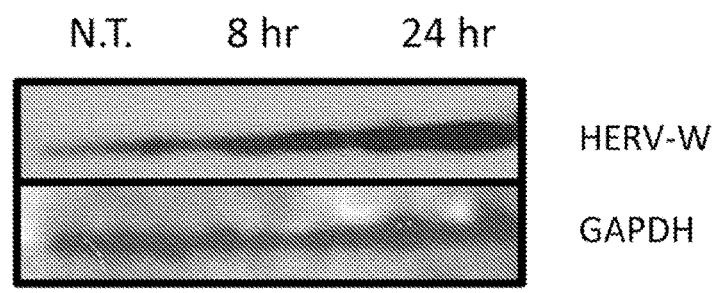
FIG. 2. HERV-W is upregulated in response to genotoxic stress.

Next, we stressed human cells to determine whether one can detect upregulation of these retroviral Env proteins. We designed a qPCR-based screen and determined that endogenous retroviral Env proteins are indeed upregulated at the transcript level in human cells. We designed qPCR primers to specifically recognize the intact open reading frames of the endogenous retroviral Env proteins. We detected upregulation of endogenous retrovirus Env proteins in cells from various human tissues. For example, the endogenous retrovirus Env proteins HERV-FRD, HERV-K, HERV-R, HERV-V, HERV-ENV2, and HERV-W were upregulated in a human breast cell line eight hours after UV exposure. As another example, the endogenous retrovirus Env proteins HERV-F (c)1 and HERV-FRD were upregulated in a human prostate cell line after similar UV exposure. Moreover, HERV-W was upregulated at the protein level, with an increase in protein level eight and 24 hours after UV exposure in comparison to non-treated Mcf7 cells (FIG. 2).

To find further evidence for regulation of HERV-W by p53, we looked for p53 response elements in the LTR of HERV-W. We identified nine decameric motifs with high similarity to the p53 consensus sequence. (FIG. 3, light shading reflects consensus sequence nucleotides, dark shading reflects point mutations). We did not find two motifs with a spacer of less than 13 nucleotides. However, substantial transactivation of p53 by noncanonical p53 consensus sequences that contain a single decameric motif, or "half-site" have been identified (Jordan et al., 2008. *PLoS Genet* 4(6):e1000104).

Thus, p53 activates the expression of endogenous retroviral Env proteins in humans. The ability of ancient retroviruses to sense cellular stress of their host may have been advantageous to the retrovirus in determining its state in the lytic and lysogenic cycle. The exaptation of retroviral Env proteins of the Ebola RSV-like HR1-HR2 domain superfamily may be beneficial to non-viral organisms also. Although many human endogenous retrovirus loci are degenerate due to the accumulation of mutations that result in truncated open reading frames that can render the gag and the pol proteins nonfunctional, the open reading frames of endogenous retrovirus envelope coding regions have remained intact. This suggests a positive selection for the endogenous retrovirus envelope proteins, which are likely to be functional. We demonstrate that expression of endogenous retroviral Env open reading frames is upregulated in the modern human genome following cellular stress. Also, because their expression is regulated by p53, the expressed Env proteins can serve as a cell surface marker for cells that overexpress p53, one hallmark of neoplasticity.

Moreover, the expression of endogenous retroviral Env protein in the modern human genome is consistent with the expression of corresponding retroviral Env protein we observed in the mouse genome. Endogenous retrovirus Env expression and p53 response elements that regulate expression of endogenous retrovirus Env proteins are similar in mouse and humans. As described in more detail below, murine endogenous retrovirus Env expression decreases cell viability. The similarities that we have observed in endogenous retrovirus Env expression in mouse cells and human cells lead us to conclude that expression of human endogenous retrovirus Env proteins decreases cell viability in a manner similar to that observed in mouse cells. Accordingly, overexpression of human endogenous retrovirus Env proteins can provide targeted cell-based therapy against neoplastic cells originating from various human tissues such as, for example, breast tissue and prostate tissue. In addition, p53 mutations are reported in cancer of the ovary, colorectum, esophagus, head and neck, larynx, lung, skin, pancreas, stomach, liver, brain, bladder, breast, uterus, soft tissues, lymph nodes, prostate, bones endocrine glands, the hematopoietic system, and cervix. Furthermore, p53 transactivation of target genes—e.g., endogenous retrovirus Env—is involved tumor suppression in these tissues. Finally, aberrant expression of endogenous retroviruses is evident in lymphoma, breast cancer, melanoma and cells of the immune system in human cancers. Therefore, overexpression of endogenous retrovirus Env proteins can provide targeted cell-based therapy against neoplastic cells originating from these other tissues.

To investigate whether p53 regulates the expression of non-genic regions of the murine genome, we performed RNA Sequencing on primary p53+/+, p53+/−, and p53−/− mouse embryonic fibroblasts (MEFs). RNA Seq identified transcription of both established p53 targets and novel p53 targets. Among the top genomic loci differentially expressed among p53+/+, p53+/−, and p53−/− MEFs, we identified transcription of genomic loci for which no references genes are annotated. Within these genomic coordinates, we identified LTR Retrotransposons, LINES, SINES, Micro Satellites, Low Complexity Repeats and DNA Repeat Elements. (Table 3).

TABLE 3

RNA Sequencing Data Analysis

| Genome coordinates | Repetitive Elements |
| --- | --- |
| chr2: 75476500-75486500 | MMVL30-int and other LTR Retrotransposons, SINES and Micro Satellites |
| clu-4: 149442800-149452800 | LTR Retrotransposons, SINES, LINES, Micro Satellites and Low Complexity Repeats |
| chr8: 124357500-124367500 | Mmergln-int and other LTR Retrotransposon, SINES, Micro Satellites, DNA Repeat elements |

Using the Integrated Genome Viewer, we extracted the sequences of the regions which demonstrated loss of expression in p53−/− MEFs. We identified expression of the LTR Retrotransposons MMV30-int and Mmergln-int and SINEs of the Alu, B2 and B4 families in p53+/+ and p53−/+MEFs, and loss of expression in p53−/− MEFs.

Mutations in the genome frequently render endogenous retroviruses inactive. Therefore, we determined whether we could identify the open reading frames (ORFs) in the LTR retrotransposons MMV30-int and Mmergln-int. Using NCBI's Open Reading Frame Finder, we did not find open reading frames within the sequence of MMV30-int. We identified that the transcript of Mmergln-int, derived from chromosome 8: 124357175-124364734 (mm9), contains open reading frames with homology to retroviral gag, pro, pol, and env coding regions. In the +1 frame from basepairs 526-2139, we detected homology to the matrix protein, p15, and Gag p30, which are involved in viral assembly and pathogenicity. In the +1 frame at nucleotide position 2395-5682, we detected sequence homology to the RT ZFREV-like family of reverse transcriptases, Bel/Pao family of RNase HI, and a Rve Integrase which mediates the integration the provirus into the host genome. Finally, we detected the env coding region at nucleotide position 6514-7518, which belongs to Ebola RSV-like heptad repeat 1-heptad repeat 2 (HR1-HR2) domain superfamily. (FIG. 4). Mmergln-int can encode functional retroviral particles and is highly abundant in the mouse genome. We detect 86 genomic loci with homology to Mmergln-int throughout the murine genome, distributed across every murine chromosome with the exception of chromosome 20.

Figure 5:
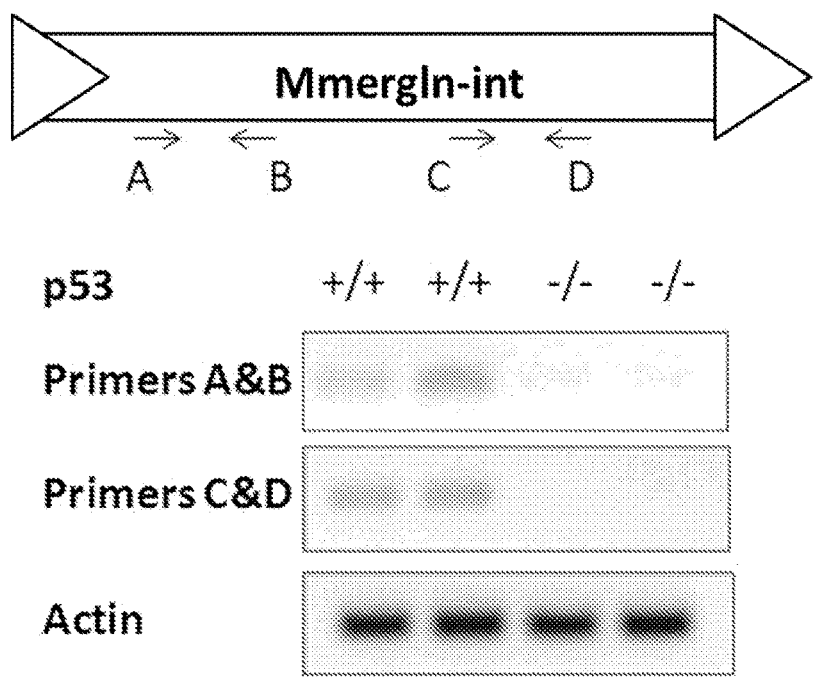
FIG. 5. Semi-quantitative RT PCR detects the expression of Mmergln-int in p53+/+ MEFs but not in p53−/− MEFs. Two pairs of primers were made to span the transcript of Mmergln-int at the 5' and regions of the transcript.
Figure 6:
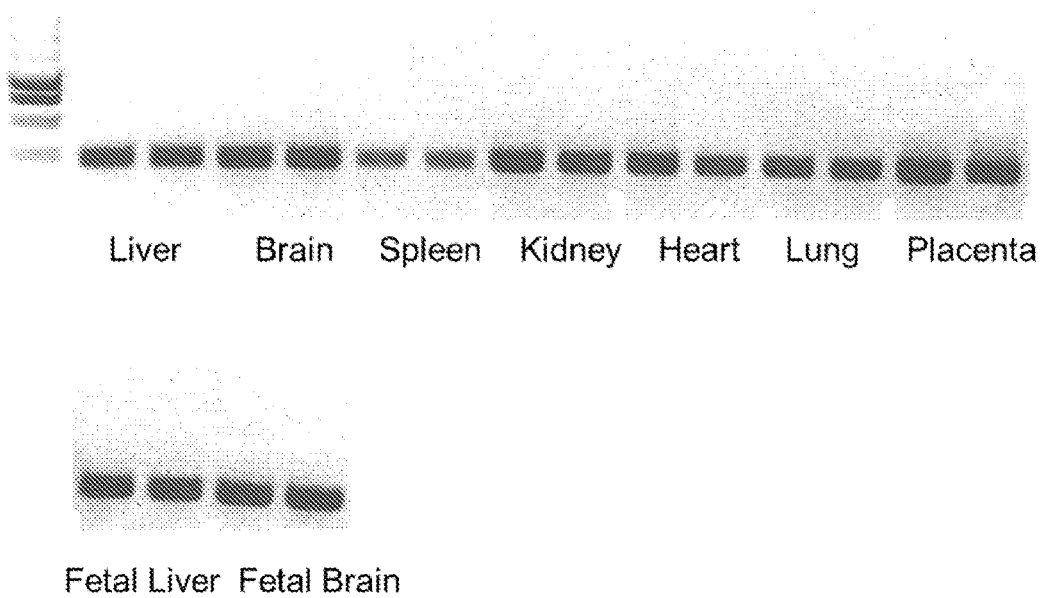
FIG. 6. Semi-quantitative RT PCR detects the expression of Mmergln-int in multiple adult and fetal tissues. RNA was extracted from the tissues two mice (n=2) for conversion to cDNA.

To verify that expression of Mmergln-int is p53-dependent, we performed semiquantitative reverse transcriptase PCR (RT-PCR) using cDNA generated from p53+/+ and p53−/− MEFs. Consistent with our RNA Seq data, we detected the expression of MMergln-int in p53+/+MEFs, but not in p53−/− MEFs (FIG. 5). The expression of endogenous retroviruses often may be restricted to few tissues such as the placenta. Therefore, investigated the distribution of Mmergln-int expression among multiple tissue types. We detected the transcript of Mmergln-int in all tissues examined with the highest expression being found in the placenta and lowest in the spleen. (FIG. 6).

After observing that Mmergln-int expression is lost in the absence of p53, we looked for evidence of p53 regulatory elements within the promoter region of Mmergln-int. The p53 tetramer binds a highly conserved p53 responsive element (RE). The p53 RE is defined as two decameric motifs, with a sequence of RRRCWWGYYY (SEQ ID NO:1) where R=purine, Y=pyrimidine, W=A or T. The two decameric motifs are separated by a spacer of 0 to 13 nucleotides. Since the Long Terminal Repeats (LTRs) of retroviruses serve as promoters, we searched for the presence a p53 response element within the LTR of Mmergln-int. Within the 430 by of the Mmergln-int LTR, RLTR1B, we found the sequence GGACATGCCCGGGCAAGCCC (SEQ ID NO:4) at position 103-123, which fits the sequence criteria of a p53 RE, with a spacer of 0 nt.

To test the ability of p53 to regulate the expression of Mmergln-int, we cloned the LTR into a promoterless luciferase vector and tested its ability to drive the expression of luciferase in p53+/+ and p53−/− MEFs. We detected robust expression of luciferase in p53+/+MEFs greater than or equal to our p21 promoter positive control vector. We detected negligible luciferase expression driven by p21 or the LTR in p53−/− MEFs. To determine if the Mmergln-int p53 response element is the single site of p53 regulation within the LTR, we performed site-directed mutagenesis to render the promoter non-functional. The cytosine at nt positions 4 of the decameric motif is highly conserved because it mediates DNA-protein interaction. Therefore, we generated cytosine to adenine transversion mutations at position 107, 177, or both 107 and 117. The transversion mutations and mutant p21 promoter failed to promote luciferase expression in p53+/+ and p53−/− MEFs.

Figure 7:
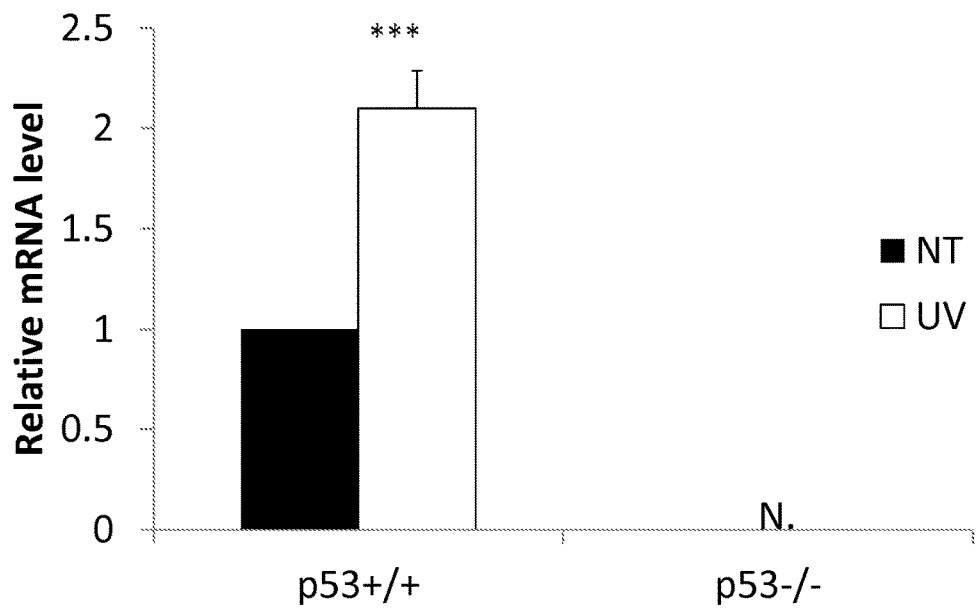
FIG. 7. Genotoxic stress upregulates the transcription of Mmergln-int. Detection of the upregulation of Mmergln-int transcript 8 hours after treatment with 50 kj/m$^2$.

The stability of p53 can be increased in response to various forms of cellular stress. To determine if enhanced p53 stability upregulates Mmergln-int expression, we treated the MEFs with UV irradiation or Doxorubicin. We observe a significant increase in luciferase expression driven by the LTR after exposure to genotoxic agents in p53+/+ MEFs. Furthermore, we detect a 2.1±0.19 fold increase of the Mmergln-int transcript post UV irradiation. (FIG. 7). To detect a physical interaction of p53 with the LTR of Mmergln-int, we performed chromatin immunoprecipitation in p53+/+ and p53−/− MEFs. The p53 antibody precipitated the LTR as well as other established p53 target genes in p53+/+ MEFs.

Next, we analyzed the functional consequences of Mmergln-int expression. With the similarities observed between Mmergln-int expression and human endogenous retrovirus Env proteins expression, Mmergln-int serves as a model for human endogenous retrovirus Env expression. Thus, one can extrapolate the functional consequences of Mmergln-int expression to be similar to the functional consequences of human endogenous retrovirus Env expression.

Figure 8:
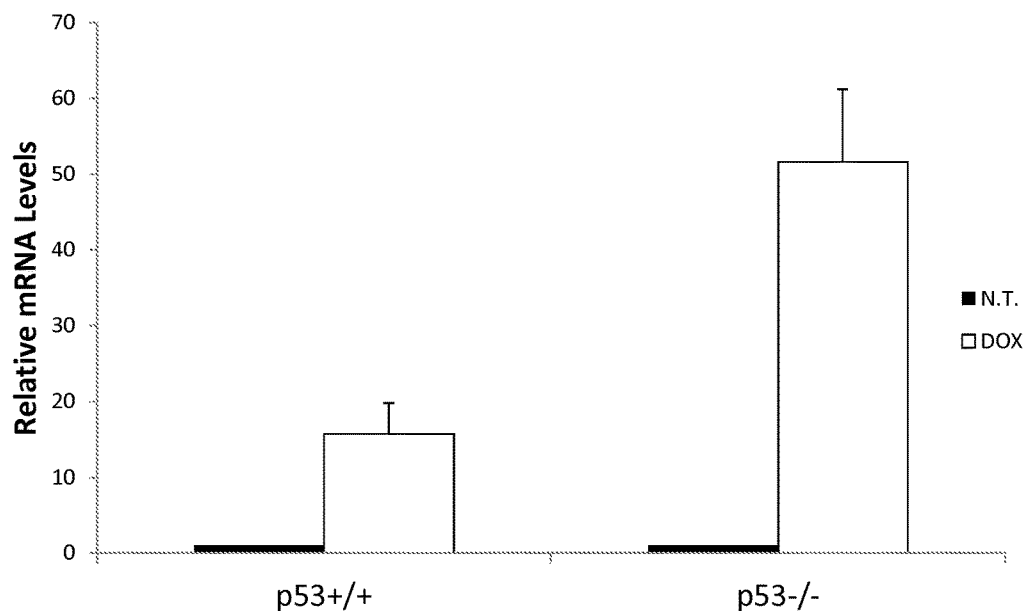
FIG. 8. Dox induces p53-independent expression of Mmergln-int.

We developed a doxycycline-inducible system to overexpress Mmergln-int in p53+/+ and p53−/− MEFs. Upon induction with doxycycline, we detected the expression of GFP by florescence microscopy and observed a 15-fold (±4.1) and 51-fold (±9.6) increase of the Mmergln-int transcript in p53+/+ and p53−/− MEFs, respectively (FIG. 8). Thus, expression of Mmergln-int may be induced in both p53+/+ and p53−/− MEFs.

Figure 9:
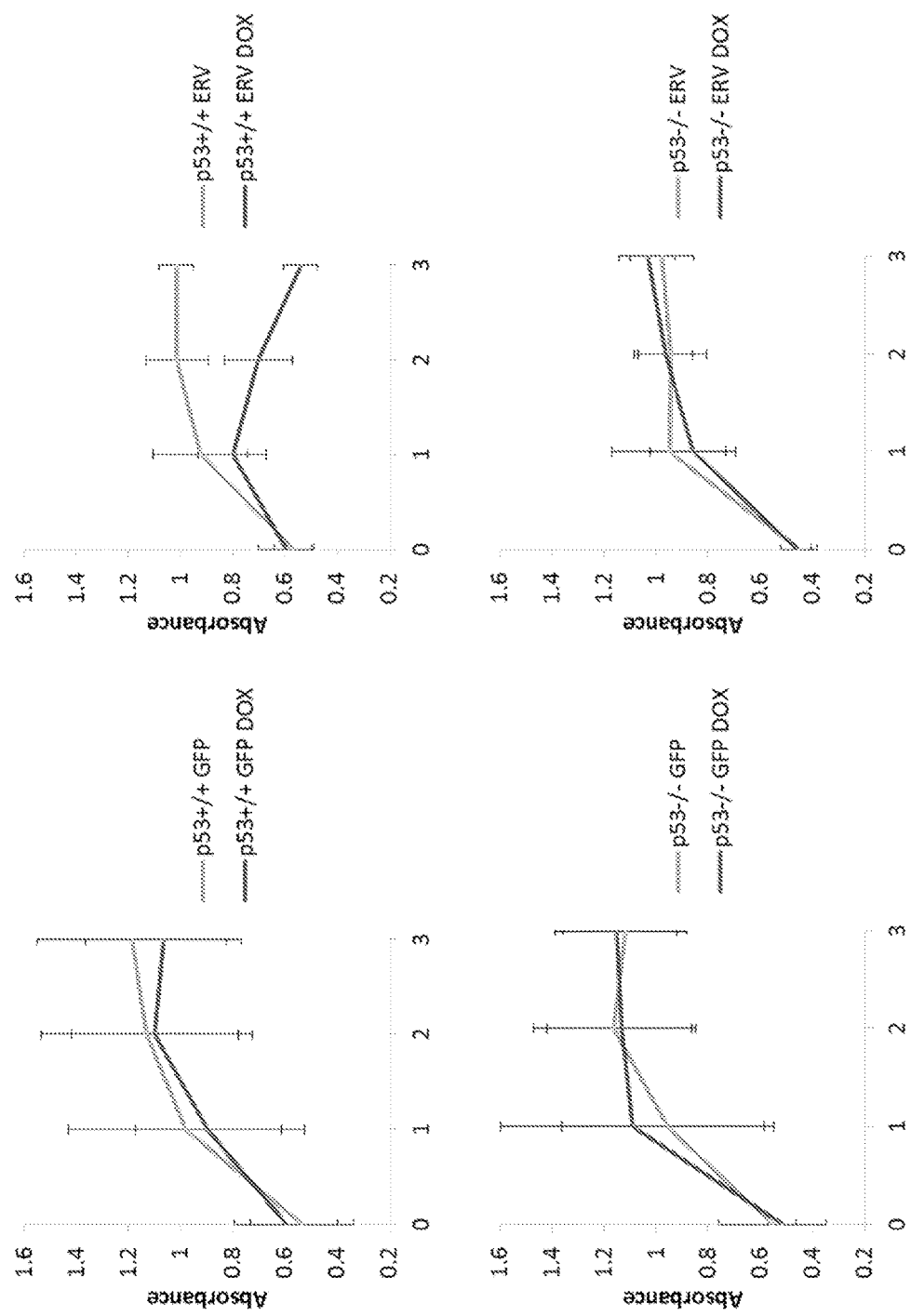
FIG. 9. Overexpression of endogenous retrovirus results in decreased cell viability in p53+/−+MEFs. OD readings were plotted for absorbance measurements taken at 12, 36, 60 and 80 hours. Error bars represent S.D.
Figure 10:
FIG. 10. Overexpression of Mmergln-int env is sufficient to decrease proliferation of p53+/+MEFs FIG. 11. Identification of hERVs transcriptionally upregulated after UV exposure in LNCaP cells.
Figure 11:
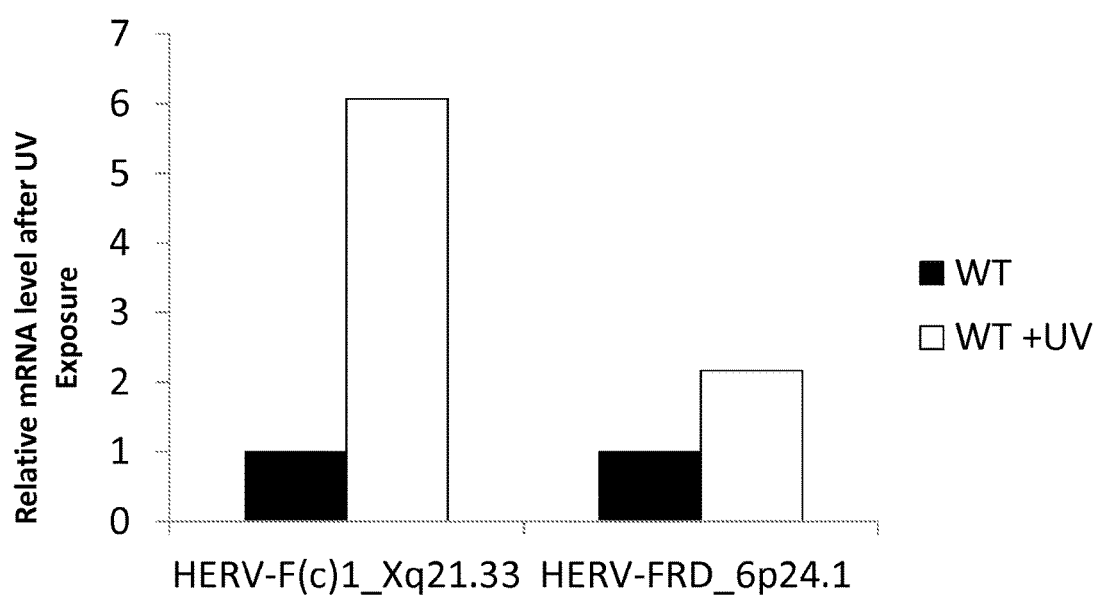

To determine cell viability, we performed a MTT assay. We detected no significant change in cell viability upon induction of GFP in either p53+/+ or p53−/− MEFs (FIGS. 9a and 9b) or induction of Mmergln-int (ERV) in p53−/− MEFs (FIG. 9d). We saw a decrease in cell viability, however, in p53+/+MEFs at 36 hours (1.5 days), 60 hours (2.5 days), and 84 hours (3.5 days) after exposure to doxycycline (FIG. 9c). No decrease in cell viability was observed in p53−/− MEFs overexpressing Mmergln-int. Thus, p53 is involved in cell death mediated by Mmergln-int, indicating that the Mmergln-int functions in a feed forward signaling mechanism that enhances p53 activity that decreases in cellular viability. Moreover, expression of Mmergln-int Env is sufficient to mediate cell death. We individually expressed the gag, pol, or env of Mmergln-int under a CMV promoter. We observe a decrease in cell viability at 3.5 days post transfection with the Mmergln-int env, but not after transfection with either gag or pol. (FIG. 10).

When inspecting the morphology of the MEFs by bright field microscopy, we observed what appeared to be syncytia. We performed immunofluorescence using an anti-β-catenin antibody to detect the cellular membrane and DAPI to stain the nuclei. Some viral envelopes of the Ebola RSV-like HR1-HR2 domain superfamily mediate cellular fusion through their HR1-HR2 domain. Cellular fusion mediated by viral envelopes can mediate cell death via apoptotic and non-apoptotic pathways.

The observation that p53−/− MEFs do not demonstrate significant changes in cell viability suggests p53 is involved in cell death pathways induced by overexpression of Mmergln-int Env. Interestingly, the HIV retroviral envelope, which is also a classified as a member of the Ebola RSV-like HR1-HR2 domain superfamily activates the p53 signaling pathway. Expression of the HIV envelope protein induces cellular fusion and subsequent mitotic catastrophe through the activation of Chk2, a upstream component of the p53 signaling pathway. Therefore, it is possible that the observed cellular fusion phenotype reflects the mechanism of cell death responsible for the decrease in cell viability. It is further possible that additional or alternative pathways amplify the p53 signaling pathway. For example, expression of the hERV-W Env protein can activate the endoplasmic reticulum (ER) stress responses and ER stress can induce apoptosis through p53 signaling.

Figure 13:
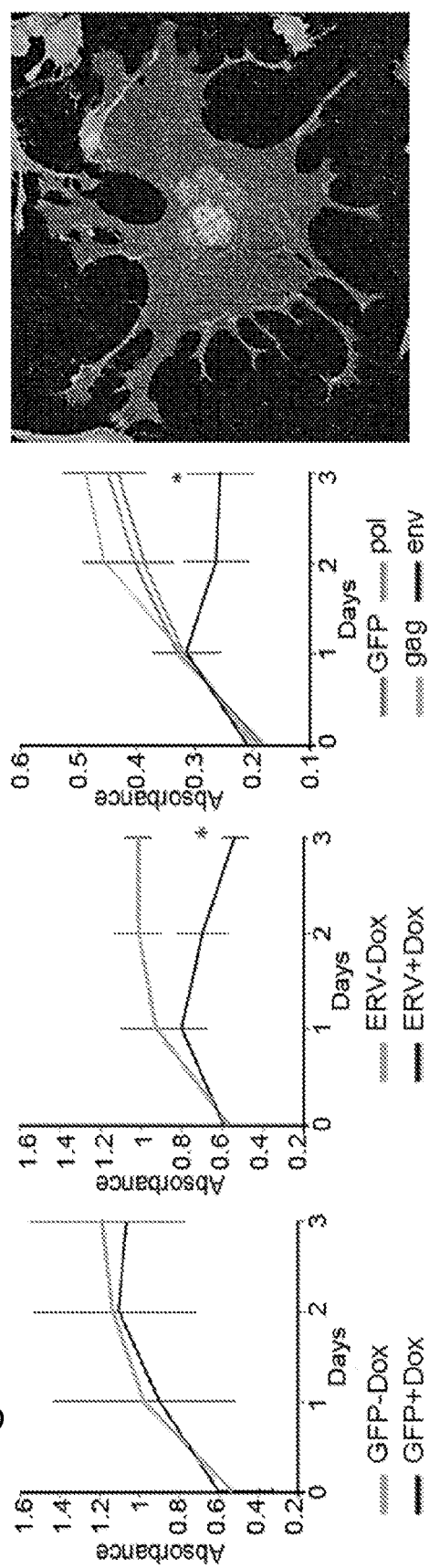
FIG. 13. Mmergln-int envelope can mediate cellular senescence. Transient overexpression of Mmergln-int results in decreased cell viability in wild type MEFs, which can be detected by a MTS assay.

Mmergln-int envelope can induce cellular senescence in wild type mouse embryonic fibroblasts. Overexpression of entire Mmergln-int, or its envelop (but not gag or pol) leads to decreases in cell viability in p53+/+ mouse embryonic fibroblasts (MEFs), and the transient overexpression of the env is sufficient to induce cellular senescence in p53+/+ MEFs (FIG. 13).

Figure 14:
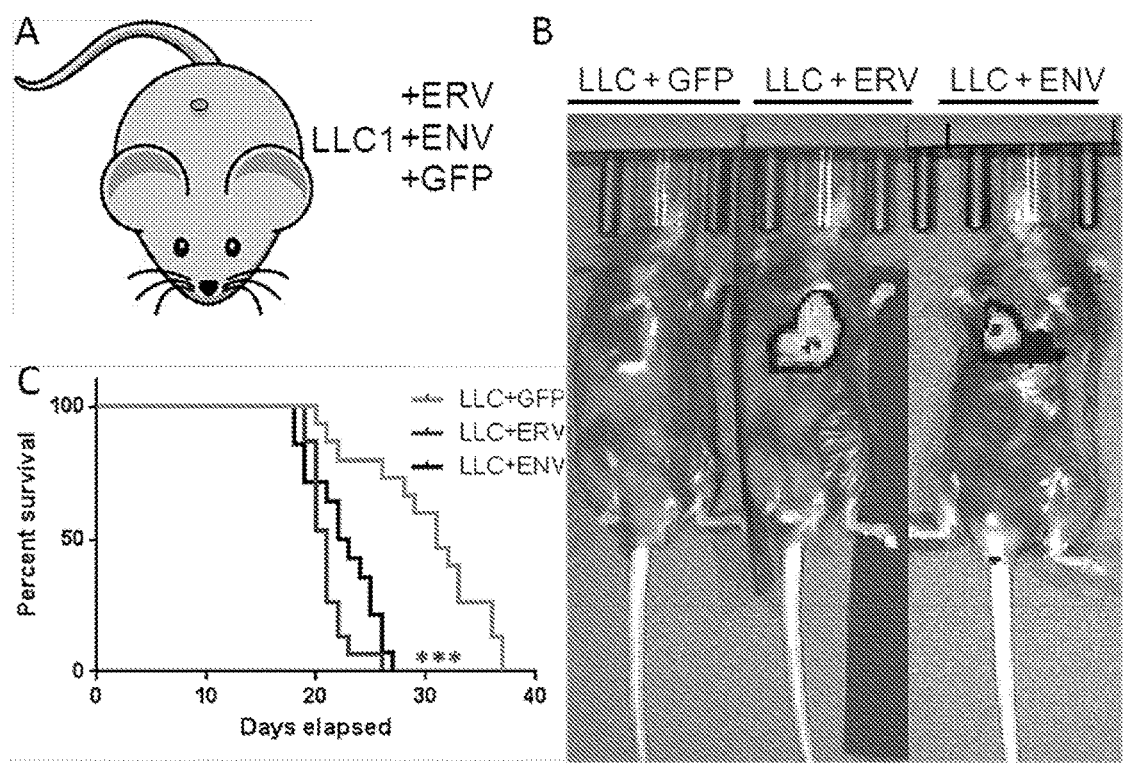
FIG. 14. Lung carcinomas expressing endogenous retroviral envelopes exhibit early tumor latency (A) C57/B6 mice were injected with isogenic Lewis lung carcinoma (LLC1) cells harboring GFP, Mmergln-int endogenous retrovirus or Mmergln-int ENV. (B) On day 14 tumors are not detected in GFP expressing LLC1 cells but LLC1 cells expressing endogenous retrovirus or ENV localize to lungs to form tumors. (C) Kaplan Meier analysis compares lifespan of LLC1-GFP (green), LLC1-ERV (red) and LLC1-ENV (black) mice.

Mmergln-int envelope can enhance tumorigenicity of transformed cells in vivo. We investigated the consequences of ectopic expression of Mmergln-int ENV in the context of already transformed cells. We expressed full length Mmergln-int ERV, Mmergln-int ENV or the GFP constructs in Lewis lung carcinoma (LLC1), a cell line isolated from a lung tumor of a C57BL mouse and which form lung cancer in mice. $2\times10^5$ cells of each genotype were inoculated into C57BL mice via tail vein injection. Tumor volume was monitored by measuring the luciferase level in live mice every seven days (FIG. 14). The moribund mice were euthanized, the tumor tissue harvested, and histopathology was performed. Expression of Mmergln-int ERV or Mmergln-int ENV significantly increased the tumor burden and reduced the tumor latency in vivo. The median survival for mice inoculated with LLC1 expressing Mmergln-int ERV or Mmergln-int ENV are 21 and 22.5 days, compared to mice inoculated with LLC1 expressing GFP having median survival of 31 days, p<0.001, FIG. 14C). Median survival is the time period at which 50% of the mice have died. This suggests that expression of Mmergln-int ENV can lead to enhanced tumorigenicity of transformed cells in vivo.

Figure 15:
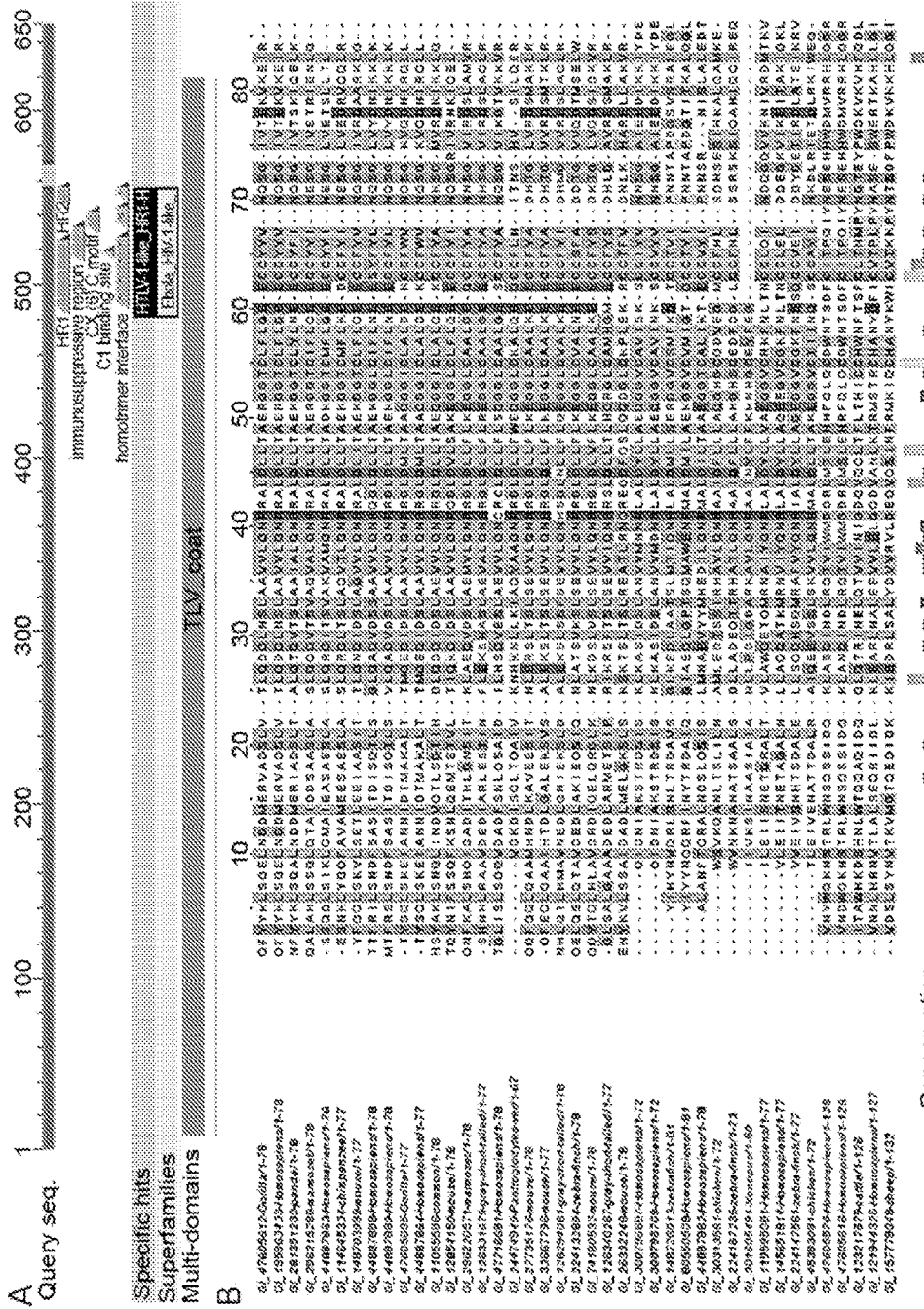
FIG. 15. HTLV-1-like envelopes are endogenized in the genomes of multiple vertebrate species. (A) A conserved domain database (CDD) analysis reveal that Mmergln-int ENV belongs to HTLV-1-like HR1-HR2 family of proteins. Sequences shown include HTLV-1-like HR1-HR2 domains from Gorilla gorilla gorilla (SEQ ID NOs:83 and 92); *Homo sapiens* (SEQ ID NOs:84, 87, 90, 91, 93, 98, 107, 108, 110, 111, 115, 116, 119, 120, and 122); *Ailuropoda melanoleuca* (SEQ ID NO:85); *Callithrix jacchus* (SEQ ID NOs:86 and 96); *Pan troglodytes* (SEQ ID NOs:88 and 99); *Mus musculus* (SEQ ID NOs:89, 95, 100, 101, 104, and 106); *Trichosurus Vulpecula* (SEQ ID NO:94); *Monodelphis domestica* (SEQ ID NOs:97, 102, and 105); *Taeniopygia guttata* (SEQ ID NOs:104, 113, and 117); *Danio rerio* (SEQ ID NO:109); *Gallus gallus* (SEQ ID NOs:112 and 188); *Xenopus tropicalis* (SEQ ID NO:114); *Bos Taurus* (SEQ ID NO:121); *Ovis aries* (SEQ ID NO:123). A consensus sequence is also shown (SEQ ID NO:124). (B) The HTLV-1-like HR1-HR2 domain was identified in human, gorilla, chimpanzee, bushtail, mouse, panda, marmoset, opossum, and zebra finch. Amino acids are highlighted to depict conservation among organisms. The degree of conservation is illustrated by calculating the conservation, quality, and consensus of the alignments.

Mmergln-int envelope belongs to a conserved HTLV-1-like HR1 HR2 protein domain family shared by many vertebrates (FIG. 15). A further examination of Mmergln-int ENV protein reveals that it is classified as member of the HTLV-1-like heptad repeat 1-heptad repeat 2 (HR1-HR2) protein domain family, a group of proteins that share a motif found in the oncogenic retrovirus human T-cell leukemia virus type 1 (HTLV-1, FIG. 15A). This highly conserved domain is present in modern infectious viruses and also is found endogenized in the genomes of many vertebrate species including, for example, humans, gorilla, chimpanzee, bushtaii, mouse panda, marmoset, opossum, and zebra finch (FIG. 15B). In addition, oncogenic retroviral envelope proteins from viruses such as Jaagsiekte Sheep Retrovirus (JSRV), avian hemangioma retrovirus (AHV), and Friend spleen focus-forming virus (SFFV) have been identified. Unlike classic mechanisms of retroviral tumorigenesis (e.g., viral capture of host proto-oncogenes or capture of host gene regulation through insertional mutagenesis), some retroviral envelope proteins alone can serve as promote malignant transformation. Infection by exogenous JSRV can cause lung cancer in sheep, and cellular transformation can be mediated by the viral envelope alone. Human lung tumors examined for JSRV infection did not find evidence for the exogenous sheep virus. Endogenous sequences similar to JSRV were detected in human lung tumors, however. The human endogenous retrovirus sequences with a high degree of homology to JSRV may contribute to the development of lung cancer tumors.

We further analyzed human endogenous retroviral envelopes belonging to HTLV 1-like HR1-HR2 protein family. Up to 8% of the human genome are endogenous retroviral sequences. Most of the sequences of retroviral origin have lost their coding potential, thus relegating the status of these sequences as 'junk DNA'. However, an analysis of the complete human genome revealed that 16 envelope sequences of retroviral origin have retained their coding potential. All 16 sequences code for retroviral envelope genes, while the gag and pol genes of endogenous retroviruses have accumulated mutations that render them inactive. This suggests a positive selection for sequences that encode the endogenous retrovirus envelope proteins. An analysis of these 16 envelope sequences using conserved domain database (CDD) shows that all of them belong to the HTLV-1 HR1-HR2 family of proteins (FIG. 16), similar to Mmergln-int envelope protein.

Figure 17:
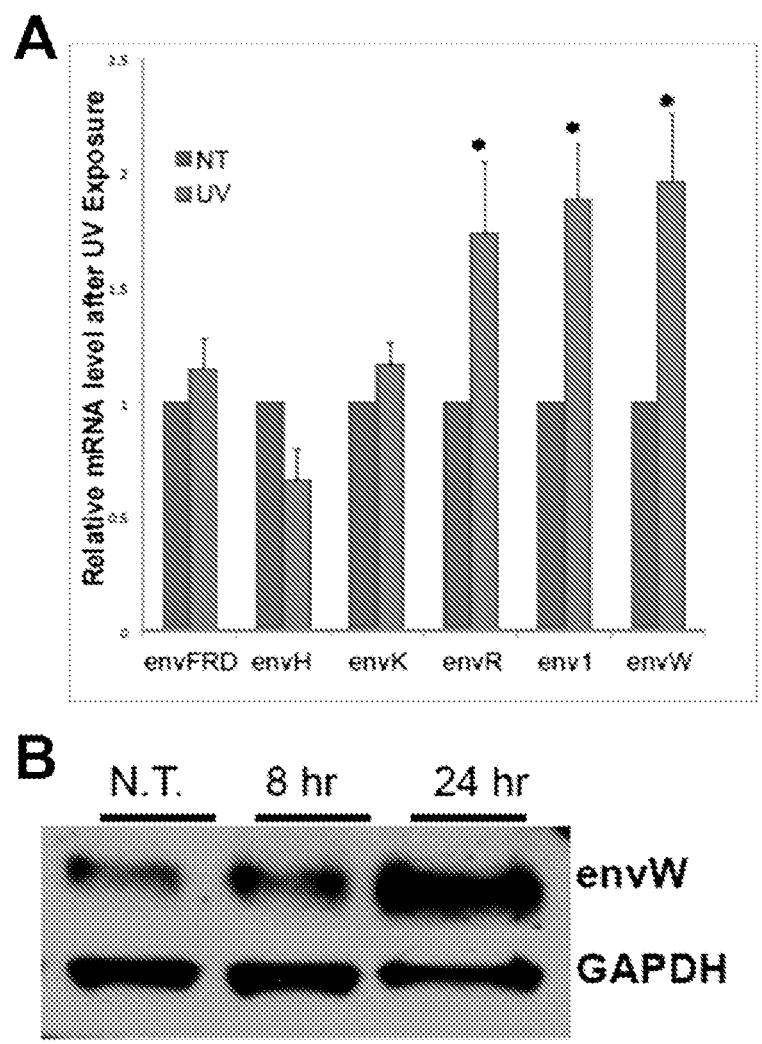
FIG. 17. HTLV-1-like envelopes are stress responsive in humans. (A) envR, envl, and envW are transcriptionally upregulated in response to UV stress in human Mcf7 cells. (B) envW is upregulated at the protein level at 12 hours and at 24 hours after UV exposure.

Human endogenous retrovirus envelope proteins are induced following DNA damage. We observe an approximately twofold upregulation of envR, envl, and envW transcripts in human p53+/+ breast carcinoma cells after UV exposure, a known agent to induce p53 (FIG. 17A). Although very few antibodies exist to detect expression of human endogenous retroviruses, we were able to confirm that protein level of envW increases at eight hours and 24 hours after UV exposure relative to non-treated cells (FIG. 17B). This suggests that these proteins are stress responsive and can be used as early markers following DNA damage.

We identified immunomodulatory domains in Mmergln-int and human endogenous retrovirus envelope proteins. To delineate the mechanism by which Mmergln-int ENV promotes tumorigenesis, we looked for putative protein domains within the ENV that may interact with established cancer signaling pathways. Using the conserved domain database we identified a distinct immunosuppressive domain residing within the ENV of the HR1-HR2 protein domain family. This well classified domain of 17 amino acid residues, referred to as a CKS-17 peptide, activates the Ras-Raf-MEK-MAPK and PI3K-AKT-mTOR signal transduction pathways. The CKS-17 peptide also can exert effects on cytokine regulation, which culminate in the inhibition of natural killer cells, macrophages, and cytotoxic T lymphocytes. Taken together, Mmergln-int ENV and homologous human endogenous retrovirus envelope proteins can enhance tumorigenesis by activating oncogenic signaling pathways and inhibiting an immune response associated with the clearance of neoplastic cells.

Figure 18:
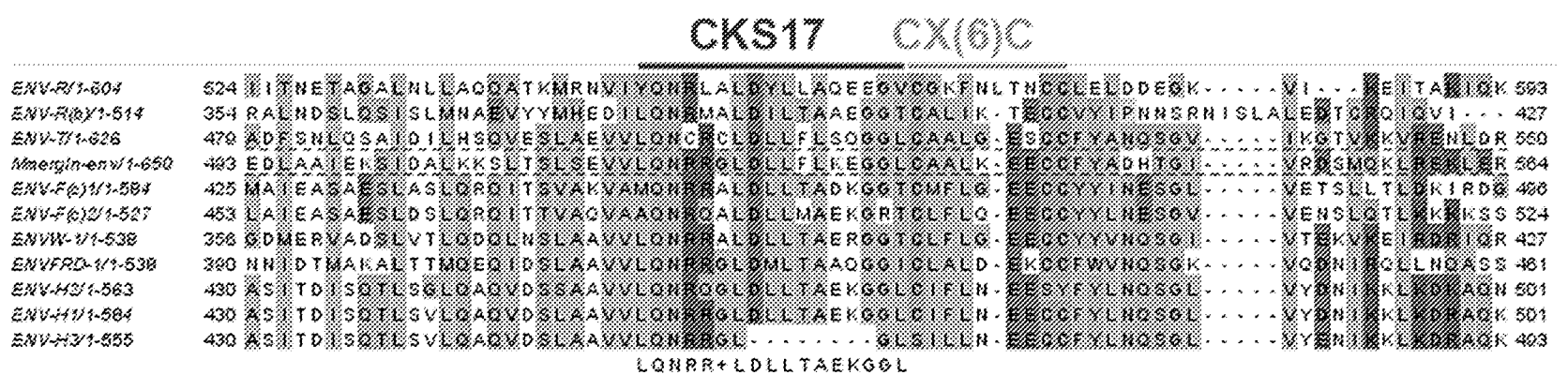

We also found that the human ENV proteins share a CX(6)C motif with Mmergln-int ENV, harboring conserved cysteine (C) residues separated by six amino acids (FIG. 18). The conserved cysteine residues may be involved in mediating cell fusion when these envelope proteins are expressed in response to oncogenic activation in non-cancerous cells, resulting to cellular senescence.

Understanding how cancer originates and progresses can lead to the development of better diagnostics and therapeutics. this disclosure addresses two issues regarding tumorigenesis, namely 1) the earliest molecular markers of cancer initiation, and 2) how these molecules activate oncogenic signaling pathways as well as interact with the immune system, thereby promoting expansion of neoplastic cells. Elevated expression of endogenous retrovirus proteins may allow identification of individuals at risk of developing cancer before the individuals begin to display any clinical sign or exhibit any symptoms of cancer. Therapeutically, the identification of markers of cancer initiation with immunosuppressive properties, such as human endogenous retrovirus (hERV) envelope proteins, can provide new therapeutic targets that allow for earlier medical interventions. Because the endogenous retrovirus envelope proteins have immunosuppressive activity, therapies that target these markers can be used as adjuvants that allow other immunotherapies to act without the immunosuppressive influence of the hERV envelope proteins.

Figure 19:
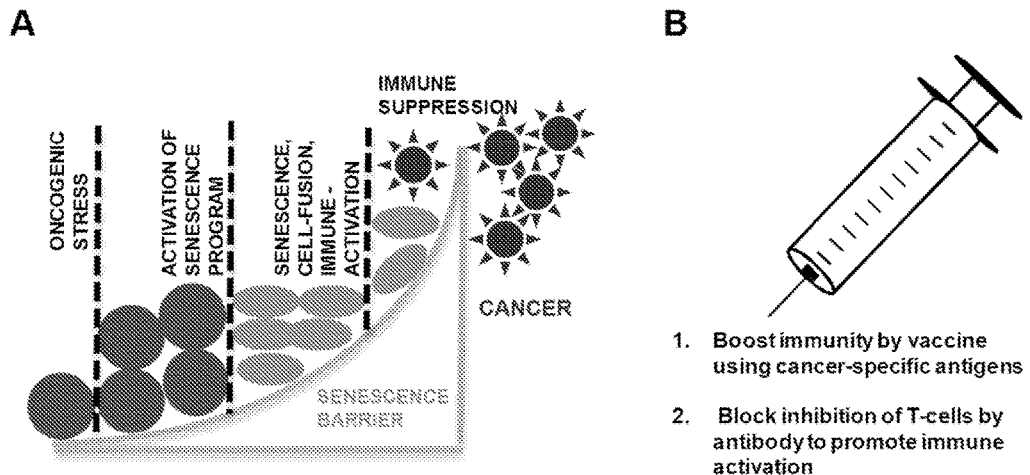
FIG. 19. Role of immune system in cancer and the scope of immunotherapy in treating cancer patients. (A) Different stages of tumorigenesis following an oncogenic stress. (B) Synergistic approach in boosting immunity through vaccine and inhibiting immune suppression as a therapeutic strategy for cancer patients.

The role of oncogene-induced senescence and how the immune system takes part in preventing cancer is illustrated in FIG. 19. Following an oncogenic assault (e.g., DNA damage, activation of an oncogene, etc.), the senescence program intrinsic in the cellular defense mechanism is activated. This results in cells that are affected with genotoxic stress undergoing replicative senescence, cell fusion, and ultimately being cleared by immune cells. Thus, the immune system plays an important role in the senescence barrier to cancer. Neoplasia develops, however, when some of these cells escape the immune surveillance mechanism by activating an immune suppressing mechanism. The cells that evade the immune surveillance system can lead to expansion of cancerous cells that ultimately leads to tumor formation and/or malignancy (FIG. 19A).

In one aspect, therefore, this disclosure describes a therapeutic composition that includes components that interact with human endogenous retrovirus envelope proteins. In some embodiments, the composition can include antibody that specifically binds to the CKS-17 domain of a human endogenous envelope protein. As sued herein, the term "antibody" in the absence of a preceding definite or indefinite article, is a general term that encompasses both polyclonal preparations and monoclonal antibodies. Such antibody can interfere with the cell signaling activity of the CKS-17 domain and/or reduce the immunosuppression (e.g., reduce inhibition of NK cells, macrophages, and CTLs) exerted by the endogenous retrovirus envelope protein through the CKS-17 domain. In some of these embodiments, the antibody can include a monoclonal antibody.

Figure 20:
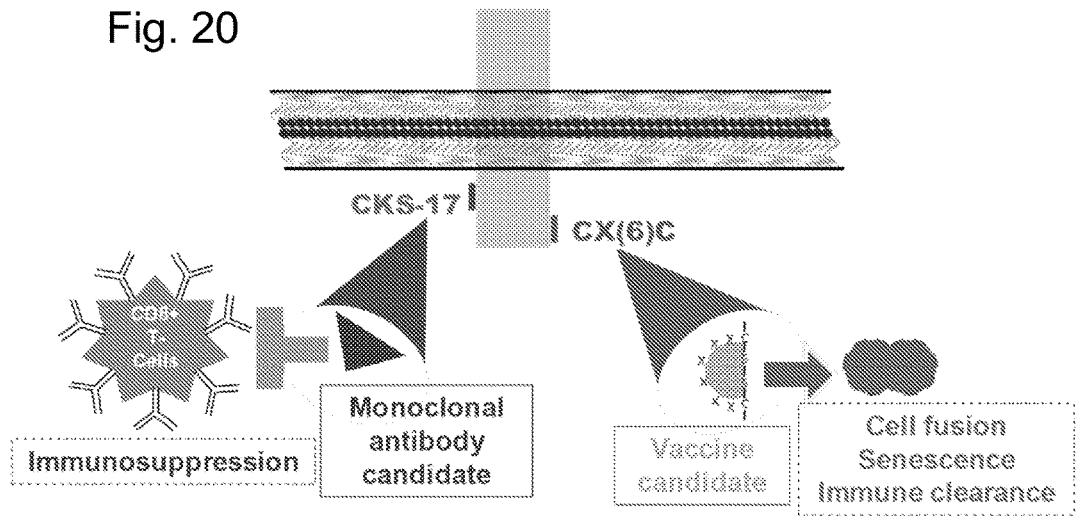
FIG. 20. CKS-17 and CX(6)C conserved in human and mouse envelopes as antibody and vaccine candidates for cancer immunotherapy.

In other cases, the composition can include a component that interacts with the CX(6)C domain of a human endogenous envelope protein to promote cell fusion, senescence, and/or immune clearance of pre-malignant or malignant neoplastic cells. CX(6)C may play a role in activation of innate immunity. For example, the CX(6)C motif can be recognized as a pathogen-associated molecular patterns (PAMPs) by, for example, toll-like receptors (TLRs) on antigen-presenting cells (APCs). The TLRs can then induce cytokines and chemokines and trigger other events that would result into induction and activation of matured T-cells and subsequently result into immune clearance of the pre-cancerous or malignant cells. Therefore, the CX(6)C motif can serve as a prophylactic vaccine candidate, similar to the ones used against cervical cancer caused by human papillomavirus. In some embodiments, the composition can include both a monoclonal antibody that specifically binds to the CKS-17 domain and a component that interacts with the CX(6)C domain. Such a composition can inhibit the mechanism by which cancer cells suppress immunity—i.e., reduce the inhibition of T cells that otherwise attack and/or clear cancer cells from the body (FIG. 20). Such a composition also can increase activity related to the identification and clearance of neoplastic cells from the body by promoting senescence and cell clearance.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Cell Culture

Mouse embryonic fibroblasts (MEFs) were derived from embryos 12.5 days post-conception (dpc) with a mixed B6/129 background (The Jackson Laboratory, Bar Harbor, Me.). The embryos were homogenized and plated on 10 cm tissue culture dishes. When cells reached confluency, they were passaged on three 10 cm dishes (p1), then frozen down into three vials per plate. The p1 vials of MEFs were thawed and the cells were expanded to passage 3 for experimental use. All experiments were conducted with early passage cells (p3-p6). MEFs were cultured in DMEM supplemented with 10% FBS and penicillin-streptomycin (100 units/ml). MCF p7 cells were cultured in DMEM supplemented with 10% FBS, penicillin-streptomycin (100 units/ml) and insulin (0.01 mg/ml). In induce cellular stress, cells were exposed to UV light (50 $J/m^2$) or doxorubicin (50 mg/ml).

MEFs were transiently transfected using the NEON transfection system (Invitrogen, Life Technologies Corp., Grand Island, N.Y.) or the FuGENE HD transfection reagent (Promega Corp., Madison, Wis.). Using the NEON transfection system, MEFs were pulsed once with a pulse voltage of 1,350 V and a pulse width of 30 ms at a density of $5 \times 10^6$/ml cells. To generate stable cell lines, MEFs were selected with puromycin. The expression of the tet-on constructs was induced using 50 ng/ml of doxycycline.

Generation of Constructs

Mmergln-int was PCR amplified from BAC RP23-8H9 using LA Taq DNA Polymerase (Takara Bio Inc., Shiga, Japan) and the following primers:

Mmergln-int F:
(SEQ ID NO: 5)
5'-GGTTCCAATGCGCATTTGGAGGTCCCAGCGAGAT-3'

Mmergln-int R:
(SEQ ID NO: 6)
5'-GGTTCCAAACTAGTTTCCCCTCTTCTTCTGTTTAGAC-3'.

Thermocycler conditions: 94° C. 1 min/94° C. 30 sec, 58° C. 1 min, 72° C. 9 min for 30 cycles/72° C. 10 min.

The gag, pol and env were PCR amplified from BAC RP23-8H9 using LA Taq DNA Polymerase (Takara Bio Inc., Shiga, Japan) and the following primers:

Pol F:
(SEQ ID NO: 7)
5'-GGTTCCAAAAGCTTATGCCTTTATTGGGGAGAGACTT-3'

Pol R:
(SEQ ID NO: 8)
5'-GGTTCCAAGCGGCCGCTCATTGAGTACCTCCCACGTTTG-3'

Env F:
(SEQ ID NO: 9)
5'-GGTTCCAAAAGCTTATGATGAGTGGACTTTGGAGAA-3'

Env R:
(SEQ ID NO: 10)
5'-GGTTCCAAGCGGCCGCTTAGAGGTCGGTGTCCCTTAAC-3'

Gag F:
(SEQ ID NO: 11)
5'-GGTTCCAAAAGCTTATGGGACAGACCGTGTCTACTC-3'

Gag R:
(SEQ ID NO: 12)
5'-GGTTCCAAGCGGCCGCTAGTCTTCATCTTCTCCAAGAG-3'

The following thermocycler conditions were used for to amplify the pol gene: 94° C. 1 min/94° C. 30 sec, 58° C. 1 min, 72° C. 3 min 30 sec for 30 cycles/72° C. 10 min. The gag and env genes were amplified with the following conditions: 94° C. 1 min/94° C. 30 sec, 58° C. 1 min, 72° C. 2 min for 30 cycles/72° C. 10 min. The PCR products were purified from an agarose gel using Wizard SV Gel and PCR Clean-Up System cloned into Invitrogen's pcDNA 3.1(+) expression vector.

Cell Viability

In order to determine cell viability, cells were seeded in a 96-well tissue culture dish at a concentration of $10^5$ cells/well. Cell viability was measured using a CELLTITER 96 AQueous One Solution Cell Proliferation Assay (MTS, Promega Corp., Madison, Wis.). Measurements were taken at 12 hours, 36 hours, 60 hours, and 84 hours after plating the cells. The MTS reagent was incubated at incubation at 37° C., and the absorbance was measured with a microplate reader (Synergy Mx, BioTek Instruments, Inc., Winooski, Vt.) at 490 nm and 650 nm.

Transcriptome Analysis

RNA was isolated from cells and tissues using an RNeasy Mini kit (Qiagen Inc. USA, Valencia, Calif.) according to the manufacturer's instructions, and treated with DNase I (Invitrogen, Life Technologies Corp., Grand Island, N.Y.) before cDNA synthesis.

To detect the transcript of Mmergln cDNA was synthesized using a reverse transcription system (GOSCRIPT, Promega Corp., Madison, Wis.). Multiple PCR primers were designed to span the transcript of Mmergln-int. The primer pairs used for RT PCR are provided in Table 4.

TABLE 4

| Primer | Chromosome location | SEQ ID NO |
|---|---|---|
| 5'-GGACCAAGGAGACCCAGAGAAG-3' | Ch8 ex2 Fi | 13 |
| 5'-CCCGTGTCAACTAGAAAGTC-3' | Ch8 ex2 Ri | 14 |
| 5'-TCCGAGCCAATAACCCACAGG-3' | Ch8 ex4 Fi | 15 |
| 5'-TTTAGCAGAGGCCCGATACC-3' | Ch8 ex4 Ri | 16 |
| 5'-CCACGCATCCCACGTTAAGAG-3' | Ch8 ex10 Fi | 17 |
| 5'-AGGCCACCAAGTCCACAGAG-3' | Ch8 ex10 Ri | 18 |
| 5'-CCAATTACTTTAACCCTGGCTGC-3' | Ch8 ex14 Fi | 19 |
| 5'-GTCGCTAGGTCTTCATTGACAG-3' | Ch8 ex14 Ri | 20 | cDNAs were amplified using a DNA Polymerase (GOTAQ, Promega Corp., Madison, Wis.). The following thermocycler conditions were used to amplify the transcript of Mmergln-int: 95° C. 2 min/95° C. 30 sec, 54° C. 15 sec, 72° C. 15 sec for 22 cycles/72° C. 5 min. β-actin loading control was run with the previous thermocycler conditions PCR products were run of 2% TBE agarose gels.

Real time quantitative PCR primers were designed to specifically detect to the envelope genes with a complete ORF. Primer sequences were designed using NCBI's Primer Blast or taken from de Parseval et al., 2003. J Virol 77(19): 10414-10422. RNA was extracted from cells with an RNeasy Mini kit (Qiagen Inc. USA, Valencia, Calif.) according to the manufacturer's instructions. cDNA was synthesized using a reverse transcription system (GOSCRIPT, Promega Corp., Madison, Wis.). Real time quantitative PCR was performed using 25 µl of a qPCR Master Mix (GOTAQ, Promega Corp., Madison, Wis.). The reactions were run using a realplex 2.2 thermocycler (Eppendorf, Hauppauge, HY) with the following program: 50° C. 2 min, 95° C. 10 min/95° C. 15 sec, 60° C. 1 min for 45 cycles. 95° C. 15 sec, 60° C. 15 sec, then 95° C. over 20 min for melting curve analysis.

β-actin or GAPDH was used as an internal control to calculate differences in the amount of total RNA added in each individual reaction. Experiments with variation of the internal control less than a factor of 1 were considered valid. A student's T test was performed to determine statistical significance. A p-value of p=0.05 was considered significant.

The sequence of the RT PCR and qPCR primers are listed in Table 5. Primer sequences for internal controls:

human GAPDH F:
(SEQ ID NO: 21)
5'-TGCACCACCAACTGCTTAGC-3' human GAPDH R:
(SEQ ID NO: 22)
5'-GGCATGGACTGTGGTCATGAG-3' murine β-actin F:
(SEQ ID NO: 23)
5'-GTGGTTTTGATTCTCCTGTGTGC-3' murine β-actin R:
(SEQ ID NO: 24)
5'-GCCTTGTACCCATCAGGGA-3'

TABLE 5

| GI | Name | Forward Primer (SEQ ID NO) | Reverse Primer (SEQ ID NO) |
|---|---|---|---|
| GI: 145651814 | HERV-R_7q21.2 | F: CCATGGGAAGCAAGGGAACT (25) | R: CTTTCCCCAGCGAGCAATAC (26) |
| GI: 195963433 | HERV-W_7q21.2 | F: CCCCATCGTATAGGAGTCTT (27) | R: CCCCATCAGACATACCAGTT (28) |
| GI: 300796687 | HERV-V_19q13.41 ENV 1 | F: TGATGGCCTCCTTGGAAACG (29) | R: CAGGTGTAGCCAGTGTAGCC (30) |
| GI: 300796709 | HERV-V_19q13.41 ENV 2 | F: CTCTGAGGAGGGATTCCCCA (31) | R: AGTCAAGTTAGGGTGGCAGC (32) |
| GI: 44887863 | HERV-F(c)1_Xq21.33 | F: GGGCCACTAAGTTACTAGGTC (33) | R: AGTTAGGAGGGAGTTACTGGG (34) |
| GI: 44887864 | HERV-FRD_6p24.1 | F: GCCTGCAAATAGTCTTCTTT (35) | R: ATAGGGGCTATTCCCATTAG (36) |
| GI: 44887882 | HERV-R(b)_3p24.3 | F: GGACAGTGCCGACATACTAT (37) | R: TAGAGTGCAGCATCCTAACC (38) |
| GI: 44887888 | HERV-H_3q26 | F: ACTACACACATCACTGAAACAAA (39) | R: GGATGGAGTGAAATACAGGAC (40) |
| GI: 44887889 | HERV-H_2q24.3 | F: TTCACTCCATCCTTGGCTAT (41) | R: CGTCGAGTATCTACGAGCAAT (42) |
| GI: 47605576 | HERV-K_1q23.3 | F: CACAACTAAAGAAGCTGACG (43) | R: CATAGGCCCAGTTGGTATAG (44) |
| GI: 47716681 | HERV-T_19q13.11 | F: CCAGGATTTGATGTTGGG (45) | R: GGGGTGAGGTTAAGGAGATGG (46) |

Promoter Assay

The LTR of Mmergln-int PCR amplified from BAC RP 23-2D22 cloned into the promoterless pGL3 basic vector with the following primers:

LTR F:
(SEQ ID NO: 47)
5'-GGTTCCAACTCGAGTGAAAGGAAATA-3'

LTR R:
(SEQ ID NO: 48)
5'-GGTTCCAAAAGCTTTGAAAGAACTCA-3'.

The p21 and p21 mutant constructs are described in [Genes Dev. 1995 Apr. 15; 9(8):935-44.] Mutations to the Mmergln-LTR were generated using QuikChange II Site-Directed Mutagenesis Kit. A deletion was made at bases 104-123 with the following primers:

del104-123 F:
(SEQ ID NO: 49)
5'-ATAGCAGAACAGACCAATCGCCTCCCTAGCTC-3' del104-123 R:
(SEQ ID NO: 50)
5'-GAGCTAGGGAGGCGATTGGTCTGTTCTGCTAT-3'.

A single cytosine to adenine transversion mutations were made with the following primers:

c107a F:
(SEQ ID NO: 51)
5'-AGAACAGACCAGGAAATGCCCGGGCAAGC-3' c107a R:
(SEQ ID NO: 52)
5'-GCTTGCCCGGGCATTTCCTGGTCTGTTCT-3' c117a F:
(SEQ ID NO: 53)
5'-GACATGCCCGGGAAAGCCCATCGCC-3' c117a R:
(SEQ ID NO: 54)
5'-GGCGATGGGCTTTCCCGGGCATGTC-3'.

Two cytosine to adenine transversion mutations were made with primers:

c107a c117a F:
(SEQ ID NO: 55)
5'-ACAGACCAGGAAATGCCCGGGAAAGCCCATCGC-3' c107a c117a R:
(SEQ ID NO: 56)
5'-GCGATGGGCTTTCCCGGGCATTTCCTGGTCTGT-3'.

To generate the single base substitutions, the following thermocycler conditions were used: 95° C. 30 sec/95° C. 30 sec, 55° C. 1 min, 68° C. 5 min 30 sec for 16 cycles to generate the deletion; and 95° C. 30 sec/95° C. 30 sec, 55° C. 1 min, 68° C. 5 min 30 sec for 18 cycles to generate the double base substitutions. p53+/+ and p53−/− MEFs were plated in 48-well tissue culture plates at a density of 3×10⁴ per well. MEFs were co-transfected with the 50 ng/well of the pRL-TK Renilla reporter vector (Promega Corp., Madison, Wis.) and 200 ng/well of the pGL3 basic experimental constructs. Cells were lysed and luciferase activity was measured 48 hours post transfection using DUAL-LUCIFERASE reporter assay system (Promega Corp., Madison, Wis.) according to manufacturer's instructions.

Western Blots

Protein was harvested with SDS sample buffer, run on 10% SDS-polyacrylamide gels, and transferred to a PVDF membrane overnight at 20 V. The membranes were blocked with 5% milk in TBS-T, incubated with the primary antibodies and secondary antibodies diluted in 5% milk in TBS-T. Protein was visualized using GeneMate Chemiluminescent HRP substrate (BioExpress, Kaysville, Utah). Anti-hERVantibody (ab71115, Abcam PLC, Cambridge, Mass.) was used at a concentration of 1:1,000 to detect Syncytin 1 and anti-HERV-FRD (ab90733) was used at a concentration of 1:100 to detect Syncytin 2 protein levels. For a loading control GAPDH rabbit mAb (#2118, Cell Signaling Technology, Inc., Danvers, Mass.) was used at a concentration of 1:2,000.

ChIP

Chromatin immunoprecipitation was performed using a Magna ChIP A kit (Millipore Corp., Billerica, Mass.) was used according to p53 (1C12) Mouse mAb (#2524, Cell Signaling Technology, Inc., Danvers, Mass.).

Primers to detect LTR:

ChIP LTR Fi
(SEQ ID NO: 57)
5'-GCTGAGAACATAGCAGAACAGACC-3'

ChIP LTR Ri
(SEQ ID NO: 58)
5'-GCACCCAAGAATCACGAATAGAAC-3'

ChIP LTR Rii
(SEQ ID NO: 59)
5'-AACAGGAGACAGTGGATTCGACC-3'

Primers used as positive control:

Mdm2-F chip:
(SEQ ID NO: 60)
5'-GGTGCCTGGTCCCGGACTCGCCGGG-3'

Mdm2-R chip:
(SEQ ID NO: 61)
5'-CCGAGAGGGTCCCCCAGGGGTGTCC-3' p21-F chip:
(SEQ ID NO: 62)
5'-CCTTTCTATCAGCCCCAGAGGATACC-3' p21-R chip:
(SEQ ID NO: 63)
5'-GGGACGTCCTTAATTATCTGGGGTC-3'

Bax-F chip:
(SEQ ID NO: 64)
5'-GATGTTGTAGCCACCGCGTACAGCC-3'

Bax-R chip:
(SEQ ID NO: 65)
5'-TTCATGGTAGAGAGCACTAAGGAGG-3'

Immunofluorescence and Microscopy

Immunofluorescence was performed according to Spector, D. L. and H. C. Smith. 1986. *Exp. Cell Res.* 163, 87-94. Imaging was performed on a DeltaVision Elite live cell microscope (Applied Precision, Issaqua, Wash.) using the 40× objective.

Bioinfomatics mRNA Expression Analysis mRNA transcript levels were detected by hybridization to Illumina bead arrays (Illumina, Inc., San Diego, Calif.). Each dataset was separately assessed for signal quality, quantile normalized and then probe sets mapping to the same gene were averaged.

RNA Seq

The RNA integrity was verified by quantification using a RIBOGREEN assay (Invitrogen, Life Technologies Corp., Grand Island, N.Y.) and an Agilent RNA 6000 Nano chip (Agilent Technologies, Inc., Santa Clara, Calif.). Samples with an RNA Integrity Number (RIN) of 8 or above were used for mRNA seq library preparation. To prepare the library, mRNA was purified and fragmented. Next, cDNA was generated, end repair was performed, the 3' ends were adenylated and the DNA fragments were ligated to adaptors. Ligation products were purified from an gel. The library was quantified and validated using an Agilent High Sensitivity chip (Agilent Technologies, Inc., Santa Clara, Calif.), PICOGREEN (Invitrogen, Life Technologies Corp., Grand Island, N.Y.) assay and KAPA qPCR (KAPA Biosystems, Inc., Wilmington, Mass.).

The characterization of repetitive elements was performed using the Table Browser function of the UCSC Genome Browser, and the classification of the repetitive elements was determined using BLAT and the Repeat Masker function (Jurka et al., 2005. *Cytogentic and Genome Research* 110:462-467). Identification of sequences of homology of to Mmergln-int were identified using the BLAT feature of the UCSC Genome Browser. Open reading frames were determined using NCBI's Open Reading Frame Finder. NCBI's Conserved Domain Database was used to identify species containing protein domains of the Ebola HIV-1-like HR1-HR2 Superfamily.

Mmergln-Int ENV Enhances Tumorigenicity In Vivo

LLC1 cells (ATCC# CRL-1642) were transfected with vectors containing GFP, ERV, and ENV transgenes as described earlier using the NEON transfection system (Invitrogen, Life Technologies Corp., Grand Island, N.Y.) or the FuGENE HD transfection reagent (Promega Corp., Madison, Wis.). Using the NEON transfection system, LLC1 cells were pulsed once with a pulse voltage of 1,350 V and a pulse width of 30 ms at a density of $5 \times 10^6$/ml cells. To generate stable cell lines, LLC1 cells were selected with puromycin.

The ERV and ENV constructs were generated as described above. The Mmergln-int F (SEQ ID NO:5) and Mmergln-int R (SEQ ID NO:6) primers were used with thermocycler conditions 94° C. 1 min/94° C. 30 sec, 58° C. 1 min, 72° C. 9 min for 30 cycles/72° C. 10 min to generate the ERV construct. The ENV construct was generated using the Env F (SEQ ID NO:9) and Env R (SEQ ID NO:10), and thermocycler conditions 94° C. 1 min/94° C. 30 sec, 58° C. 1 min, 72° C. 2 min for 30 cycles/72° C. 10 min. The GFP construct was obtained from Addgene, Cambridge, Mass.). The cells containing the designated transgenes were selected by using puromycin.

$2 \times 10^5$ cells of each genotype were inoculated in C57BL mice (The Jackson Laboratory, Bar Harbor, Me.) via tail vein injection. 15 mice per stable cell line were used.

Tumor growth was monitored by bio luminescence using IVIS spectrum in vivo imaging system (Xenogen Corp., Alameda, Calif.), after delivering 100 µl of 28.5 mg/ml luciferin (Gold Biotechnology, Inc., St. Louis, Mo.) in mice by intraperitoneal injection.

For survival curves, statistical analyses (Kaplan Meier) were performed by using Prism 4 (GraphPad Software), and p values were calculated by the log-rank test. All other p values were calculated using Student's t test (unpaired, two-tailed, $p < 0.05$ was considered significant).

Results are shown in FIG. 14.

Structural Analysis

The structural analysis of the envelope protein was carried out by using the open source Conserved Domain (CD) Search software tool available at ncbi.nlm.nih.gov/Structure/cdd/wrpsb.cgi using the following amino acid sequence of Mmergln-int envelope (SEQ ID NO:66):

MMSGLWRRLLILLSCACFVGAIPKDFNPHSPVQQTWEVLNEEGRAVWTIA

EVHPLWTWWPDLFPDICKLAIGAPPGWDLEGYSDIQRAPLTPPPYVEKHL

RDPWGGCSNQRDRSMLRTHPFYVCPGPHQSQSLNPTCGGKADFFCKSWGC

ETSGTARWKPSSSWDYIRVTANYSLASYVPGGFDLDECTDWCHPLRVTFT

EPGKRALGWTRGYTWGLRIYKERYDEGLLFTIRLKIETPYNPLGPPTKFT

PLTHTITQPTPVIADPLNMAAITQPPTPQVPLTITPTIPSRQRMFNLVRG

AFYALNRTDPSATEDCWLCLSSGPPYYEGIAFNGDFNRISSHTSCSWGTG

QKLTLTEVSVRNPGLCIGTPPSTHKHLCGQIQSMSRTEANYYLVPSPVGW

-continued
WACNTGLTPCVSTKVFNSSHDFCVMIQLLPHVYYHPASSLEESYAGRRSK

REPTTLTLAAFMGIGMAVGVGTGVSALIEGRQGIQSLRDAVNEDLAAIEK

SIDALKKSLTSLSEVVLQNRRGLDLLFLKEGGLCAALKEECCFYADHTGI

VRDSMQKLREKLERRKPERDAQRGWFESWFESRPSWITSLISAVAGPILM

ICLALVFSPCIINRGMAFIQSKIDTVKLMVLQRQYQPIVQVDEELGDTNL

Results are shown in FIG. 15.

Similar structural analyses, using the same open source software, were performed using the following amino acid sequences of other envelope proteins.

ENVW-1 (SEQ ID NO:67)

MALPYHIFLFTVLLPSFTLTAPPPCRCMTSSSPYQEFLWRMQRPGNIDAP

SYRSLSKGTPTFTAHTHMPRNCYHSATLCMHANTHYWTGKMINPSCPGGL

GVTVCWTYFTQTGMSDGGGVQDQAREKHVKEVISQLTRVHGTSSPYKGLD

LSKLHETLRTHTRLVSLFNTTLTGLHEVSAQNPTNCWICLPLNFRPYVSI

PVPEQWNNFSTEINTTSVLVGPLVSNLEITHTSNLTCVKFSNTTYTTNSQ

CIRWVTPPTQIVCLPSGIFFVCGTSAYRCLNGSSESMCFLSFLVPPMTIY

TEQDLYSYVISKPRNKRVPILPFVIGAGVLGALGTGIGGITTSTQFYYKL

SQELNGDMERVADSLVTLQDQLNSLAAVVLQNRRALDLLTAERGGTCLFL

GEECCYYVNQSGIVTEKVKEIRDRIQRRAEELRNTGPWGLLSQWMPWILP

FLGPLAAIILLLLFGPCIFNLLVNFVSSRIEAVKLQMEPKMQSKTKIYRR

PLDRPASPRSDVNDIKGTPPEEISAAQPLLRPNSAGSS

ENVFRD-1 (SEQ ID NO:68)

MGLLLLVLILTPSLAAYRHPDFPLLEKAQQLLQSTGSPYSTNCWLCTSSS

TETPGTAYPASPREWTSIEAELHISYRWDPNLKGLMRPANSLLSTVKQDF

PDIRQKPPIFGPIFTNINLMGIAPICVMAKRKNGTNVGTLPSTVCNVTFT

VDSNQQTYQTYTHNQFRHQPRFPKPPNITFPQGTLLDKSSRFCQGRPSSC

STRNFWFRPADYNQCLQISNLSSTAEWVLLDQTRNSLFWENKTKGANQSQ

TPCVQVLAGMTIATSYLGISAVSEFFGTSLTPLFHFHISTCLKTQGAFYI

CGQSIHQCLPSNWTGTCTIGYVTPDIFIAPGNLSLPIPIYGNSPLPRVRR

AIHFIPLLAGLGILAGTGTGIAGITKASLTYSQLSKEIANNIDTMAKALT

TMQEQIDSLAAVVLQNRRGLDMLTAAQGGICLALDEKCCFWVNQSGKVQD

NIRQLLNQASSLRERATQGWLNWEGTWKWFSWVLPLTGPLVSLLLLLLFG

PCLLNLITQFVSSRLQAIKLQTNLSAGRHPRNIQESPF

ENVF(c)-1 (SEQ ID NO:69)

MARPSPLCLLLLLTLLTPIVPSNSLLTEPPFRWRFYLHETWTQGNRLSTV

TLATVDCQPHGCQAQVTFNFTSFKSVLRGWSNPTICFVYDQTHSNCRDYW

VDTNGGCPYAYCRMHVTQLHTAKKLQHTYRLTSDGRTTYFLTIPDPWDSR

WVSGVTGRLYRWPTDSYPVGKLRIFLTYIRVIPQVLSNLKDQADNIKHQE

EVINTLVQSHPKADMVTYDDKAEAGPFSWITLVRHGARLVNMAGLVNLSH

CFLCTALSQPPLVAVPLPQAFNTSGNHTAHPSGVFSEQVPLFRDPLQPQF

PFCYTTPNSSWCNQTYSGSLSNLSAPAGGYFWCNFTLTKHLNISSNNTLS

RNLCLPISLVPRLTLYSEAELSSLVNPPMRQKRAVFPPLVIGVSLTSSLV

ASGLGTGAIVHFISSSQDLSIKLQMAIEASAESLASLQRQITSVAKVAMQ

NRRALDLLTADKGGTCMFLGEECCYYINESGLVETSLLTLDKIRDGLHRP

SSTPNYGGGWWQSPLTTWIIPFISPILIICLLLLIAPCVLKFIKNRISEV

SRVTVNQMLLHPYSRLPTSEDHYDDALTQQEAAR

ENVF(c)-2 (SEQ ID NO:70)

MNSPCDRLQQFIQVLLEESWSFPSFANTLHWPENLLSYIDELVWQGSLQN

FHQHEVRFDKPPLLPLTGFSSLTENWSSRQAVSSRLVATAASPPAGCQAP

IAFLGLKFSSLGPARKNPALCFLYDQSNSKCNTSWVKENVGCPWHWCNIH

EALIRTEKGSDPMFYVNTSTGGRDGFNGFNLQISDPWDPRWASGVDGGLY

EHKTFMYPVAKIRIARTLKTTVTGLSDLASSIQSAEKELTSQLQPAADQA

KSSRFSWLTLISEGAQLLQSTGVQNLSHCFLCAALRRPPLVAVPLPTPFN

YTINSSTPIPPVPKGQVPLFSDPIRHKFPFCYSTPNASWCNQTRMLTSTP

APPRGYFWCNSTLTKVLNSTGNHTLCLPISLIPGLTLYSQDELSHLLAWT

EPRPQNKSKWAIFLPLVLGISLASSLVASGLGKGALTHSIQTSQDLSTHL

QLAIEASAESLDSLQRQITTVAQVAAQNRQALDLLMAEKGRTCLFLQEEC

CYYLNESGVVENSLQTLKKKKSSKRS

ENV-T (SEQ ID NO:71)

MGPEAWVRPLKTAPKPGEAIRLILFIYLSCFFLPVMSSEPSYSFLLTSFT

TGRVFANTTWRAGTSKEVSFAVDLCVLFPEPARTHEEQHNLPVIGAGSVD

LAAGFGHSGSQTGCGSSKGAEKGLQNVDFYLCPGNHPDASCRDTYQFFCP

DWTCVTLATYSGGSTRSSTLSISRVPHPKLCTRKNCNPLTITVHDPNAAQ

WYYGMSWGLRLYIPGFDVGTMFTIQKKILVSWSSPKPIGPLTDLGDPIFQ

KHPDKVDLTVPLPFLVPRPQLQQQHLQPSLMSILGGVHHLLNLTQPKLAQ

DCWLCLKAKPPYYVGLGVEATLKRGPLSCHTRPRALTIGDVSGNASCLIS

TGYNLSASPFQATCNQSLLTSISTSVSYQAPNNTWLACTSGLTRCINGTE

PGPLLCVLVHVLPQVYVYSGPEGRQLIAPPELHPRLHQAVPLLVPLLAGL

SIAGSAAIGTAALVQGETGLISLSQQVDADFSNLQSAIDILHSQVESLAE

VVLQNCRCLDLLFLSQGGLCAALGESCCFYANQSGVIKGTVKKVRENLDR

HQQERENNIPWYQSMFNWNPWLTTLITGLAGPLLILLLSLIFGPCILNSF

LNFIKQRIASVKLTYLKTQYDTLVNN

ENV-H1 (SEQ ID NO:72)

MIFAGKAPSNTSTLMKFYSLLLYSLLFSFPFLCHPLPLPSYLHHTINLTH

SLLAASNPSLVNNCWLCISLSSSAYTAVPAVQTDWATSPISLHLRTSFNS

PHLYPPEELIYFLDRSSKTSPDISHQQAAALLRTYLKNLSPYINSTPPIF

GPLTTQTTIPVAAPLCISWQRPTGIPLGNLSPSRCSFTLHLRSPTTNINE

TIGAFQLHITDKPSINTDKLKNISSNYCLGRHLPCISLHPWLSSPCSSDS

PPRPSSCLLIPSPENNSERLLVDTRRFLIHHENRTFPSTQLPHQSPLQPL
TAAALAGSLGVWVQDTPFSTPSHLFTLHLQFCLAQGLFFLCGSSTYMCLP
ANWTGTCTLVFLTPKIQFANGTEELPVPLMTPTQQKRVIPLIPLMVGLGL
SASTVALGTGIAGISTSVMTFRSLSNDFSASITDISQTLSVLQAQVDSLA
AVVLQNRRGLDLLTAEKGGLCIFLNEECCFYLNQSGLVYDNIKKLKDRAQ
KLANQASNYAEPPWALSNWMSWVLPIVSPLIPIFLLLLFGPCIFRLVSQF
IQNRIQAITNHSIRQMFLLTSPQYHPLPQDLPSA

ENV-H2 (SEQ ID NO:73)

MIFAGRASSNTSTLMKFYSLLLYSLLFSFPILCHPLPLPSYLHHTINLTH
SLLAVSNPSLAKNCWLCISLPSSAYPAVPALQTDWGTSPVSPHLRTSFNS
PHLYPPEKLIYFLDRSSKTSPDISHQQAAALLCTYLKNLSPYINSTPPTF
GPLTTQTTIPVAAPLCISRQRPTGIPLGNLSPSRCSFTLHLRSPTTHITE
TNGAFQLHITDKPSINTDKLKNVSSNYCLGRHLSCISLHPWLFSPCSSDS
PPRPSSCLLIPSPKNNSESLLVDAQRFLIYHENRTSPSTQLPHQSPLQPL
TAAPLGGSLRVWVQDTPFSTPSHLFTLHLQFCLVQSLFFLCGSSTYMCLP
ANWTGTCTLVFLTSKIQFANGTEELPVPLMTPTRQKRVIPLIPLMVGLGL
SASTVALGTGIAGISTSVTTFRILSNDFSASITDISQTLSGLQAQVDSSA
AVVLQNRQGLDLLTAEKGGLCIFLNEESYFLNQSGLVYDNIKKLKDKAQ
NLANQASNYAEPPWPLSNWMSWVLPILSPLIPIFLLLFFRPCIFHLVSQF
IQNHIQAITDHSI

ENV-H3 (SEQ ID NO:74)

MILAGRAPSNTSTLMKFYSLLLYSLLFSFPFLYHPLPLPSYLHHTINLTH
SLPAASNPSLANNCWLCISLSSSAYIAVPTLQTDRATSPVSLHLRTSFNS
PHLYPPEELIYFLDRSSKTSPDISHQPAAALLHIYLKNLSPYINSTPPIF
GPLTTQTTIPVAAPLCISRQRPTGIPLGNISPSRCSFTLHLQSPTTHVTE
TIGVFQLHIIDKPSINTDKLKNVSSNYCLGRHLPYISLHPWLPSPCSSDS
PPRPSSCLLTPSPQNNSERLLVDTQRFLIHHENRTSSSMQLAHQSPLQPL
TAAALAGSLGVWVQDTPFSTPSHPFSLHLQFCLTQGLFFLCGSSTYMCLP
ANWTGTCTLVFLTPKIQFANGTKELPVPLMTLTPQKRVIPLIPLMVGLGL
SASTIALSTGIAGISTSVTTFRSPSNDFSASITDISQTLSVLQAQVDSLA
AVVLQNRRGLGLSILLNEECCFYLNQSGLVYENIKKLKDRAQKLANQASN
YAESPWALSNWMSWVLPILSPLIPIFLLLLFGPCIFHLVSQFIQNRIQAI
TNHSI

ENV-R (SEQ ID NO:75)

MLGMNMLLITLFLLLPLSMLKGEPWEGCLHCTHTTWSGNIMTKTLLYHTY
YECAGTCLGTCTHNQTTYSVCDPGRGQPYVCYDPKSSPGTWFEIHVGSKE
GDLLNQTKVFPSGKDVVSLYFDVCQIVSMGSLFPVIFSSMEYYSSCHKNR
YAHPACSTDSPVTTCWDCTTWSTNQQSLGPIMLTKIPLEPDCKTSTCNSV

NLTILEPDQPIWTTGLKAPLGARVSGEEIGPGAYVYLYIIKKTRTRSTQQ
FRVFESFYEHVNQKLPEPPPLASNLFAQLAENIASSLHVASCYVCGGMNM
GDQWPWEARELMPQDNFTLTASSLEPAPSSQSIWFLKTSIIGKFCIARWG
KAFTDPVGELTCLGQQYYNETLGKTLWRGKSNNSESPHPSPFSRFPSLNH
SWYQLEAPNTWQAPSGLYWICGPQAYRQLPAKWSGACVLGTIRPSFFLMP
LKQGEALGYPIYDETKRKSKRGITIGDWKDNEWPPERIIQYYGPATWAED
GMWGYRTPVYMLNRIIRLQAVLEIITNETAGALNLLAQQATKMRNVIYQN
RLALDYLLAQEEGVCGKFNLTNCCLELDDEGKVIKEITAKIQKLAHIPVQ
TWKG

ENV-R(b) (SEQ ID NO:76)

MDPLHTIEKVPARRNIHDRGHQGHRMGDGTPGRPKISVQQMTRFSLIIFF
LSAPFVVNASTSNVFLQWAHSYADGLQQGDPCWVCGSLPVTNTMELPWWV
SPLQGKDWVFFQSFIGDLKQWTGAQMTGVTRKNISEWPINKTLNEPGHDK
PFSVNETRDKVIAFAIPLLDTKVFVQTSRPQNTQYRNGFLQIWDGFIWLT
ATKGHLSQIAPLCWEQRNHSLDNWPNTTRVMGWIPPGQCRHTILLQQRDL
FATDWSQQPGLNWYAPNGTQWLCSPNLWPWLPSGWLGCCTLGIPWAQGRW
VKTMEVYPYLPHVVNQGTRAIVHRNDHLPTIFMPSVGLGTVIQHIEALAN
FTQRALNDSLQSISLMNAEVYYMHEDILQNRMALDILTAAEGGTCALIKT
ECCVYIPNNSRNISLALEDTCRQIQVISSSALSLHDWIASQFSGRPSWWQ
KILIVLATLWSVGIALCCGLYFCRMFSQHIPQTHSIIFQQELPLSPPSQE
HYQSQRDIFHSNAP

ENV-K1 (SEQ ID NO:77)

MHPSEMQRKAPPRRRRHRNRAPLTHKMNKMVTSEQMKLPSTKKAEPPTWA
QLKKLTQLATKYLENTKVTQTPESMLLAALMIVSMVVSLPMPAGAAAANY
TNWAYVPFPPLIRAVTWMDNPIEVYVNDSVWVHGPIDDRCPAKPEEEGMM
INISIGYHYPPICLGRAPGCLMPAVQNWLVEVPTVSPISRFTYNMVSGMS
LRPRVNYLQDFSYQRSLKFRPKGKPCPKEIPKESKNTEVLVWEECVANSV
VILQNNEFGTIIDWAPRGQFYHNCSGQTQSCPSAQVSPAVDSDLTESLDK
HKHKKLQSFYPWEWGEKGISTPRPKIISPVSGPEHPELWRLTVASHHIRI
WSGNQTLETRDRKPFYTVDLNSSLTVPLQSCVKPPYMLVVGNIVIKPDSQ
TITCENCRLLTCIDSTFNWQHRILLVRAREGVWIPVSMDRPWEASPSIHI
LTEVLKGVLNRSKRFIFTLIAVIMGLIAVTAMAAVAGVALHSFVQSVNFV
NDWQKNSTRLWNSQSSIDQKLANQINDLRQTVIWMGDRLMSLEHRFQLQC
DWNTSDFCITPQIYNESEHHWDMVRRHLQGREDNLTLDISKLKEQIFEAS
KAHLNLVPGTEAIAGVADGLANLNPVTWVKTIGSTTIINLILILVCLFCL
LLVCRFTQQLRRDSYHRERAMMTMVVLSKRKGGNVGKSKRDQIVTVSV

ENV-K2 (SEQ ID NO:78)

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTYWAYVPFPPLIRAVTWMDNPTEVYVNDSVWVPGPIDDRCPAKPEEEGM
MINISIGYHYPPICLGRAPGCLMPAVQNWLVEVPTVSPICRFTYHMVSGM
SLRPRVNYLQDFSYQRSLKFRPKGKPCPKEIPKESKNTEVLVWEECVANS
AVILQNNEFGTIIDWAPRGQFYHNCSGQTQSCPSAQVSPAVDSDLTESLD
KHKHKKLQSFYPWEWGEKGISTPRPKIVSPVSGPEHPELWRLTVASHHIR
IWSGNQTLETRDRKPFYTIDLNSSLTVPLQSCVKPPYMLVVGNIVIKPDS
QTITCENCRLLTCIDSTFNWQHRILLVRAREGVWIPVSMDRPWEASPSVH
ILTEVLKGVLNRSKRFIFTLIAVIMGLIAVTATAAVAGVALHSSVQSVNF
VNDWQKNSTRLWNSQSSIDQKLANQINDLRQTVIWMGDRLMSLEHRFQLQ
CDWNTSDFCITPQIYNESEHHWDMVRRHLQGREDNLTLDISKLKEQIFEA
SKAHLNLVPGTEAIAGVADGLANLNPVTWVKTIGSTTIINLILILVCLFC
LLLVCRCTQQLRRDSDHRERAMMTMAVLSKRKGGNVGKSKRDQIVTVSV

ENV-K3 (SEQ ID NO:79)

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTYWAYVPFPPLIRAVTWMDNPIEVYVNDSVWVPGPTDDHCPAKPEEEGM
MINISIGYRYPPICLGRAPGCLMPAVQNWLVEVPTVSPISRFTYHMVSGM
SLRPRVNYLQDFSYQRSFKFRPKGKPCPKEIPKESKNTEVLVWEECVANS
AVILQNNEFGTIIDWAPRGQFYHNCSGQTQSCPSAQVSPAVDSDLTESLD
KHKHKKLQSFYPWEWGEKGISTPRPKIISPVSGPEHPELWRLTVASHHIR
IWSGNQTLETRDRKPFYTVDLNSSVTVPLQSCIKPPYMLVVGNIVIKPDS
QTITCENCRLLTCIDSTFNWQHRILLVRAREGVWIPVSMDRPWETSPSIH
TLTEVLKGVLNRSKRFIFTLIAVIMGLIAVTATAAVAGVALHSSVQSVNF
VNDWQKNSTRLWNSQSSIDQKLANQINDLRQTVIWMGDRLMSLEHRFQLQ
CDWNTSDFSITPQIYNESEHHWDMVRRHLQGREDNLTLDISKLKEQIFEA
SKAHLNLVPGTEAIAGVADGLANLNPVTWVKTIGSTTIINLILILVCLFC
LLLVCRCTQQLRRDSDHRERAMMTMAVLSKRKGGNVGKSKRDQIVTVSV

ENV-K4 (SEQ ID NO:80)

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTNWAYVPFPPLIRAVTWMDNPIEVYVNDSVWVPGPIDDRCPAKPEEEGM
MINISIGYRYPICLGRAPGCLMPAVQNWLVEVPIVSPICRFTYHMVSGMS
LRPRVNYLQDFSYQRSLKFRPKGKPCPKEIPKESKNTEVLVWEECVANSA
VILQNNEFGTIIDWTPQGQFYHNCSGQTQSCPSAQVSPAVDSDLTESLDK
HKHKKLQSFYPWEWGEKGISTPRPKIISPVSGPEHPELWRLTVASHHIRI
WSGNQTLETRDRKPFYTVDLNSSLTLPLQSCVKPPYMLVVGNIVIKPDSQ

TITCENCRLLTCIDSTFNWQHRILLVRAREGVWIPVSMDRPWEASPSIHI
LTEVLKGVLNRSKRFIFTLIAVIMGLIAVTATAAVAGVALHSSVQSVNFV
NDGQKNSTRLWNSQSSIDQKLANQINDLRQTVIWMGDRLMSLEHRFQLQC
DWNTSDFCITPQIYNESEHHWDMVRRHLQGREDNLTLDISKLKEQIFEAS
KAHLNLVPGTEAIAGVADGLANLNPVTWVKTIGSTTIINLILILVCLFCL
LLVCRCTQQLRRDSDHRERAMMTMAVLSKRKGGNVGKSKRDQIVTVSV

ENV-K5 (SEQ ID NO:81)

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAAAN
YTYWAYVPFPPLIRAVTWMDNPIEIYVNDSVWVPGPTDDCCPAKPEEEGM
MINISIGYRYPPICLGRAPGCLMPAVQNWLVEVPTVSPISRFTYHMVSGM
SLRPRVNYLQDFSYQRSLKFRPKGKPCPKEIPKESKNTEVLVWEECVANS
AVILQNNEFGTLIDWAPRGQFYHNCSGQTQSCPSAQVSPAVDSDLTESLD
KHKHKKLQSFYPWEWGEKGISTARPKIISPVSGPEHPELWRLTVASHHIR
IWSGNQTLETRDRKPFYTIDLNSSLTVPLQSCVKPPYMLVVGNIVIKPDS
QTITCENCRLLTCIDSTFNWQHRILLVRAREGVWIPVSMDRPWEASPSVH
ILTEVLKGVLNRSKRFIFTLIAVIMGLIAVTATAAVAGVALHSSVQSVNF
VNDWQNNSTRLWNSQSSIDQKLANQINDLRQTVIWMGDRLMSLEHRFQLQ
CDWNTSDFCITPQIYNESEHHWDMVRCHLQGREDNLTLDISKLKEQIFEA
SKAHLNLVPGTEAIAGVADGLANLNTVTWVKTIGSTTIINLILILVCLFC
LLLVYRCTQQLRRDSDHRERAMMTMVLSKRKGGNVGKSKRDQIVTVSV

ENV-K6 (SEQ ID NO:82)

MNPSEMQRKAPPRRRRHRNRAPLTHKMNKMVTSEEQMKLPSTKKAEPPTW
AQLKKLTQLATKYLENTKVTQTPESMLLAALMIVSMVVSLPMPAGAAVAN
YTNWAYVPFPPLIRAVTWMDNPIEVYVNDSVWVPGPIDDRCPAKPEEEGM
MINISIGYRYPPICLGRAPGCLMPAVQNWLVEVPTVSPISRFTYHMVSGM
SLRPRVNYLQDFSYQRSLKFRPKGKPCPKEIPKESKNTEVLVWEECVANS
AVILQNNEFGTIIDWAPRGQFYHNCSGQTQSCPSAQVSPAVDSDLTESLD
KHKHKKLQSFYPWEWGEKRISTPRPKIVSPVSGPEHPELWRLTVASHHIR
IWSGNQTLETRDRKPFYTVDLNSSLTLPLQSCVKPPYMLVVGNIVIKPDS
QTITCENCRLLTCIDSTFNWQHRILLVRAREGVWIPVSMDRPWEASPSVH
ILTEVLKGVLNRSKRFIFTLIAVIMGLIAVTATAAVAGVALHSSVQSVNF
VNDGQKNSTRLWNSQSSIDQKLANQINDLRQTVIWMGDRLMSLEHRFQLQ
CDWNTSDFCITPQIYNDSEHHWDMVRRHLQGREDNLTLDISKLKEQIFEA
SKAHLNLVPGTEAIAGVADGLANLNPVTWVKTIGSTTIINLILILVCLFC
LLLVCRCTQQLRRDSDHRERAMMTMAVLSKRKGGNVGKSKRDQIVTVSV

Figure 16:
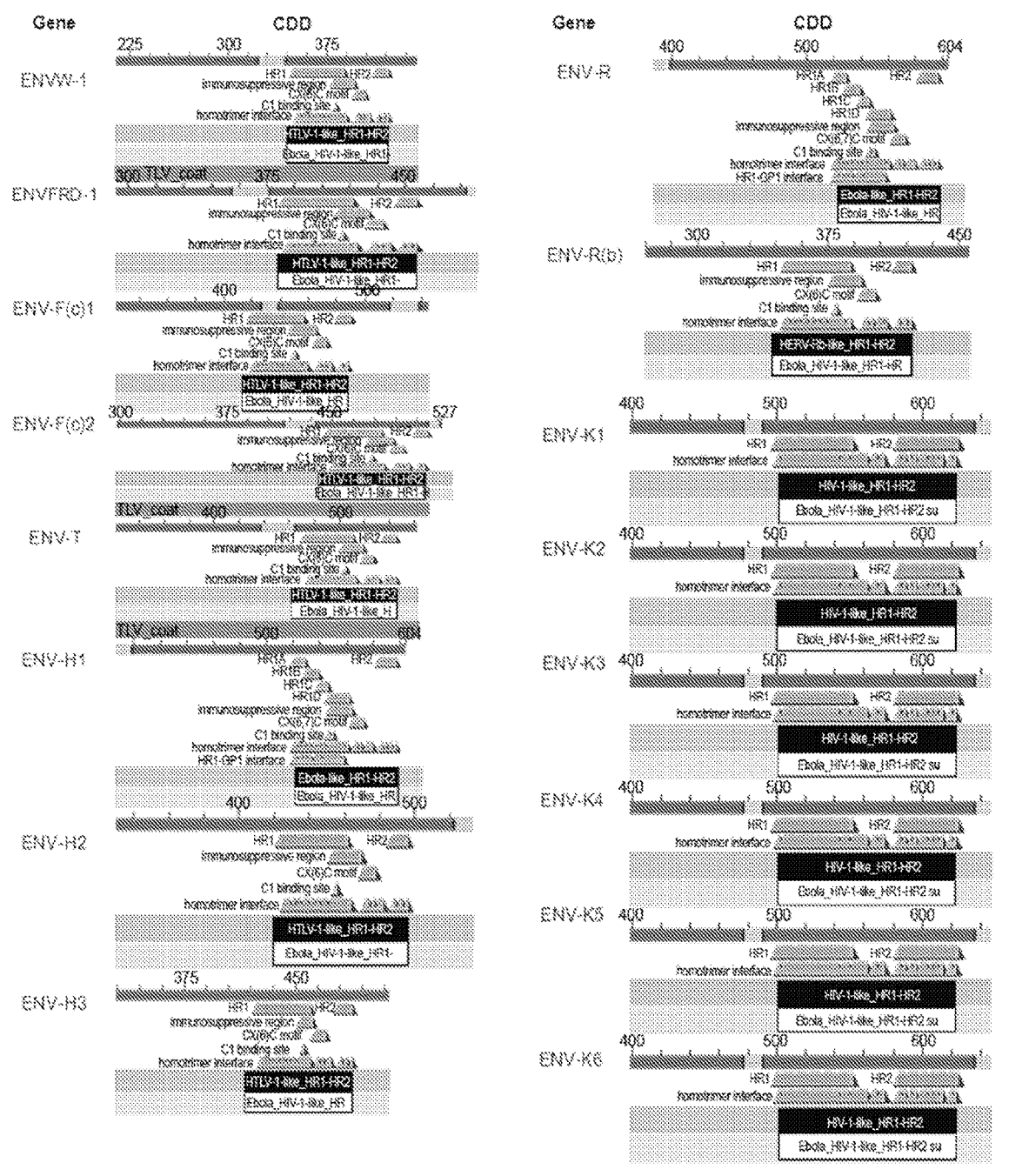

Results are shown in FIG. 16.

An alignment analysis of ENV-R (SEQ ID NO:75), ENV-R(b) (SEQ ID NO:76), ENV-T (SEQ ID NO:71), Mmergln-int envelope (SEQ ID NO:66), ENVF(c)-1 (SEQ ID NO:69), ENVF(c)-2 (SEQ ID NO:70), ENVW-1 (SEQ ID NO:67), ENVFRD-1 (SEQ ID NO:68), ENV-H2 (SEQ ID NO:73), ENV-H1 (SEQ ID NO:72), and ENV-H3 (SEQ ID NO:74) was performed using the open source software tool Clustal Omega (European Molecular Biology Laboratory, Cambridge, United Kingdom, www.ebi.ac.uk/Tools/msa/clustalo/). The alignment is presented using Jalview software (www.jalview.org/).

Results are shown in FIG. 18.

LISTING OF EXEMPLARY EMBODIMENTS

Embodiment 1

A method of slowing cellular growth, the method comprising:
increasing expression of an endogenous retrovirus envelope protein in at least one cell, wherein the cell expresses p53 and expression of the retrovirus envelope protein is controlled by p53; and exposing the cell to conditions that upregulate expression of p53.

Embodiment 2

A method of decreasing cell viability, the method comprising:
increasing expression of an endogenous retrovirus envelope protein in at least one cell, wherein the cell expresses p53 and expression of the retrovirus envelope protein is controlled by p53; and
exposing the cell to conditions that upregulate expression of p53.

Embodiment 3

The method of Embodiment 1 or Embodiment 2 wherein the conditions that upregulate expression of p53 comprise cellular stress.

Embodiment 4

The method of any preceding Embodiment wherein increasing expression of an endogenous envelope protein comprises overexpressing the endogenous envelope protein.

Embodiment 5

The method of Embodiment 4 wherein overexpressing the endogenous envelope protein comprises introducing into the cell a polynucleotide that comprises a coding region that encodes a functional portion of the endogenous envelope protein operably linked to a p53 response element.

Embodiment 6

The method of Embodiment 5 wherein the p53 response element comprises the polynucleotide sequence reflected in SEQ ID NO:1.

Embodiment 7

The method of Embodiment 5 wherein the p53 response element comprises at least 10 contiguous nucleotides of any one of: nucleotides 10-19 of SEQ ID NO:2, nucleotides 47-56 of SEQ ID NO:2, nucleotides 88-100 of SEQ ID NO:2, nucleotides 334-344 of SEQ ID NO:2, nucleotides 419-430 of SEQ ID NO:2, nucleotides 473-486 of SEQ ID NO:2, nucleotides 548-560 of SEQ ID NO:2, nucleotides 607-618 of SEQ ID NO:2, or nucleotides 679-690 of SEQ ID NO:2.

Embodiment 8

The method of Embodiment 5 wherein the p53 response element comprises nucleotides 169-179 of SEQ ID NO:3, nucleotides 246-255 of SEQ ID NO:3, nucleotides 337-346 of SEQ ID NO:3, nucleotides 371-380 of SEQ ID NO:3, nucleotides 460-469 of SEQ ID NO:3, nucleotides 524-533 of SEQ ID NO:3, nucleotides 588-597 of SEQ ID NO:3, nucleotides 786-795 of SEQ ID NO:3, nucleotides 800-809 of SEQ ID NO:3, nucleotides 892-901 of SEQ ID NO:3, or nucleotides 1122-1131 of SEQ ID NO:3.

Embodiment 9

The method of any preceding Embodiment wherein the subject is a mammal.

Embodiment 10

The method of Embodiment 9 wherein the mammal is a human.

Embodiment 11

A composition comprising a polynucleotide that comprises a coding region that encodes a functional portion of the endogenous envelope protein operably linked to a p53 response element.

Embodiment 12

The composition of Embodiment 11 wherein the p53 response element comprises the polynucleotide sequence reflected in SEQ ID NO:1.

Embodiment 13

The composition of Embodiment 11 wherein the p53 response element comprises at least 10 contiguous nucleotides of any one of: nucleotides 10-19 of SEQ ID NO:2, nucleotides 47-56 of SEQ ID NO:2, nucleotides 88-100 of SEQ ID NO:2, nucleotides 334-344 of SEQ ID NO:2, nucleotides 419-430 of SEQ ID NO:2, nucleotides 473-486 of SEQ ID NO:2, nucleotides 548-560 of SEQ ID NO:2, nucleotides 607-618 of SEQ ID NO:2, or nucleotides 679-690 of SEQ ID NO:2.

Embodiment 14

The composition of Embodiment 11 wherein the p53 response element comprises nucleotides 169-179 of SEQ ID NO:3, nucleotides 246-255 of SEQ ID NO:3, nucleotides 337-346 of SEQ ID NO:3, nucleotides 371-380 of SEQ ID NO:3, nucleotides 460-469 of SEQ ID NO:3, nucleotides 524-533 of SEQ ID NO:3, nucleotides 588-597 of SEQ ID NO:3, nucleotides 786-795 of SEQ ID NO:3, nucleotides 800-809 of SEQ ID NO:3, nucleotides 892-901 of SEQ ID NO:3, or nucleotides 1122-1131 of SEQ ID NO:3.

Embodiment 15

The composition of any one of Embodiments 11-14 further comprising a delivery vehicle.

Embodiment 16

A composition comprising antibody that specifically binds to an endogenous retrovirus envelope protein.

Embodiment 17

The composition of Embodiment 16 wherein the endogenous retrovirus envelope protein comprises HENV-R, HENV-W, HENV-V1, HENV-V2, HENV-F(c)1, HENV-FRD, HENV-R(b), HENV-H (3q26), HENV-H (2q24.3), HENV-K (1q23.3), HENV-K (12q14.1), HENV-T, ABB52637, hCG2039029, or Q4KWC9.

Embodiment 18

The composition of Embodiment 16 or Embodiment 17 wherein the antibody comprises a monoclonal antibody.

Embodiment 19

The composition of Embodiment 16 or Embodiment 17 wherein the antibody comprises polyclonal antibodies.

Embodiment 20

A method comprising:
obtaining a biological sample from a subject comprising cells from at least one tissue;
analyzing the cells for expression of an endogenous retrovirus envelope protein; and
identifying the subject as having or at risk of having cancer if the cells express the endogenous retrovirus envelope protein.

Embodiment 21

The method of Embodiment 20 wherein the tissue comprises human breast tissue or human prostate tissue.

Embodiment 22

The method of Embodiment 20 or Embodiment 21 wherein the endogenous retrovirus envelope protein comprises HENV-R, HENV-W, HENV-V1, HENV-V2, HENV-F(c)1, HENV-FRD, HENV-R(b), HENV-H (3q26), HENV-H (2q24.3), HENV-K (1q23.3), HENV-K (12q14.1), HENV-T, ABB52637, hCG2039029, or Q4KWC9.

Embodiment 23

The method of any one of Embodiments 20-22 further comprises providing to the subject a treatment effective for treating cancer.

Embodiment 24

The method of Embodiment 20 further comprising administering to the subject a pharmaceutical composition effective for treating cancer.

Embodiment 25

The method of Embodiment 24 wherein the pharmaceutical composition comprises a monoclonal antibody that specifically binds a tumor-associated antigen.

Embodiment 26

The method of Embodiment 24 or Embodiment 25 wherein the pharmaceutical composition comprises antibody that specifically binds to an endogenous retrovirus envelope protein.

Embodiment 27

The method of Embodiment 26 wherein the monoclonal antibody binds to the CKS-17 domain of the endogenous retrovirus envelope protein.

Embodiment 28

The method of any one of Embodiments 24-27 wherein the pharmaceutical composition comprises a compound that specifically binds to the CX(6)C domain of an endogenous retrovirus envelope protein.

Embodiment 29

A composition comprising:
antibody that specifically binds to the CKS-17 domain of the endogenous retrovirus envelope protein; and a pharmaceutically acceptable carrier.

Embodiment 30

The composition of Embodiment 29 wherein the antibody comprises a monoclonal antibody.

Embodiment 31

The composition of Embodiment 29 or Embodiment 30 further comprising a compound that specifically binds to the CX(6)C domain of the endogenous retrovirus envelope protein.

Embodiment 32

A composition comprising:
a compound that specifically binds to the CX(6)C domain of an endogenous retrovirus envelope protein; and a pharmaceutically acceptable carrier.

Embodiment 33

The composition of any one of Embodiments 29-32 further comprising antibody that specifically binds to a tumor-associated antigen.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of slowing cellular growth, the method comprising: overexpressing an endogenous HR1-HR2 superfamily retrovirus envelope protein in at least one cell, wherein the cell expresses p53 and expression of the retrovirus envelope protein is controlled by p53; and exposing the cell to conditions that upregulate expression of p53.

2. A method of decreasing cell viability, the method comprising: overexpressing an endogenous HR1-HR2 superfamily retrovirus envelope protein in at least one cell, wherein the cell expresses p53 and expression of the retrovirus envelope protein is controlled by p53; and exposing the cell to conditions that upregulate expression of p53.

3. The method of claim 1, wherein the conditions that upregulate expression of p53 comprise cellular stress.

4. The method of claim 1, wherein overexpressing the HR1-HR2 superfamily retrovirus endogenous envelope protein comprises introducing into the cell a polynucleotide that comprises a coding region that encodes a functional portion of the endogenous HR1-HR2 superfamily retrovirus envelope protein operably linked to a p53 response element.

5. The method of claim 1, wherein the subject is a mammal.

6. The method of claim 5, wherein the mammal is a human.

7. The method of claim 2, wherein the conditions that upregulate expression of p53 comprise cellular stress.

8. The method of claim 2, wherein overexpressing the HR1-HR2 superfamily retrovirus endogenous envelope protein comprises introducing into the cell a polynucleotide that comprises a coding region that encodes a functional portion of the HR1-HR2 superfamily retrovirus endogenous envelope protein operably linked to a p53 response element.

9. The method of claim 2, wherein the subject is a mammal.

10. The method of claim 9, wherein the mammal is a human.

* * * * *